United States Patent [19]
Palmer et al.

[11] Patent Number: 5,776,718
[45] Date of Patent: Jul. 7, 1998

[54] REVERSIBLE PROTEASE INHIBITORS

[75] Inventors: James T. Palmer, San Ramon; David Rasnick, San Francisco; Jeffrey Lee Klaus, Redwood City, all of Calif.

[73] Assignee: Arris Pharmaceutical Corporation, So. San Francisco, Calif.

[21] Appl. No.: 618,704

[22] Filed: Mar. 20, 1996

Related U.S. Application Data

[63] Continuation of Ser. No. 409,996, Mar. 24, 1995, Ser. No. 409,553, Mar. 24, 1995, Ser. No. 409,997, Mar. 24, 1995, and Ser. No. 410,000, Mar. 24, 1995.

[51] Int. Cl.$^6$ .............................. C12Q 1/37; C12Q 1/00; A01N 47/28
[52] U.S. Cl. .................... 435/23; 435/24; 435/4; 514/208; 514/1; 514/19; 514/12; 514/588; 514/600; 514/601; 424/70.24; 530/233; 530/336; 544/106
[58] Field of Search .................... 435/23, 24, 4; 514/208, 1, 19, 12, 588, 600, 601; 424/70.24; 530/233, 336; 544/106

[56] References Cited

U.S. PATENT DOCUMENTS

| | | | |
|---|---|---|---|
| 4,016,042 | 4/1977 | Svendsen | 514/19 |
| 4,891,356 | 1/1990 | Szabo | 514/19 |
| 4,908,309 | 3/1990 | Cho et al. | 435/23 |
| 5,053,333 | 10/1991 | Yamamoto | 435/23 |
| 5,055,451 | 10/1991 | Krantz et al. | 435/23 |
| 5,101,068 | 3/1992 | Palmer | 435/23 |
| 5,157,019 | 10/1992 | Glover et al. | 514/12 |
| 5,264,529 | 11/1993 | Maiti et al. | 514/202 |
| 5,288,612 | 2/1994 | Griffin et al. | 435/23 |
| 5,317,086 | 5/1994 | Bartlett et al. | 514/19 |
| 5,374,623 | 12/1994 | Zimmerman et al. | 435/23 |

FOREIGN PATENT DOCUMENTS

| | | |
|---|---|---|
| 04202170 | 7/1992 | Japan . |
| 04273896 | 9/1992 | Japan . |
| 04273897 | 9/1992 | Japan . |
| 05213990 | 8/1993 | Japan . |
| 92 08709 | 5/1992 | WIPO . |
| 92 16549 | 10/1992 | WIPO . |
| 93 14777 | 8/1993 | WIPO . |
| 93 16710 | 9/1993 | WIPO . |
| 94 18185 | 8/1994 | WIPO . |

OTHER PUBLICATIONS

Hanzlik, R. P., "Vinylogous Amino Acid Esters: A New Class of Inactivators for Thiol Proteases", *Journal of Medicinal Chemistry* vol. 27, No. 6, (1984) month not available.

Thompson, S. A., et al., "Carboxyl–Modified Amino Acids and Peptides as Protease Inhibitors", *J. Med. Chem.* 29:104–111 (1986) month not available.

Liu, S., et al., "Structure–Activity Relationships for Inhibition of Papain by Peptide Michael Acceptors", *J. Med. Chem.* 35(6):1067–1075 (1992) month not available.

Rawlings, N. D., et al., "Evolutionary families of peptidases", *J. Biochem.* 290:205–218 (1993) month not available.

Walker, B., et al., "Peptidylmethyl Sulfonium Salts, a New Class of Thiol Protease Inactivators", *Protease Inhibitors* (5974–5977), p. 1433 month not available.

Fehrentz, J-A. et al., "An Efficient Synthesis of Optically Active α-(t-Butoxycarbonylamino)-aldehydes from α-Amino Acids", *Communications*, pp. 676–678 (1983) month not available.

Mehdi, S., "Synthetic and Naturally Occurring Protease Inhibitors Containing an Electrophilic Carbonyl Group", *Bioorganic Chemistry* 21:249–259 (1993) month not available.

(List continued on next page.)

*Primary Examiner*—Louise Leary
*Attorney, Agent, or Firm*—Flehr Hohbach Test Albritton & Herbert LLP; David J. Brezner; Robin M. Silva

[57] ABSTRACT

The invention relates to novel reversible protease inhibitors. The inhibitors are specific to cysteine proteases.

53 Claims, 7 Drawing Sheets

OTHER PUBLICATIONS

Wadsworth, W. S., et al., "The Utility of Phosphonate Carbanions in Olefin Synthesis", |Contribution from Rohm and Haas Co., Philadelphia 37, Penna.| 83:1733–1738 (1961) month not available.

Brömme, D., et al., "Novel N–peptidyl–O–acyl hydroxamates: selective inhibitors of cysteine proteinases", Biochimica et Biophysica Acta. 1202:271–276 (1993) month not available.

Rosenthal, P. J., et al., "Antimalarial Effects of Peptide Inhibitors of a Plasmodium falciparum Cysteine Proteinase", J. Clin. Invest. 88:1467–1472 (1991) month not available.

Rasnick, D., "Synthesis of Peptide Fluoromethyl Ketones and the Inhibition of Human Cathepsin B", Analytical Biochemistry 149:461–465 (1985) month not available.

Kirschke, H., et al., "Rapid Inactivation of Cathepsin L by Z–Phe–Phechn$^{12}$ and Z Phe–Alachn$_2$", Biochemical and Biophysical Research Communications 101(2):454–458 (1981) month not available.

Krantz, A., et al., "Peptidyl (Acyloxy)methyl Ketones and the Quiescent Affinity Label Concept: The Departing Group as a Variable Structural Element in the Design of Inactivators of Cysteine Proteinases", Biochemistry 30:4678–4687 (1991) month not available.

Hanada, K., et al., "Isolation and Characterization of E–64, a New Thiol Protease Inhibitor" Agric. Biol. Chem. 42(3):523–528 (1978) month not available.

Sumiya, S., et al., "Molecular Design of Potent Inhibitor Specific for Cathespin B Based on the Tertiary Structure Prediction", Chem. Parm. Bull. 40(2):299–303 (1992) month not available.

Gour–Salin, B. J., et al., "Epoxysuccinyl Dipeptides as Selective Inhibitors of Cathepsin B", J. Med. Chem. 36:720–725 (1993) month not available.

Barrett, A. J., et al., "Proteinase inhibitors", Chapter 4, pp. 154–177, in Dingle, J. T., et al., Research monographs in cell and tissue physiology, vol. 12, Elsevier (1986) month not available.

Shaw, E., "Cysteinyl Proteinases and Their Selective Inactivation", Advances in Enzymology and Related Areas of Molecular Biology 63:271–347 (1990) month not available.

Anderson, M. B., et al., "Nucleophilic and Electrophilic Mercaptanylations via 2–(Trimethylsilyl)ethanethiol–Derived Reagents", J. Org. Chem. 53:3125–3127 (1988) month not available.

Spaltenstein, A., et al., "New Approaches to the Synthesis of trans–Alkene Isosteres of Dipeptides", J. Org. Chem. 52:3759–3766 (1987) month not available.

McIlwain, H., "Amino–suphonic Acid Analogues of Natural Amino–carboxylic Acids", Department of Bacterial Chemistry (Medical Research Council), Bland Sutton Institute of Pathology and the Courtauld Institute of Biochemistry pp. 75–77 (1941) month not available.

Engberts, J. B. F. N., et al., "The Mannich Condensation of Sulfinic Acids, Aldehyde, and Ethyl Carbamate", Recueil 84:942–950 (1965) month not available.

Esser, R. E., "Cysteine Proteinase Inhibitors Decrease Articular Cartilage and Bone Destruction in Chronic Inflammatory Arthritis", Arthritis & Rheumatism 37(2):236–247 (1994) month not available.

Sebti, S. M., et al., "Metabolic Inactivation: A Mechanism of Human Tumor Resistance to Bleomycin" Cancer Res., Jan. 1991 pp. 227–232.

Reetz, M.T., et al., "Stereoselective Nucleophilic Addition Reactions of Reactive Pseudopeptides", Angew. Chem. Int. Ed. Engl. 31(12):1626–1629, (1991).

Meng, Q., et al., "Synthetic Approaches toward Glidobamine, the Core Structure of the Glidobactin Antibiotics", Tetrahedron, 47(32): 6251–6264, (1991) month not available.

Schneider, J.J., "On the Reaction of Pentamethylcyclopentadiene with cobalt atoms: A Reexamination", Angew. Chem. Int. Ed. Engl., 31(10):1391–1392, (1992) month not available.

Smith, C.W., et al., "Synthesis and Renin Inhibitory Activity of Angiotensinogen Analogues Having Dehydrostatine, Leuψ|CH$_2$SO|Val at the P$_1$–P$_1$' Cleavage Site$^1$", J. Med. Chem. 31:1377–1382, (1988) month not available.

Barton, D.H.R., et al., "Synthesis of Novel α–Amino Acids and Derivatives using radical chemistry: synthesis of L– and D–α–Amino–Adipic Acids, L–α–Aminopimelic Acid and appropriate unsaturated derivatives", Tetrahedron, 43(19):4297–4308, (1987) month not available.

Jubb, J., et al., "Redox Chemistry of meso–Octaethylporphyrinogen: Formation and Opening of a Cyclopropane Ring", J. Am. Chem. Soc., 114:6571–6573, (1992) month not available.

Maryanoff, B.E., et al., "Molecular basis for the inhibition of human α–thrombin by the macrocyclic peptide cyclotheonamide A", Proc. Natl. Acad. Sci. USA, 90:8048–8052 (1993) month not available.

Rich, H.R., et al., "Synthesis of Analogues of the Carboxyl Protease Inhibitor Pepstatin. Effect of Structure on Inhibition of Pepsin and Renin$^1$", J. Med. Chem., 23:27–33, (1980) month not available.

Brillon, D., et al., "Silica Gel–Catalyzed Kneovenagel Condensation of Peptidyl Cyanomethyl Ketones with Aromatic Aldehydes and Ketones. A Novel Michael Acceptor Functionality for C–modified Peptides: The Benzylidene and Alkylidene Cyanomethyl Ketone Function", J. Org. Chem., 57:1838–1842 (1992) month not available.

Takaaki, A., et al., "Structures and activities of protease inhibitors of microbial origin", 7–Enzymes, 85:1683 (1976) month not available.

Morgan, B.A., et al., "Synthesis and pharmacology of dipeptides related to des [Gly$^3$]enkephalin: modification of the C–terminal amide", Chem. Abs. 106:650 (1987) month not available.

Boden, P.R., et al., "Rationally designed 'dipeptoid' analogues of cholecystokinin (CCK): C–terminal structure–activity relationships of α–methyl tryptophan derivatives", Eur. J. Med. Chem. 28:47–61, (1993) month not available.

Palmer, J.T., et al., "Vinyl Sulphones as Mechanism–Based Cysteine Protease Inhibitors." Journal of Medicinal Chemistry, 38(17):3193–3196 (1995) month not available.

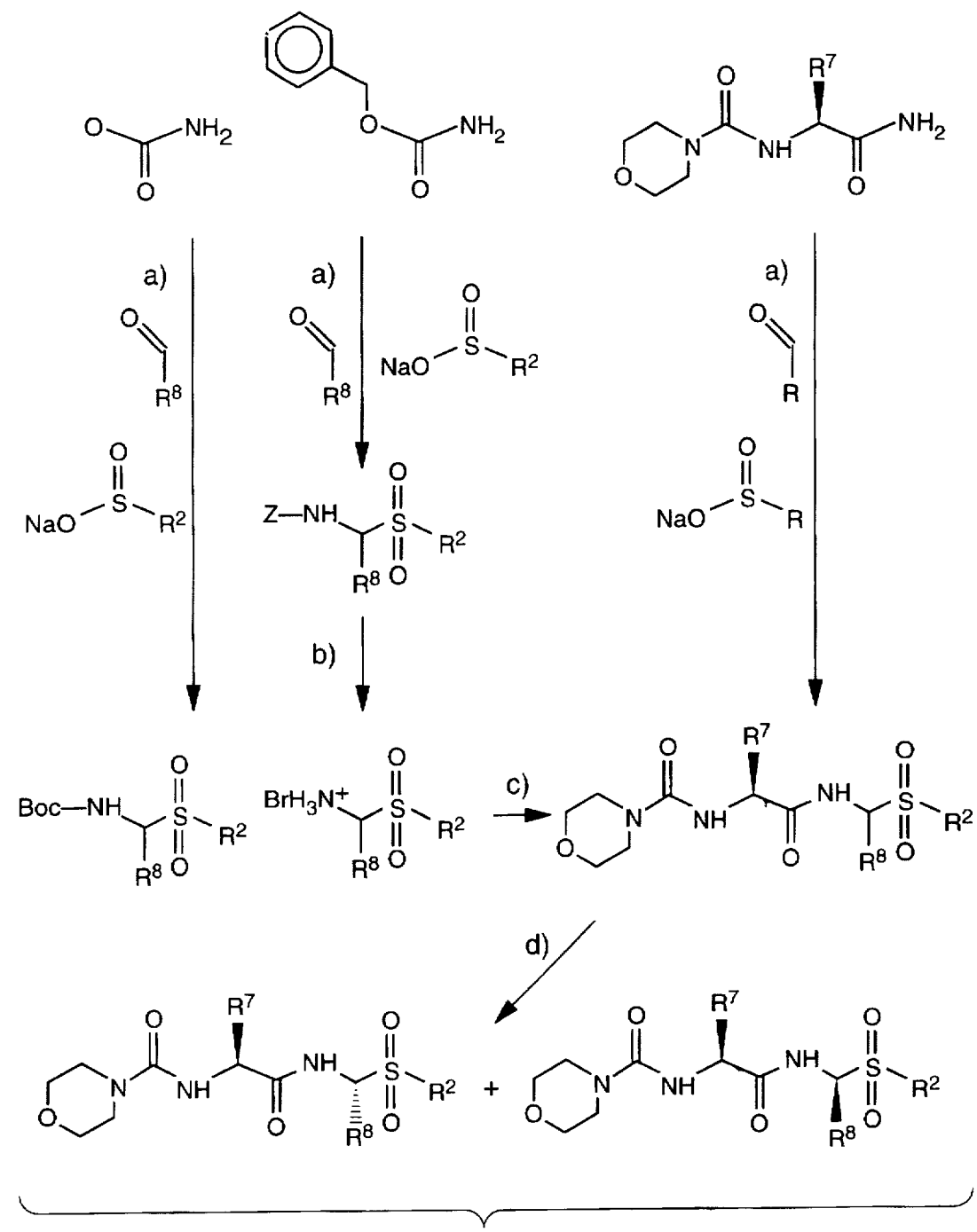
FIG._1

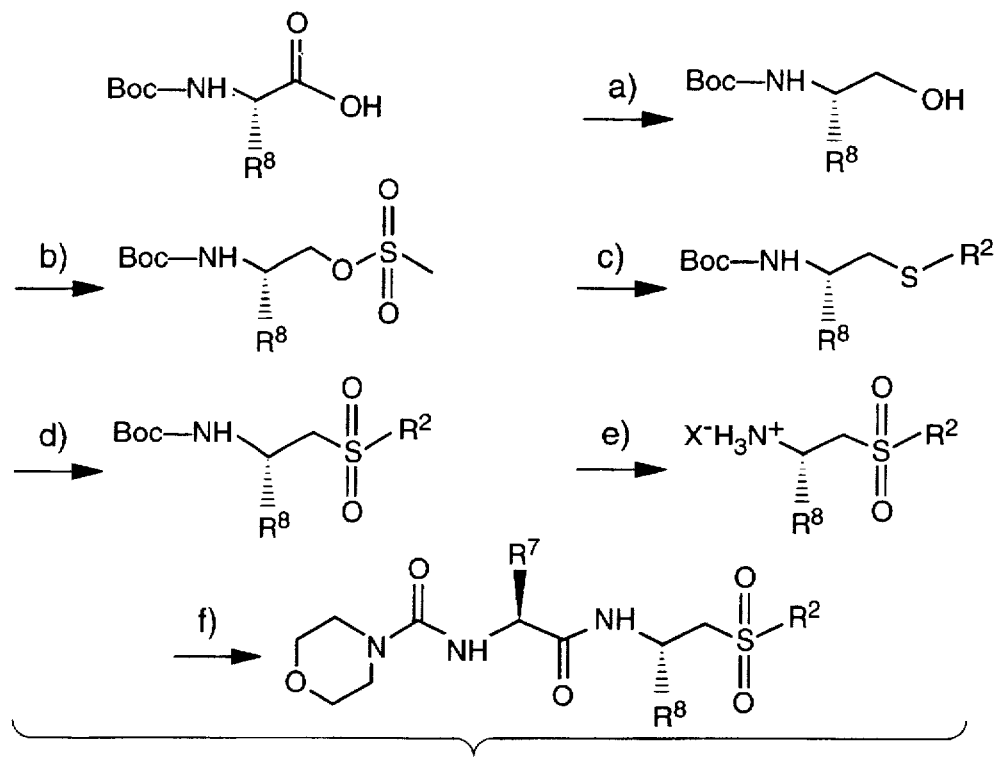
FIG._2
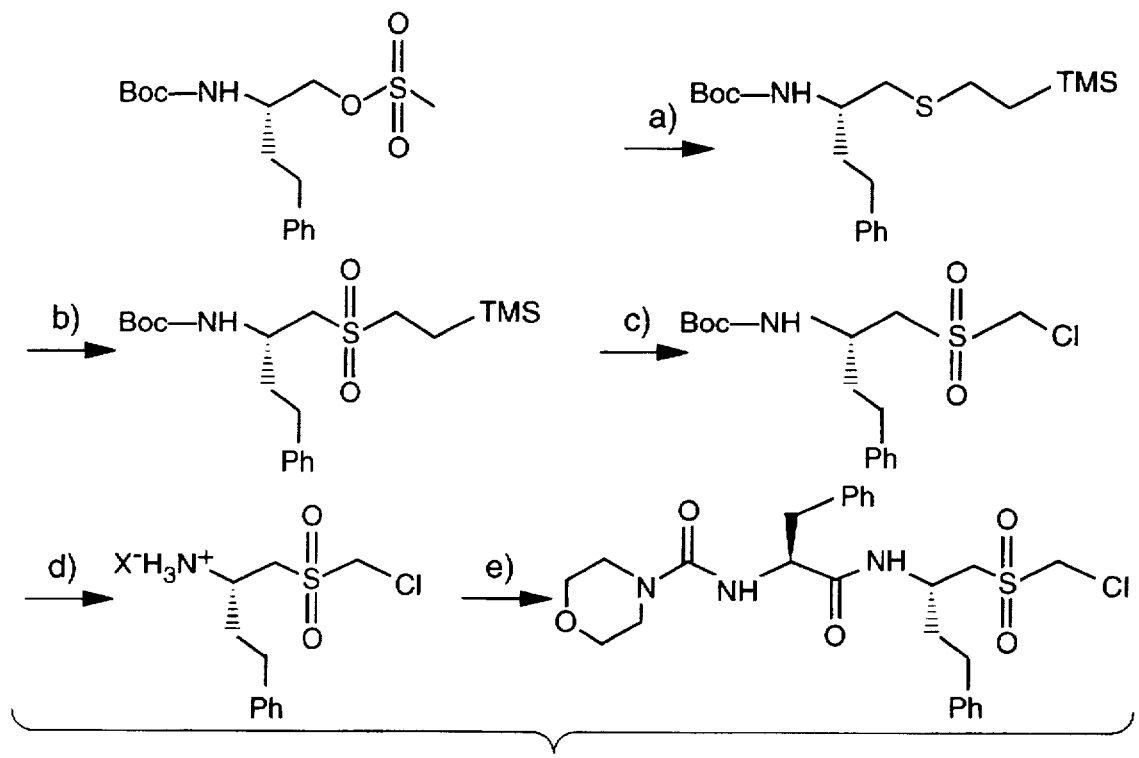
FIG._3

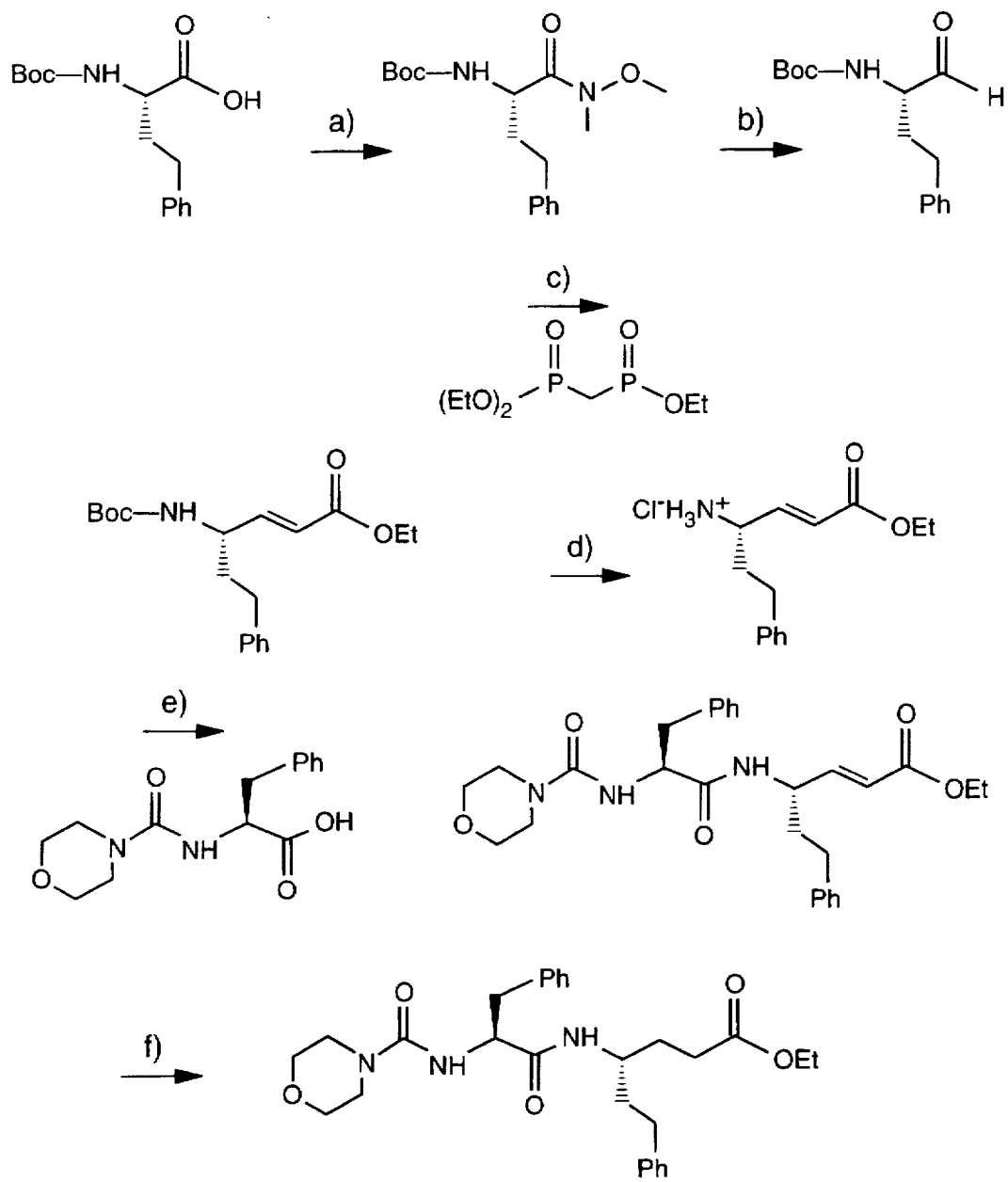
FIG._4

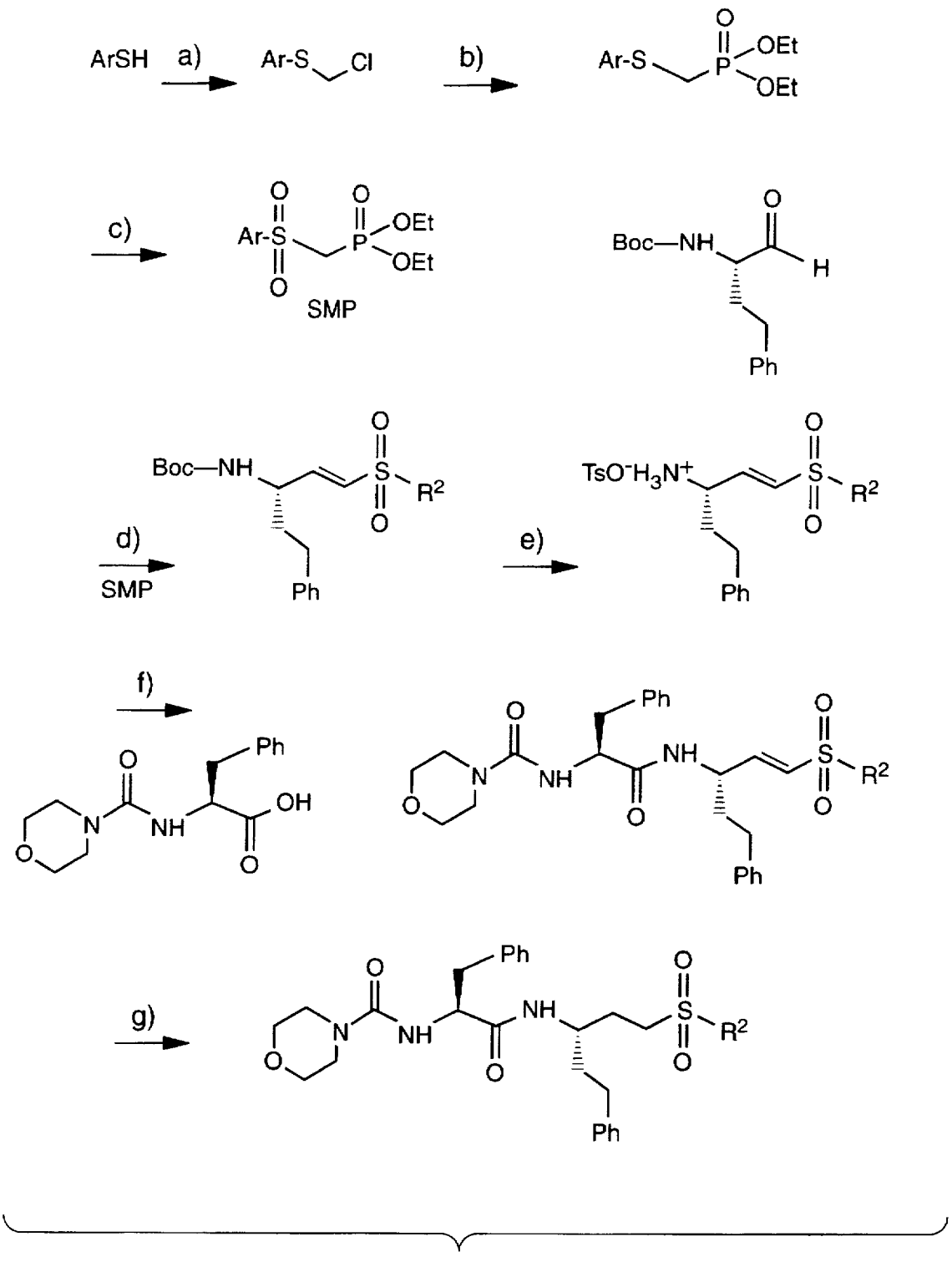
FIG._5

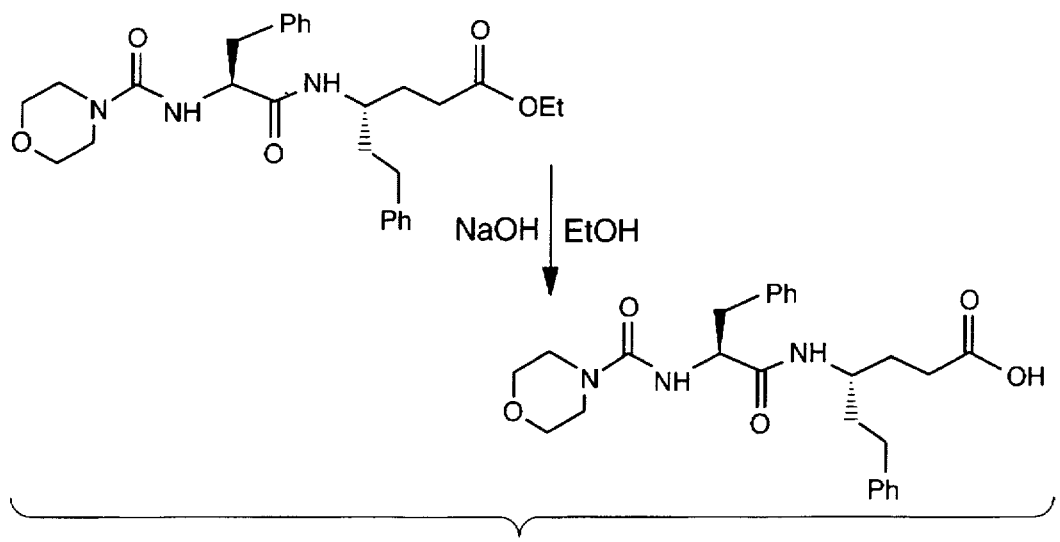
FIG._6
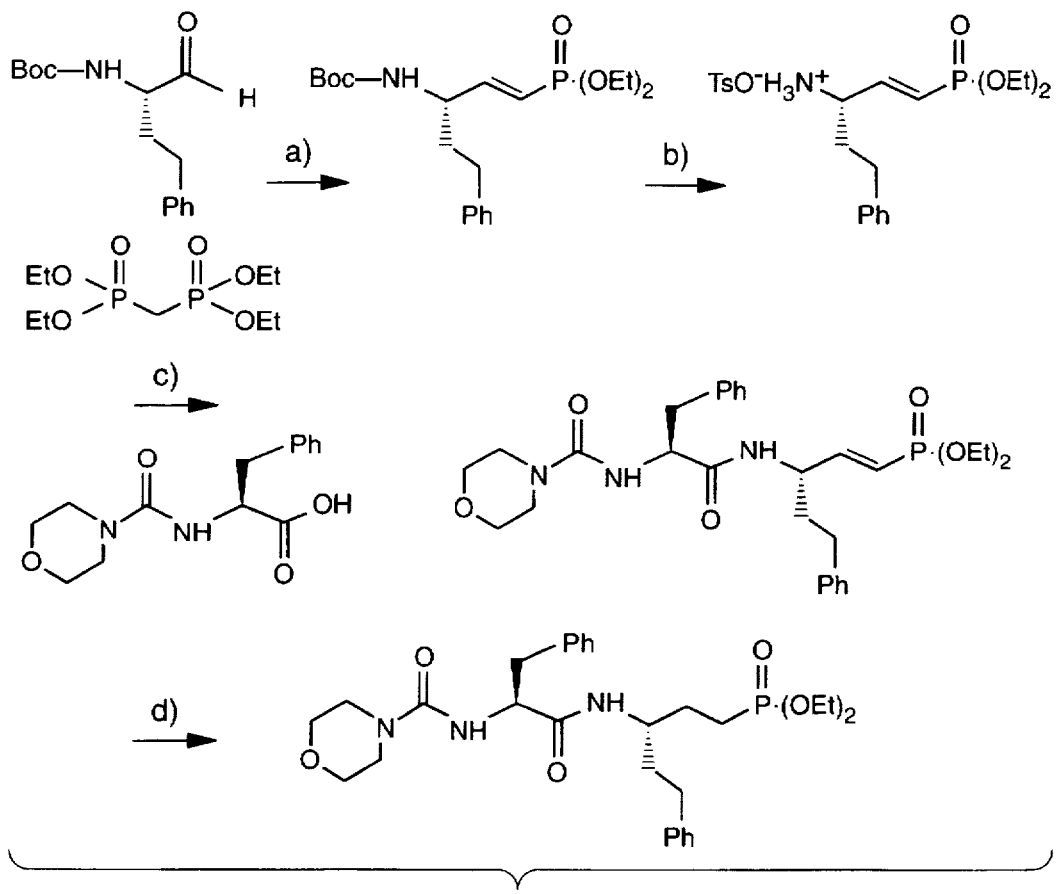
FIG._7

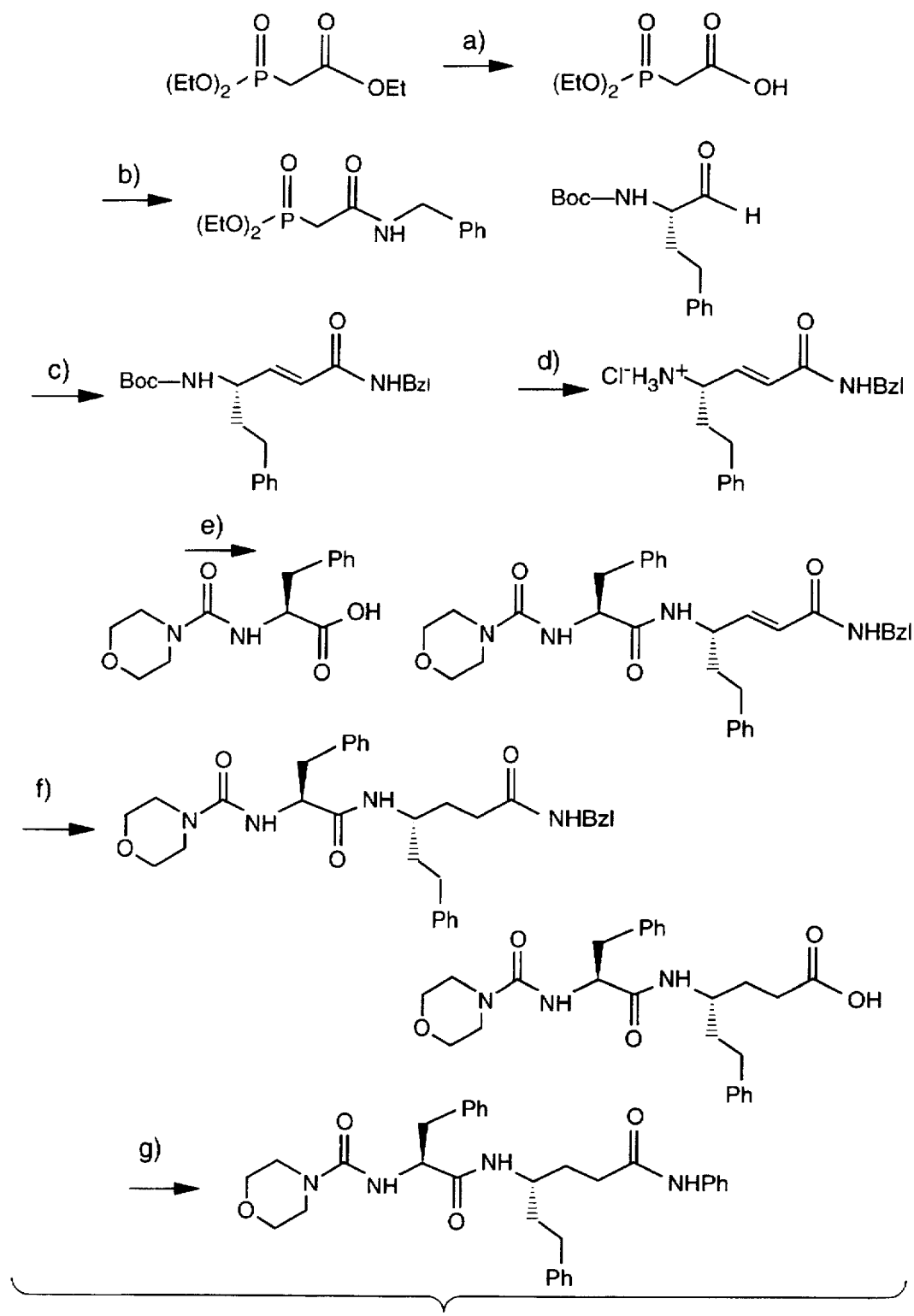
FIG._8

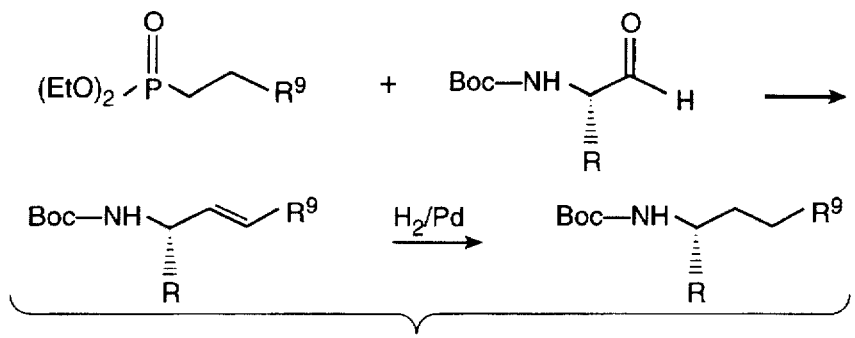
FIG._9
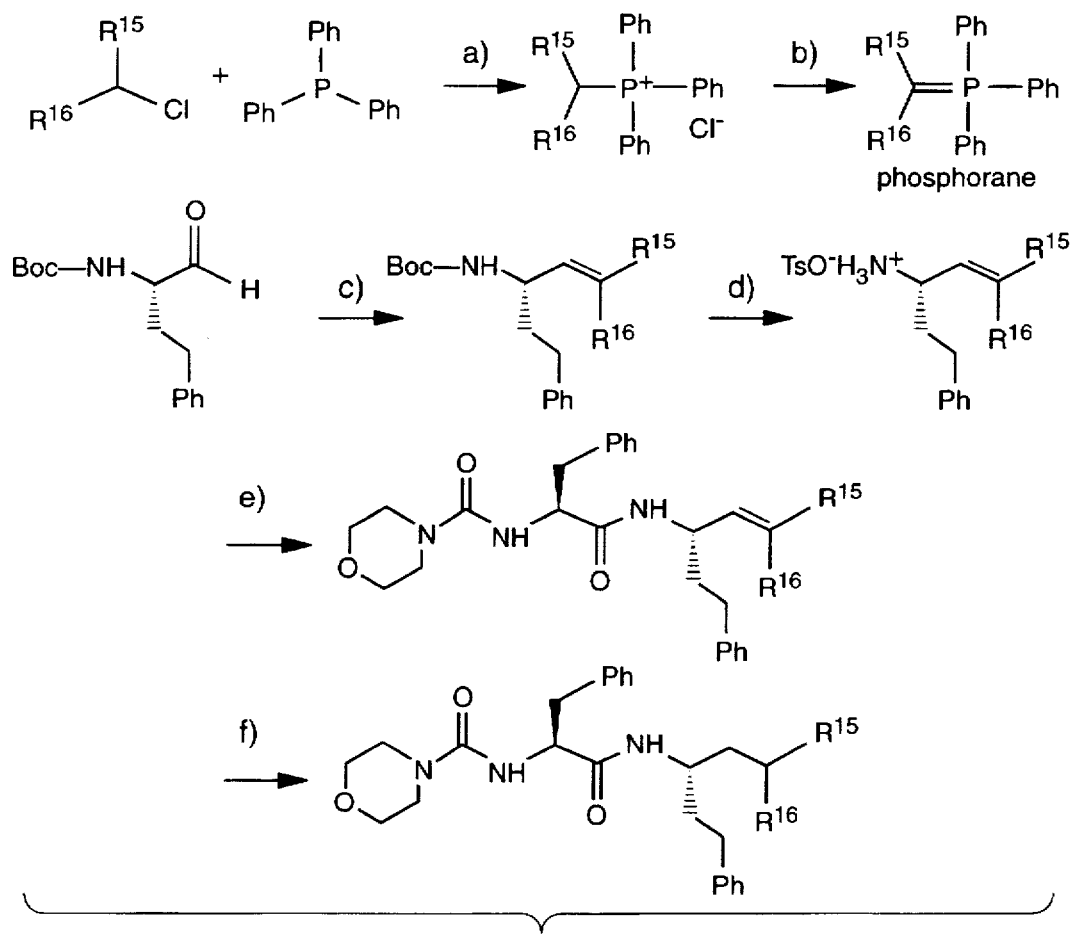
FIG._10

REVERSIBLE PROTEASE INHIBITORS

This is a continuing application of U.S. Ser. No. 08/409,996, filed Mar. 24, 1995, and of U.S. Ser. No. 08/409,553, filed Mar. 24, 1995, and of U.S. Ser. No. 08/409,997, filed Mar. 24, 1995, and of U.S. Ser. No. 08/410,000, filed Mar. 24, 1995.

FIELD OF THE INVENTION

The invention relates to novel reversible protease inhibitors. The inhibitors are selective for cysteine proteases.

BACKGROUND OF THE INVENTION

Cysteine or thiol proteases contain a cysteine residue at the active site responsible for proteolysis. Since cysteine proteases have been implicated in a number of diseases, including arthritis, muscular dystrophy, inflammation, tumor invasion, glomerulonephritis, malaria, and other parasite-borne infections, methods for selectively and irreversibly inactivating them provide opportunities for new drug candidates. See, for example, Esser, R. E. et al., Arthritis & Rheumatism (1994) 37, 236; Meijers, M. H. M. et al., Agents Actions (1993), 39 (Special Conference Issue), C219; Machleidt, W. et al, Fibrinolysis (1992), 6 Suppl. 4, 125; Sloane, B. F. et al., Biomed. Biochim. Acta (1991), 50, 549; Duffy, M. J., Clin. Exp. Metastasis (1992), 10, 145; Rosenthal, P. J., Wollish, W. S., Palmer, J. T., Rasnick, D., J. Clin. Investigations (1991), 88, 1467; Baricos, W. H. et al, Arch. Biochem. Biophys. (1991), 288, 468; Thornberry, N. A. et al., Nature (1992), 356, 768.

Low molecular weight inhibitors of cysteine proteases have been described by Rich, Proteinase Inhibitors (Chapter 4, "Inhibitors of Cysteine Proteinases"), Elsevier Science Publishers (1986). Such inhibitors include peptide aldehydes, which form hemithioacetals with the cysteine of the protease active site. See, for instance, Cheng, H., Keitz, P., and Jones, J. B., J. Org. Chem. (1994), 59, 7671. The disadvantage of aldehydes is their in vivo and chemical instabilities.

Aldehydes have been transformed into α,β-unsaturated esters and sulfones by means of the Wadsworth-Emmons-Horner modification of the Wittig reaction, shown below (Wadsworth, W. S. and Emmons, W. D. (J. Am. Chem. Soc. (1961), 83, 1733).

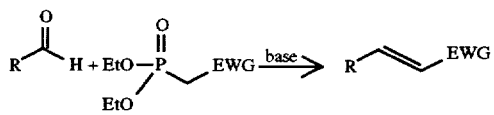

where
R=alkyl, aryl, etc.
EWG=COOEt, SO$_2$Me, etc.

α,β-unsaturated esters (Hanzlik et al., J. Med. Chem., 27(6):711–712 (1984), Thompson et al., J. Med. Chem. 29:104–111 (1986), Liu et al., J. Med. Chem., 35(6):1067 (1992)) and α,β-unsaturated sulfones (Thompson et al., supra, Liu et al., supra) were tested as inhibitors of two cysteine proteases, papain and dipeptidyl amino-peptidase I (also called cathepsin C). However, the inhibition of papain by these α,β-unsaturated compounds showed poor inhibition, evidenced by second order rate constants from less than 1M$^{-1}$ sec$^{-1}$ to less than 70M$^{-1}$ sec$^{-1}$ for the α,β-unsaturated esters, and from less than 20M$^{-1}$ sec$^{-1}$ to less than 60M$^{-1}$ sec$^{-1}$ for the sulfone.

In addition, this chemistry has not been demonstrated with derivatives of α-amino acids other than those corresponding to glycine, or in the case of the ester, phenylalanine. Thus the chirality of these compounds is non-existent for the glycine derivatives and unclear for the phenylalanine derivatives. This is significant since inhibition of an enzyme generally requires a chiral compound.

Alpha-amino sulphonic acids were suggested as potential inhibitory compounds, and several were made, although their inhibitory effects were not reported (McIlwain et al., J. Chem. Soc. 75 (1941)).

In addition, the Mannich condensation of sulfinic acid, aldehyde, and ethyl carbamate, to form urethanes has been reported (Engberts et al., Recueil 84:942 (1965).

Additional methods for selectively and irreversibly inhibiting cysteine proteases have relied upon alkylation by peptide α-fluoromethyl ketones (Rasnick, D., Anal. Biochem. (1985), 149, 416), diazomethyl-ketones (Kirschke, H., Shaw, E. Biochem. Biphys. Res. Commun. (1981), 101, 454), acyloxymethyl ketones (Krantz, A. et al., Biochemistry, (1991), 30, 4678; Krantz, A. et al., U.S. Pat. No. 5,055,451, issued Oct. 8, 1991), and ketosulfonium salts (Walker, B., Shaw, E., Fed. Proc. Fed. Am. Soc. Exp. Biol., (1985), 44, 1433).

Other families of cysteine protease inhibitors include epoxysuccinyl peptides, including E-64 and its analogs (Hanada, K. et al., Agric. Biol. Chem (1978), 42, 523; Sumiya, S. et al., Chem. Pharm. Bull. ((1992), 40, 299 Gour-Salin, B. J. et al., J. Med. Chem., (1993), 36, 720), α-dicarbonyl compounds, reviewed by Mehdi, S., Bioorganic Chemistry, (1993), 21, 249, and N-peptidyl-O-acyl hydroxamates (Bromme, D., Neumann, U., Kirschke, H., Demuth, H-U., Biochim. Biophys. Acta, (1993), 1202, 271. An additional summary of methods for reversibly and irreversibly inhibiting cysteine proteases has recently been compiled; see Shaw, E., Advances in Enzymology and Related Areas of Molecular Biology (1990), 63, 271.

SUMMARY OF THE INVENTION

An aspect of this invention is a protease inhibitor comprising a targeting group linked through a two carbon atom chain to an electron withdrawing group, wherein the dissociation constant for inhibition of the protease with said inhibitor ($K_i$) is no greater than about 100 μM.

An additional aspect of this invention is a protease inhibitor comprising a targeting group linked either directly or through a linker selected from the group consisting of an intermediate carbon atom or a two carbon atom chain to a sulfone group group, wherein the dissociation constant for inhibition of the protease with said inhibitor ($K_i$) is no greater than about 100 μM.

A further aspect of this invention is a compound, preferably a protease inhibitor, of Formula I:

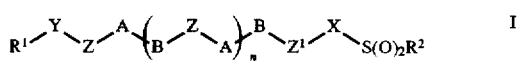

in which:

n is 0 to 13;

A-B represents a linkage selected from —C(O)NR$^3$—, —CH$_2$NR$^3$—, —C(O)CH$_2$— and —NR$^3$C(O)—, wherein R$^3$ is hydrogen or as defined below;

X represents a bond, methylene or the linkage —CH$_2$CH(R$^4$)—, wherein R$^4$ is hydrogen, alkyl or arylalkyl;

Y is —CH(R$^5$)— or —NR$^5$—, wherein R$^5$ is hydrogen or as defined below;

Z is —(CH$_2$)$_2$—, —C(R$^6$)(R$^7$)— or —N(R$^7$)—, wherein R$^6$ is hydrogen or methyl and R$^7$ is as defined below;

Z$^1$ is —(CH$_2$)$_2$—, —C(R$^6$)(R$^8$)— or —N(R$^8$)—, wherein R$^6$ is hydrogen or methyl and R$^8$ is as defined below;

R$^1$ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

R$^7$ and R$^8$ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof, cycloalkyl, cycloalkylalkyl, heteroaryl, heteroarylalkyl, a group selected from aryl and arylalkyl (which group is optionally substituted at its aryl ring with one to three radicals selected from hydroxy, amino, guanidino, halo, optionally halo-substituted alkyl, alkyloxy and aryl, or a protected derivative thereof or together with an adjacent R$^3$ or R$^5$ forms a divalent radical selected from (C$_{3-4}$)methylene and 1,2-phenylenedimethylene (which radical is optionally substituted with hydroxy, or a protected derivative thereof, or oxo); and R$^2$ is hydrogen, alkyl (optionally substituted with one or more radicals selected from amino, guanidino, halo, hydroxy, alkyloxy, nitro, alkylsulfonyl and arylsulfonyl, or a protected derivative thereof, cycloalkyl, cycloalkylalkyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof; and the pharmaceutically acceptable salts, individual isomers and mixtures of isomers thereof, preferably wherein the dissociation constant for inhibition of the protease with said inhibitor (K$_i$) is no greater than about 100 µM.

An additional aspect of this invention is a compound, preferably a protease inhibitor, of Formula II:

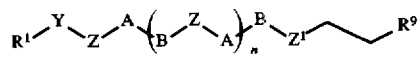   II in which:
the groups are as defined above and
R$^9$ is cyano, —C(O)OR$^{10}$, —P(O)(OR$^{10}$)$_2$, —S(O)(NR$^{10}$)R$^{10}$, C(O)R$^{11}$, —S(O)R$^{11}$, —C(O)NR$^{12}$R$^{13}$, —S(O)$_2$NR$^{12}$R$^{13}$, —C(O)NHR$^{14}$ or —S(O)$_2$NHR$^{14}$, wherein each R$^{10}$ is independently hydrogen, alkyl (optionally substituted with one or more radicals selected from amino, halo, hydroxy, alkyloxy, nitro, alkylsulfonyl and arylsulfonyl, or a protected derivative thereof, cycloalkyl, cycloalkylalkyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof), R$^{11}$ is hydrogen, alkyl, perfluoroalkyl, cycloalkyl, cycloalkylalkyl, perfluoroaryl, perfluoroarylakyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof), R$^{12}$ and R$^{13}$ are independently hydrogen, alkyl, cycloalkyl, cycloalkylalkyl, aryl or aralkyl, and R$^{14}$ is —C(O)OR$^{10}$, in which R$^{10}$ is as defined above, or a group selected from Formulae (a) and (b):

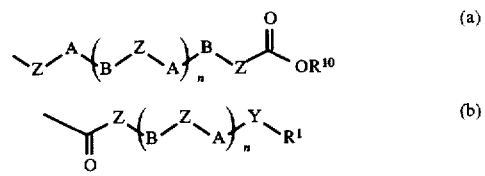

wherein each n, A, B, Y, Z, R$^1$ and R$^{10}$ are as defined above, and the pharmaceutically acceptable salts; individual isomers and mixtures of isomers thereof, preferably wherein the dissociation constant for inhibition of the protease with said inhibitor (K$_i$) is no greater than about 100 µM.

A further aspect of this invention is a compound, preferably a protease inhibitor, of Formula III:

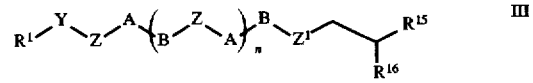   III in which:
the groups are as defined above and
R$^{15}$ is hydrogen, methyl, fluoro or a group selected from Formulae (a) and (b) as defined above, and
R$^{16}$ is a group selected from phenyl or (C$_{5-6}$)heteroaryl (which group is optionally substituted with at least one radical selected from alkylcarbamoyl, dialkylcarbamoyl, alkyloxycarbonyl, alkylsulfinamoyl, dialkylsulfinamoyl, alkylsulfonyl, carboxy, nitro, sulfinamoyl, sulfo, carbamoyl, phosphono, alkyloxyphosphinyl, dialkyloxyphosphinyl, alkanoyl, cyano, alkylsulfinyl, sulfamoyl, alkylsulfamoyl, dialkylsulfamoyl, alkyloxysulfonyl, aryl, heteroaryl, hydroxy, alkyloxy, optionally halo-substituted alkyl, arylalkyl, halo, —$^+$N(R$^{17}$)$_3$, wherein each R$^{17}$ is independently alkyl, aryl or arylalkyl, or —N(R$^{18}$)$_2$, wherein each R$^{18}$ is independently hydrogen, alkyl, aryl or arylalkyl); and the pharmaceutically acceptable salts; individual isomers and mixtures of isomers thereof, preferably wherein the dissociation constant for inhibition of the protease with said inhibitor (K$_i$) is no greater than about 100 µM.

An additional aspect of this invention is a pharmaceutical composition comprising a therapeutically effective amount of a cysteine protease inhibitor of the invention, or of an individual isomer, a mixture of isomers, or the pharmaceutically acceptable salt or salts thereof, in combination with one or more pharmaceutically acceptable excipients.

A further aspect of this invention is a method for treating a condition capable of amelioration by inhibition of a cysteine protease in an animal in need thereof, which method comprises administering to such animal a therapeutically effective amount of a cysteine protease inhibitor of the invention, or of an individual isomer, mixture of isomer, or the pharmaceutically acceptable salt or salts thereof.

Another aspect of this invention is a method for detecting a cysteine protease in a sample, which method comprises:

(a) assaying said sample for protease activity using a protease substrate;

(b) assaying for protease activity in the presence of a known concentration of cysteine protease inhibitor on the invention; and (c) calculating the difference between a) and b) to determine the protease activity due to cysteine protease.

An aspect of this invention are the processes for preparing the cysteine protease inhibitors of this invention.

BRIEF DESCRIPTION OF THE DRAWINGS

FIG. 1 depicts Scheme I, the synthesis of Formula I compounds when X is a bond. The synthetic steps are as follows: a) $HCO_2H$, $H_2O$; b) HBr/acetic acid; c) 4-methylmorpholine, isobutyl chloroformate, Mu-ROH; and d) chromatographic purification. The groups are as defined herein.

FIG. 2 depicts Scheme 2, the synthesis of Formula I compounds when X is a methylene group. The synthetic steps are as follows: a) 4-methylmorpholine, isobutyl chloroformate, followed by $NaBH_4$ reduction in water/THF; b) $CH_3SO_2Cl$, triethylamine, $CH_2Cl_2$; c) $R_1SH$, NaH, $CH_3OH$, THF, heat; d) 4-chloroperbenzoic acid, $CH_2Cl_2$; e) HCl/dioxane or $p$-$CH_3C_6H_4SO_3H$/ether; and f) Mu-ROH, 4-methylmorpholine, isobutyl chloroformate.

FIG. 3 depicts Scheme 3, the synthesis of Formula I compounds when X is a methylene group. The synthetic steps are as follows: a) $(CH_3)_3CH_2CH_2SH$, NaH, MeOH, THF, heat; b) 4-chloroperbenzoic acid; c) $(n$-$C_4H_9)_4N^+F^-$, THF, followed by $BrCH_2Cl$, heat; d) HCl/dioxane or 4—$CH_3C_6H_4SO_3H$/ether; and; e) 4-methylmorpholine, isobutyl chloroformate, Mu-PheOH.

FIG. 4 depicts Scheme 4, the synthesis of Formula II compounds. The synthetic steps are as follows: a) Cl—$H_2N$+($CH_3$)$OCH_3$, dicyclohexylcarbodiimide, $Et_3N$/$CH_2Cl_2$; b) $LiAlH_4$/THF; c) NaH/THF; d) Hcl/dioxane/$CH_2Cl_2$; e) 4-methylmorpholine, isobutyl chloroformate/THF; and f) $H_2$, 5% Pd/C.

FIG. 5 depicts Scheme 5, the synthesis of Formula I compounds when X is an ethylene. The synthetic steps are as follows: a)$(CH_2O)_n$, HCl, dioxane, for instance where Ar=2-naphthyl; b) $(EtO)_3P$; c) $CH_3CO_3H$, $CH_2Cl_2$; d) NaH, THF; e) $p$-$CH_3C_6H_4SO_3H$, $Et_2O$; f) 4-methylmorpholine, isobutyl chloroformate; and g) $H_2$, Pd/C.

FIG. 6 depicts the synthesis of compounds of Formula II in which $R^9$ is —COOH.

FIG. 7 depicts the synthesis of compounds of Formula II in which $R^9$ is —$P(O)(R^{10})_2$. The synthetic scheme is as follows: a) NaH/THF; b) anhydrous $p$-$CH_3C_6H_4SO_3H$/ether; c) 4-methylmorpholine, isobutyl chloroformate/THF, and; d) $H_2$, Pd/C.

FIG. 8 depicts the synthesis of compounds of Formula II in which $R^9$ is —C(O)NHR$^{14}$. The synthetic scheme is as follows: a) NaOH/EtOH, followed by Hcl/$H_2O$; b) benzylamine, dicyclohexylcarbodiimide, $CH_2Cl_2$; c) NaH/THF, diethyl benzylamidomethylenephosphonate; d) HCl/dioxane; e) 4-methylmorpholine, isobutyl chloroformate, THF; f) $H_2$, Pd/C, and as an alternative preparation from carboxylates as synthesized via Scheme 6, above; and g) aniline, dicyclohexylcarbodiimide, $CH_2Cl_2$.

FIG. 9 depicts the general synthesis of compounds of Formula II.

FIG. 10 depicts the synthesis of compounds of Formula III. The synthetic steps are as follows: a) $CH_3CN$ or other suitable solvent, reflux; b) $H_2O$, NaOH, followed by extraction into organic medium; c) phosphorane, THF (Wittig reaction); d) $p$-$CH_3C_6H_4SO_3H$, ether; e) Mu-PheOH, 4-methylmorpholine, isobutyl chloroformate, THF; and f) $H_2$, Pd/C.

DEFINITIONS

Unless otherwise stated, the following terms used in the specification and claims are defined for the purposes of this application and have the meanings given below:

"Alkyl", as in alkyl, alkyloxy, alkylthio, alkylsulfonyl, alkylcarbamoyl, dialkylcarbamoyl, heteroarylalkyl, arylalkyl, and the like, means a straight or branched, saturated or unsaturated hydrocarbon radical having from 1 to 10 carbon atoms or the number of carbon atoms indicated (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, etc.).

"Alkyloxyphosphinyl" and "dialkyloxyphosphinyl" mean the radicals —P(O)(OH)OR and —P(O)(OR)$_2$, respectively, wherein R is alkyl as defined above.

"Alkanoyl", as in alkanoyl, alkanoyloxy, heterocycloalkylalkanoylamino, and the like, means the radical —C(O)R, wherein R is alkyl as defined above, having overall from 1 to 11 carbon atoms or the number of carbon atoms indicated (e.g., (C$_{1-4}$)alkanoyl includes the radicals formyl, acetyl, propionyl, isopropionyl, butyryl, isobutyryl, crotonoyl, isocrotonyl, etc.).

"Aryl" means an aromatic monocyclic or polycyclic hydrocarbon radical containing 6 to 14 carbon atoms or the number of carbon atoms indicated and any carbocylic ketone or thioketone derivative thereof, wherein the carbon atom with the free valence is a member of an aromatic ring. (e.g., aryl includes phenyl, naphthyl, anthracenyl, phenanthrenyl, 1,2,3,4-tetrahydro-5-naphthyl, 1-oxo-1,2-dihydro-5-naphthyl, 1-thioxo-1,2-dihydro-5-naphthyl, etc.).

"Aroyl" means the radical —C(O)Ar, wherein Ar is aryl as defined above, having overall from 7 to 15 carbon atoms or the number of carbon atoms indicated (e.g., (C$_{7-11}$)aroyl includes benzoyl, naphthoyl, etc.).

"Cycloalkyl", as in cycloalkyl and cycloalkylalkyl, means a saturated or unsaturated, monocyclic or polycyclic hydrocarbon radical containing 3 to 20 carbon atoms or the number of carbon atoms indicated, wherein the carbon atom with the free valence is a member of a non-aromatic ring, and any carbocyclic ketone and thioketone derivative thereof (e.g., the term cycloalkyl is meant to include cyclopropyl, cyclobutyl, cyclopentyl, cyclohexyl, cyclohexenyl, bicyclo[2.2.2]octyl, 1,2,3,4-tetrahydro-1-naphthyl, oxocyclohexyl, dioxocyclohexyl, thiocyclohexyl, 9-fluorenyl, etc.).

"Halo" means fluoro, chloro, bromo or iodo.

"Heterocycloalkyl", as in heterocycloalkyl, heterocycloalkylalkanoylamino, heterocycloalkylcarbonyl, heterocycloalkylcarbonyl, and the like, means cycloalkyl as defined above wherein 1 to 5 of the indicated carbon atoms is replaced by a heteroatom chosen from N, O, S, P or As, wherein the atom with the free valence is a member of a non-aromatic ring, and any heterocyclic ketone, thioketone, sulfone or sulfoxide derivative thereof, (e.g., the term heterocycloalkyl is meant to include piperidyl, pyrrolidinyl, pyrrolinyl, imidazolidinyl, indolinyl, quinuclidinyl, morpholinyl, piperazinyl, N-methylpiperazinyl, piperadinyl, 4,4-dioxo-4-thiapiperidinyl, 1,2,3,4-tetrahydro-3-isoquinolyl, 2,4-diaza-3-oxo-7-thia-6-bicyclo[3.3.0]octyl, etc.). Thus, hetero($C_6$)cycloalkyl includes the radicals morpholinyl, piperazinyl, piperidinyl and the like.

"Heteroaryl" means an aromatic monocyclic or polycyclic hydrocarbon radical containing overall from 5 to 14 atoms or the number of atoms indicated, wherein 1 to 5 of the indicated carbon atoms are replaced by a heteroatom chosen from N, O, S, P or As, wherein the atom with the free valence is a member of an aromatic ring, and any heterocyclic ketone and thioketone derivative thereof (e.g., the term heteroaryl is meant to include thienyl, furyl, pyrrolyl, pyrimidinyl, isoxazolyl, oxaxolyl, indolyl, benzo[b]thienyl, isobenzofuranyl, purinyl, isoquinolyl, pterdinyl, pyrimidinyl, imidazolyl, pyridyl, pyrazolyl, pyrazinyl, 4-oxo-1,2-dihydro-1-naphthyl, 4-thioxo-1,2-dihydro-1-naphthyl, etc.). Thus, hetero($C_6$)aryl includes the radicals pyridyl, pyrimidinyl, and the like.

"1,2-Phenylenedimethylene" means a divalent radical of the formula —$CH_2C_6H_4CH_2$—. For example, the group $R^1$-Y-Z-A- in which Y is —$N(R^5)$, Z is —$CH(R^7)$—, A is carbonyl and $R^7$ together with $R^5$ forms "1,2-diphenylenedimethylene" means a group of following formula:

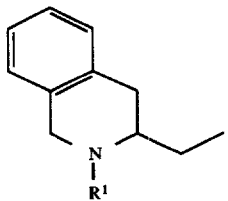

and substituted derivatives and individual stereoisomers and mixture of stereoisomers thereof. Substituted derivatives of the 1,2-phenylenedimethylene divalent radical may contain a hydroxy group on any carbon within the ring system or an oxo group on either of the unsaturated ring carbon atoms.

"Phosphono" means the radical —$P(O)(OH)_2$.

"Methylene" as in "($C_{3-4}$)methylene" and "($C_{3-7}$)methylene" mean a straight, saturated divalent radical having the number of carbon atoms indicated; "($C_{3-4}$)methylene" includes trimethylene (—$(CH_2)_3$—) and tetramethylene (—$(CH_2)_4$—). For example, a preferred embodiment herein utilizes a proline residue as an A-B-Z group, wherein A-B represents $CH_2$—NR and $R^3$ together with either $R^7$ or $R^8$ form a C3 methylene. Thus, the group $R^1$-Y-Z-A- in which Y is —$(NR^5)$—, Z is —$CH(R^7)$—, A is carbonyl and $R^7$ together with $R^5$ forms trimethylene means a group of following formula:

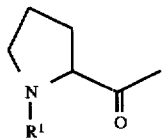

and the individual stereoisomers and mixtures of stereoisomers thereof. Substituted derivatives of the trimethylene and tetramethylene divalent radicals may contain a hydroxy group, or a protected derivative thereof, or an oxo group on any of the ring carbon atoms. Suitable hydroxy protective groups are defined below.

"Oxa($C_{3-7}$)methylene" and "aza($C_{3-7}$)methylene" mean methylene as defined above wherein one of the indicated carbon atoms is replaced by an oxygen or nitrogen atom, respectively. For example, "oxa($C_5$)methylene" includes 3-oxapentamethylene (—$CH_2CH_2OCH_2CH_2$—) and 2-oxapentamethylene (—$CH_2OCH_2CH_2CH_2$—). Thus, —$C(O)NR^{21}R^{22}$ means the radical 4-morpholinylcarbonyl when $R^{21}$ and $R^{22}$ together form 3-oxapentamethylene and the radical 1-piperazinylcarbanoyl when $R^{21}$ and $R^{22}$ together form 3-azapentamethylene.

"Adjacent", as use in the phrase "$R^7$ together with an adjacent $R^3$", means that the atoms to which the $R^7$ and $R^3$ groups are respectively attached are in turn attached to one another.

"Animal" includes humans, non-human mammals (e.g., dogs, cats, rabbits, cattle, horses, sheep, goats, swine, deer, etc.) and non-mammals (e.g., birds, etc.).

"Disease" specifically includes any unhealthy condition of an animal or part thereof and includes an unhealthy condition which may be caused by, or incident to, medical or veterinary therapy applied to that animal, i.e., the "side effects" of such therapy.

"Electron withdrawing group" (EWG) means a functional group that in its broadest sense is a group able to exert a polarizing force on the bond between itself and the carbon to which it is attached, such that electrons are polarized in favor of the electron withdrawing group. While not being limited to any particular theory, it is believed that the polarizing property enables the electron withdrawing group to participate in hydrophobic or hydrogen bonding interactions with an active site of the cysteine protease, resulting in inhibition of the enzyme. In general, a moiety is suitable as an electron withdrawing group if when present in the α-position of a phosphonium ylide of the general structure $Ph_3P=C(R)EWG$ it exerts sufficient polarization to stablize the ylide against undergoing decomposition reactions with oxygen, water, hydrohalic acids and alcohols. Preferred electron withdrawing groups are those which would similarly stablilize ylides of the general formula $(RO)_2P(O)C(R)EWG$. Suitable electron withdrawing groups include cyano, —$S(O)_2R^2$, —$C(O)OR^{10}$, —$P(O)(OR^{10})_2$, —$S(O)(NR^{10})R^{10}$, $C(O)R^{11}$, —$S(O)R^{11}$, —$C(O)NR^{12}R^3$, —$S(O)_2NR^{12}R^{13}$, —$C(O)NHR^{14}$ and ($C_{5-6}$)heteroaryl, wherein each $R^2$, $R^{10}$, $R^{11}$, $R^{12}$, $R^{13}$ and $R^{14}$ are as defined in their broadest definitions set forth in the Summary of the Invention. When the electron withdrawing group is phenyl or ($C_{5-6}$)heteroaryl the ring may be substituted with one or more meta directing groups (e.g., alkyloxycarbonyl, alkylsulfinamoyl, dialkylsulfinamoyl, alkylsulfonyl, carboxy, nitro, sulfinamoyl, sulfo, phosphono, alkyloxyphosphinyl, dialkyloxyphosphinyl, alkanoyl, cyano, alkylsulfinyl, sulfamoyl, alkylsulfamoyl, dialkylsulfamoyl, alkyloxysulfonyl, disubstituted amino, trisubstituted ammonio, and the like), ortho and para directing groups (e.g., hydroxy, alkyloxy, optionally halo-substituted alkyl, aryl, arylalkyl, halo, and the like) and electron withdrawing moieties (e.g., alkylcarbamoyl, dialkylcarbamoyl, alkyloxycarbonyl, alkylsulfinamoyl, dialkylsulfinamoyl, alkylsulfonyl, carboxy, nitro, sulfinamoyl, sulfo, carbamoyl, phosphono, alkyloxyphosphinyl, dialkyloxyphosphinyl, alkanoyl, cyano, alkylsulfinyl, sulfamoyl, alkylsulfamoyl, dialkylsulfamoyl, alkyloxysulfonyl, aryl, heteroaryl, and the like).

"Leaving group" has the meaning conventionally associated with it in synthetic organic chemistry, i.e., an atom or group displaceable under alkylating conditions, and includes halo and alkane- or arenesulfonyloxy, such as methoxy, ethanesulfonyloxy, benzenesulfonyloxy and tosyloxy, and alkanesulfonylamino, alkanecarbonylamino, aminosulfonylamino, and aminocarbonylamino.

Isomerism is the phenomenon wherein compounds have identical molecular formulae but differ in the nature or sequence of bonding of their atoms or in the arrangement of theri atoms in space. Isomers that differ in the arrangement of their atoms in space are termed "steroisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center".

A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diasteromer or as a mixture of diastereomers, termed a "diastereomeric mixture".

Compounds of Formulae I, II and III can exist as individual steroisomers or mixtures of stereoisomers. For example, compounds of Formulae I, II and III contain a chiral center at the carbon to which the substituent $R^8$ is attached. Furthermore, compounds of Formulae I, II and III in which Z is —$C(R^6)(R^7)$ contain a chiral center at the carbon to which the $R^7$ substituent is attached. Thus, for example, compounds of Formulae I, II and III in which n is 0 and Z is —$C(R^6)(R^7)$ will have two chiral centers and can exist as four individual stereoisomers or any mixture thereof.

Individual stereoisomer may be characterized by the absolute configuration of their chiral centers. Absolute configuration refers to the arrangement in space of the substituents attached to the chiral center. The substituents attached to the chiral center under consideration are ranked in accordance with the Sequence Rule of Cahn, Ingold and Prelog and then the absolute descriptor R is assigned if the three highest ranked substituents are arranged in space (with the fourth lowest ranked substituent directed away from the observer) from high to low priority in a clockwise sequence and the absolute descriptor S is assigned for a counterclockwise arrangement. When an individual stereoisomer containing one chiral center is described the absolute descriptor R or S is cited in parenthesis followed by a hyphen and the chemical name of the compound. For the purposes of this invention, when an individual stereoisomer or mixture of stereoisomers containing two or more chiral centers is described, the absolute descriptor R or S is cited immediately after the appropriate locant. Acyl radicals derived from naturally occurring amino acids are referred to as their amino acid radicals preceded by the descriptor L (e.g., L-phenylalanine). The nonnatural enantiomers of amino acid acyl radicals are preceded by the descriptor D. Preferably, the amino acid side chains are the (S) or L-form, due to the stereospecificity of enzymes, although the D-forms may be used in some cases. When no absolute descriptor is cited for a chiral center, the description is meant to include both configurations and mixtures thereof, racemic or otherwise. Thus, for example, a compound of the following formula:

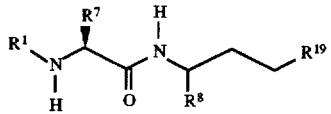

is named:

$N^2$-(4-morpholinylcarbonyl)-$N^1$-[3-phenyl-1S-(2-phenylsulfonylethyl)propyl]-L-phenylalaninamide, when $R^1$ is 4-morpholinylcarbonyl, $R^8$ is 2-phenylethyl and lies on the same side of the reference plane as the $R^7$ substituent, $R^7$ is benzyl and $R^{19}$ is phenylsulfonyl;

$N^2$-4-morpholinylcarbonyl-$N^1$-[3-phenyl-1-(2-phenylsulfonylethyl)propyl]-L-phenylalaninamide, when $R^1$ is 4-morpholinylcarbonyl, $R^8$ is 2-phenylethyl and lies on either or both sides of the reference plane. $R^7$ is benzyl and $R^{19}$ is phenylsulfonyl;

$N^2$-4-morpholinylcarbonyl-N-[3-phenyl-1 S-(2-phenylsulfonylethyl)propyl]-β-(2-naphthyl)-L-alaninamide, when $R^1$ is 4-morpholinylcarbonyl, $R^8$ is 2-phenylethyl lies on the same side of the reference plane as the $R^7$ substituent, $R^7$ is 2-naphthylmethyl and $R^{19}$ is phenylsulfonyl and ethyl 4S-(N-4-morpholinylcarbonyl-L-phenylalanylamino)-6-phenylhexanoate, when $R^1$ is 4-morpholinylcarbonyl, $R^8$ is 2-phenylethyl and lies on the same side of the reference plane as the $R^7$ substituent, $R^7$ is benzyl and $R^{19}$ is ethoxycarbonyl.

In a preferred embodiment, the compositions of the invention are pure diasteromers. Alternatively, the compositions contain mixtures of diasteromers. Preferred embodiments have greater than about 70% of a single disasteromer, with at least about 90% being particularly preferred.

"Protective group" has the meaning conventially associated with it in synthetic organic chemistry, i.e., a group which blocks a reactive site in a compound. See for example Greene et al., Protective Groups in Organic Synthesis, 2nd Ed., John Wiley & Sons, 1991, hereby incorporated by reference. Examples of hydroxy protective groups include heterocycloalkyl-carbonyl such as 4-morpholinylcarbonyl and the like, aroyl such as benzoyl and arylalkyl such as benzyl and the like. Examples of amino protective groups include aryloxycarbonyl such as benzyloxycarbonyl and the like, aroyl such as benzoyl and the like and oxycarbonyl such as ethoxycarbonyl and 9-fluorenylmethoxycarbonyl and the like. Examples of guanidino protective groups include sulfonyl such as 2,3,5-trimethyl-4-methoxyphenylsulfonyl and the like. Examples of suitable carboxy protective groups that form ester moieties are alkoxylcarbonyl of overall 4 to 8 carbon atoms, particularly tert-butoxycarbonyl (BOC) or benzyloxycarbonyl (CBZ, Z), especially cycloalkylaminocarbonyl or oxacycloalkylaminocarbonyl of overal 4 to 8 atoms in the ring, particularly 4-morpholinecarbonyl (Mu) and the like.

"Protected" in reference to a compound of a group means a derivative of a compound or group in which a reactive site or sites are blocked with protective groups .

"Optional" or "optionally" means that the subsequently described event or circumstance may or may not occur, and that the description includes instances wherein the event or circumstance occurs and instances in which it does not. For example, "optionally further substituted with one or more functional groups" means that the substituents may or may not be present in order for the compound described to fall within the invention, and the invention includes those compounds wherein on e or more functional groups are present and those compounds in which no functional groups are present.

By "cysteine protease-associated disorders" herein is meant pathological conditions associated with cysteine proteases. In some disorders, the condition is associated wtih increased levels of cysteine proteases; for example, arthritis, muscular distrophy, inflammation, tumor invasion, and glomerulonephritis are all associated with increased levels of cysteine proteases. In other disorders or diseases, the condition is associated with the appearance of an extracellular cysteine protease activity that is not present in normal tissue. In other embodiments, a cysteine protease is associated with the ability of a pathogen, such as a virus, to infect or replicate in the host organism.

Specific examples of cysteine protease associated disorders include, but are not limited to, arthritis, muscular distrophy, inflammation, tumor invasion, glomerulonephritits, malaria, Alzheimer's disease, cancer metastasis, trauma, inflammation, gingivitis, leishmaniasis, filariasis, and other bacterial and parasite-borne infections. In particular, disorders associated with interleukin 1β converting enzyme (ICE) are included.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic aicd, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptabale inorganic bases include sodium hydroxide, sodium carbonate, potassium hydroxide, aluminum hydroxide and calcium hydoxide. Acceptable organic bases include ethanolamine, diethanolamine, triethanolamine, tromethamine, N-methylglucamine and the like.

"Therapeutically effective amount" means that amount which, when administered to an animal for treating a disease includes:

(1) preventing the disease from occurring in an animal which may be predisposed to the disease but does not yet experience or display symptoms of the disease, (2) inhibiting the disease, i.e., arresting its development, or (3) ameliorate the disease, i.e., causing regression of the disease.

DETAILED DESCRIPTION OF THE INVENTION

The present invention relates to novel cysteine protease inhibitors. Without being bound by theory, it is believed that the inhibitors bind to cysteine proteases based on the following scheme.

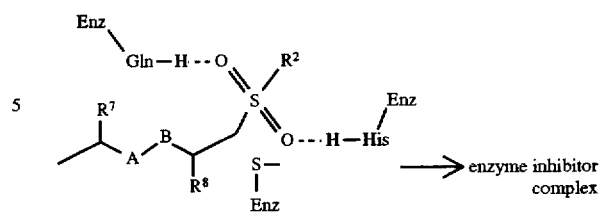

It is believed that the enzyme is thus reversibly inhibited by means of interactions between the R, Y and Z moieties of the inhibitor and the surface of the binding sites of the enzyme, and by means of hydrogen bonding interactions between the sulfone and active site amino acid side chains.

This mechanism of reversible inhibition permits specificity of the enzyme inhibitors for cysteine proteases. Generally, the inhibitors of the present invention inhibit cysteine proteases and do not inhibit serine, aspartyl, and zinc proteases. However, in some embodiments, the protease inhibitors of the present invention may have activity against other types of proteases, such as serine, aspartyl or other metalloproteases, but to a lesser extent.

In addition, the electron withdrawing properties of the sulfone group of Formula I polarize the electrons between the sulfone group and the carbon to which it is attached, thus permitting hydrogen bonding between itself and active site residues of a cysteine protease, to allow tight binding between the inhibitor and the cysteine protease, as is generally described below. It is to be understood that there is presumably additional electron withdrawing or electron polarization occurring between the sulfur atom and the oxygen atoms, which allows the oxygen atoms to participate in hydrogen bonding with active site residues of the protease and thus contributing even further to the inhibition of the enzyme.

The present invention generally provides new peptide-based and peptidomimetic cysteine protease inhibitors for use as reversible cysteine protease inhibitors. By "cysteine protease inhibitor" herein is meant an inhibitor which inhibits cysteine proteases. In a preferred embodiment, the cysteine protease inhibitors are specific to cysteine proteases; that is, they do not inhibit other types of protease such as serine, aspartyl, or other metalloproteases. However, in alternative embodiments, the cysteine protease inhibitors of the invention may inhibit other types of proteases as well.

By "reversible" herein is meant that the inhibitor binds non-covalently to the enzyme, and is to be distinguished from irreversible inhibition. See Walsh, Enzymatic Reaction Mechanisms, Freeman & Co., N.Y., 1979. "Reversible" in this context is a term understood by those skilled in the art. In addition, the reversible cysteine protease inhibitors are competitive inhibitors, that is, they compete with substrate in binding reversibly to the enzyme, with the binding of inhibitor and substrate being mutually exclusive. In addition, the stoichiometry of inhibition is 1:1; that is, a single inhibitor molecule is sufficient to inhibit a single enzyme molecule.

The cysteine protease inhibitors herein are designed to bind reversibly to cysteine proteases. This binding is accomplished by using peptide-based or peptidomimetic structures as targeting groups that mimic naturally occurring substrates and/or inhibitors. "Peptidomimetic", for the purposes of this invention, means amino acid or peptide-like in structure but wherein one or more of the peptide linkages (i.e., —C(O)NR—) is substituted by an isosteric form, i.e. —CH₂NR—, —C(O)CH$_2$— or —NRC(O)— and/or wherein non-naturally occurring amino acid substituents are present.

"Targeting group", for the purposes of this application, means a peptide or peptidomimetic residue of the cysteine protease inhibitor that allows the binding of the inhibitor to a cysteine protease. In a preferred embodiment, the targeting group of a cysteine protease inhibitor comprises at least two amino acid side chains or side chain analogs, linked via a peptide bond or isostere. The targeting group may comprise up to about 15 amino acids or analogs, although inhibitors are generally from about 1 to 7 amino acids or analogs, since smaller inhibitors are usually desired in therapeutic applications. Thus, in Formulae I, II and III, n is preferably from 0 to 13, with from 0 to 5 being preferred, and from 0 to 3 being particularly preferred.

As depicted in Formulae I, II and III, the targeting group can be represented by a naturally or non-naturally occurring peptide residue of the following formula:

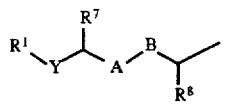

wherein the R$^8$ and R$^7$ components represent naturally or non-naturally occurring amino acid analogs or substituents as is more fully described below. The targeting group of the inhibitor may also contain additional functional groups, as depicted by R$^1$ and described herein.

While not being limited to any particular theory, it is believed that the amino acid substituents of the targeting group interact with the surface binding sites of the protease to promote binding. It is also believed that the amino acid substituent proximal to the electron withdrawing group (e.g., R$^8$ of the above formula) will occupy the S$_1$ position of the substrate binding site and therefore is designated the P$_1$ residue of the inhibitor. Similarly, the next adjacent amino acid substituent (e.g., R$^7$ of the above formula) will occupy the S$_2$ position of the substrate binding site and is designated the P2 residue of the inhibitor. If present, additional amino acid substituents will occupy the S$_3$, S$_4$, etc. positions of the substrate binding site and be designated as the P$_3$, P$_4$, etc. residues of the inhibitor. An additional targeting group may be attached to the electron withdrawing group and, if present, its amino acid substituents will occupy the S$_1$', S$_2$', etc. positions of the substrate binding sites and are designated the P$_3$', P$_4$', etc. residues of the inhibitor, respectively.

In general, targeting groups for specific enzymes are determined by rules governing substrate specificity in cysteine proteases (e.g., see "Proteinase Inhibitors", in Research Monographs in Cell and tissue Physiology (1986), ed. Barret et al., Vol 12, Chapter 4: Inhibitors of Cysteine Proteinases, Daniel Rich, Elsevier, New York; and Thornberry et al., supra., hereby expressly incorporated by reference). For example, interleukin-1 converting enzyme (ICE) accepts an aspartic acid substituent (i.e., 2-carboxyethyl) at the P$_1$ position and an alanine (methyl), valine (isopropyl) or histidine (4-imidazolylmethyl) substituent at the P2 position. Papain accepts a arginine, lysine, N-benzyloxycarbonyllysine (i.e. 4-benzyloxycarbonylaminobutyl), homophenylalanine (i.e. 2-phenylethyl), Guanidino-phenylalnine (i.e., 4-guanidinobenzyl) or norluecine (i.e., butyl) substitutents at the P$_1$ position and phenylalnine, tyrosine, β-)2-naphthyl) alanine (i.e., 2-naphthyl), leucine, norleucine, isoleucine or alanine substituents at the P$_2$ position. Cathepsin B accepts a arginine, lysine, N-benzyloxycarbonyllysine, guanidino-phenylalanine, homophenylalanine or norleucine substituents at the P$_1$ position and phenylalanine, tyrosine, 3,5-duodotyrosine (i.e., 3,5-diiodo-4-hydroxybenzyl), β-(2-naphthyl)alanine, arginine, guanidino-phenylalanine or citrumline (i.e., 3-ureidopropyl) substituents at the P$_2$ position. Cathepsin L and cruzain accept arginine, lysine, homophenylalanine, guanindinophenylalanine, citrumline or norleucine substituents at the P$_1$ position and phenylalanine, tyrosine or β-(2-naphthyl)alanine substituents at the P$_2$ position. Cathepsin S accepts a arginine, lysine, homophenylalanine, guanidino-phenylalanine, citrulline or norleucine substituents at the P$_1$ position and phenylalanine, tyrosine, β-(2-naphthyl)anine, valine, leucine, norleucine, isoleucine or alanine substituents at the P$_2$ position. DPP-1 accepts phenylalanine or tyrosine substituents at the P$_1$ position and no subsutituent or alanine at the P$_2$ position. Calpain accepts phenylalanine, tyrosine, methionine, β-methylsulfonylmethylalanine (i.e., 2-methylsulfonylethyl) or valine substituent at the P$_1$ position and valine, leucine, norleucine or isoleucine substituents at the P$_2$ position.

Thus, R$^7$and R$^8$ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof, cycloalkyl, cycloalkylalkyl, heteroayl, heteroaylalkyl, a group selected from aryl and arylalkyl (which group is optionally substituted at its aryl ring with one to three radicals selected from hydroxy, amino, guanidino, halo, optionally halo-substituted alkyl, alkyloxy and aryl, or a protected derivative thereof or together with an adjacent R$^3$ or R$^5$ forms a divalent radical selected from (C$_{3-4}$)methylene and 1,2-phenylenedimethylene (which radical is optionally substituted with hydroxy, or a protected derivative thereof, or oxo).

Accordingly, preferred R$^7$ and R$^8$ groups are the naturally occuring amino acid side chains and homologous derivatives. These include, but are not limited to, alanine (methyl), arginine (3-guanidinopropyl), asparagine (carbamoylmethyl), citurlline (3-ureidopropyl), aspartic acid (carboxymethyl), cysteine (mercaptomethyl), glutamic acid (2-carboxyethyl), glutamine (2-carbamoylethyl), glycine (hydrogen), histidine (4-imidazolyl methyl), homophenylalanine (2-phenylethyl), homoserine (2-hydroxylethyl), isoleucine ((1-methylpropyl), leucine (isobutyl), lysine (4-aminobutyl), methionine (2-methylthioethyl), β-(1-naphthyl)alanine (1-napthylmethyl), β-(2-naphthyl)alanine (2-napthylmethyl), norleucine (butyl), norvaline (propyl), ornithine (3-aminopropyl), phenylalanine (benzyl), proline (as described herein), sarcosine (methylaminomethyl), serine (hydroxymethyl), threonine (1-hydroxyethyl), tryptophan (3-indolymethyl), tyrosine (4-hydroxybenzyl), and valine (isopropyl).

While the broadest definition of this invention is set forth in the Summary of the Invention, certain compounds of the invention are preferred. For example, generally preferred compounds of Formulae I, II and III are those in which n is 0 to 5; A-B represents a linkage selected from —C(O) NR$^3$—, wherein R$^3$ is hydrogen or as defined below; Y is —N(R$^5$)—, wherein R$^5$ is hydrogen or as defined below; Z is —(CH$_2$)$_2$— or —C(R$^6$)(R$^7$)—; Z$^1$ is —CH(R$^5$)—; R$^1$ is hydrogen, alkyloxycarbonyl of overall 3 to 10 carbon atoms, (C$_{1-9}$)alkoxycarbonyl, (C$_{2-10}$)alkanoyl (optionally substituted with a radical selected from carboxy, (C$_{1-9}$)alkyloxycarbonyl and hetero(C$_{4-8}$)cycloalkyl(C$_{2-10}$) alkanoylamino), (C$_{4-9}$)cycloalkylcarbonyl, hetero(C$_{4-8}$) cycloalkylcarbonyl (optionally substituted with a radical selected from hydroxy, $(C_{1-5})$alkyl, $(C_{1-5})$alkanoyl, $(C_{1-5})$ alkyloxycarbonyl, $(C_{6-10})$aryl$(C_{1-5})$alkyloxycarbonyl and hetero$(C_{4-8})$cycloalkylcarbonyl), $(C_{6-10})$aryl$(C_{1-5})$ alkyloxycarbonyl, carbamoyl, $(C_{1-5})$alkylcarbamoyl, di$(C_{15})$alkylcarbamoyl, $(C_{6-10})$arylcarbamoyl, $(C_{6-10})$aryl $(C_{1-5})$alkylcarbamoyl, $(C_{6-10})$aryl$(C_{1-5})$alkanoyl, $(C_{7-11})$ aroyl, $(C_{1-5})$alkylsulfonyl, di$(C_{1-5})$alkylaminosulfonyl, $(C_{6-10})$arylsulfonyl or hetero$(C_{5-8})$arylsulfonyl; and $R^7$ and $R^8$ are independently $(C_{1-5})$alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof), $(C_{3-7})$cycloalkyl, $(C_{3-7})$cycloalkyl$(C_{1-6})$alkyl, pyridyl, thienyl, furyl, imidazolyl, indolyl, pyridyl$(C_{1-6})$alkyl, thienyl$(C_{1-6})$ alkyl, furyl$(C_{1-6})$alkyl, imidazolyl$(C_{1-6})$alkyl, indolyl$(C_{1-6})$ alkyl, a group selected from or a group selected from phenyl, naphthyl, phenyl$(C_{1-6})$alkyl, naphthyl$(C_{1-6})$alkyl, (which group is optionally substituted at its aryl ring with one to three radicals selected from hydroxy, amino, chloro, bromo, iodo, fluoro, methyl, trifluoromethyl, methoxy and phenyl, or a protected derivative thereof) or together with an adjacent $R^3$ or $R^4$ forms a divalent radical selected from $(C_{3-4})$ methylene and 1,2-phenylenedimethylene (which radical is optionally substituted with hydroxy, or a protected derivative thereof, or oxo).

More preferred compounds of Formulae I, II and III are those in which n is 0 to 2; A-B represents a linkage selected from —C(O)NR$^3$—, wherein $R^3$ is hydrogen or as defined below; Y is —N(R$^5$)—, wherein $R^5$ is hydrogen or as defined below; Z is —(CH$_2$)$_2$— or —C(R$^6$)(R$^7$)— (with the proviso that when n is 0, Z is not —(CH$_2$)$_2$—); $Z^1$ is —CH(R$^8$)—; $R^1$ is hydrogen, $(C_{4-8})$alkoxycarbonyl, $(C_{2-6})$ alkanoyl (optionally substituted with a radical selected from carboxy, $(C_{1-5})$alkyloxycarbonyl and hetero$(C_{4-8})$cycloalkyl $(C_{4-6})$ alkanoylamino), —C(O)NR$^{21}$R$^{22}$ wherein $R^{21}$ and $R^{22}$ together form aza$(C_{2-6})$methylene, oxa$(C_{2-6})$methylene or $(C_{3-7})$methylene, $(C_{4-8})$cycloalkylcarbonyl, benzyloxycarbonyl, acetyl, benzoyl or dimethylaminosulfonyl; and $R^8$ and $R^7$ are independently $(C_{5-6})$cycloalkyl, $(C_{5-6})$cycloalkylmethyl, 3-pyridyl, 2-thienyl, 2-furyl, 4-imidazolyl, 3-indolyl, 3-pyridylmethyl, 2-thienylmethyl, 2-furylmethyl,4-imidazolylmethyl, 3-indolylmethyl, $(C_{1-5})$ alkyl (optionally substituted with a radical selected from mercapto, carboxy, amino, methylthio, methylsulfonyl, carbamoyl, dimethylcarbamoyl, guanidino and hydroxy, or a protected derivative thereof), a group selected from phenyl, 1-naphthyl, 2-naphthyl, benzyl, 1-naphthylmethyl, 2-naphthylmethyl and 2-phenylethyl (which group is optionally substituted at its aryl ring with one radical selected from hydroxy, amino, chloro, bromo and fluoro, or a protected form thereof or together with an adjacent $R^3$ or $R^5$ forms a divalent radical selected from $(C_{3-4})$methylene and 1,2-phenylenedimethylene (which radical is optionally substituted with hydroxy, or a protected derivative thereof, or oxo).

Particularly preferred compounds of Formulae I, II and III are those in which n is 0 to 1; A-B represents a linkage selected from —C(O)NR$^3$—; Y is —N(R$^5$)—, wherein $R^5$ is hydrogen or as defined below; Z is —C(R$^6$)(R$^7$)—; $Z^1$ is —CH(R$^5$)—; $R^1$ is hydrogen, tert-butoxycarbonyl, benzyloxycarbonyl, acetyl, 3-carboxypropionyl, 3-methoxycarbonylpropionyl, biotinylaminohexanoyl, phenylacetyl, benzoyl, dimethylaminosulfonyl, benzylsulfonyl, 1-piperazinylcarbonyl, 4-methylpiperazin-1-ylcarbonyl or 4-morpholinylcarbonyl; $R^7$ is 3-pyridylmethyl, 2-thienylmethyl, 2-furylmethyl, 4-imidazolylmethyl, 3-indolylmethyl, $(C_{1-5})$alkyl (optionally substituted with a radical selected from mercapto, carboxy, amino, methylthio, methylsulfonyl, carbamoyl, dimethylcarbamoyl, guanidino and hydroxy, or a protected derivative thereof, a group selected from benzyl, 1-naphthylmethyl, 2-naphthylmethyl and 2-phenylethyl (which group is optionally substituted at its aryl ring with one radical selected from hydroxy, amino, chloro, bromo and fluoro, or a protected form thereof) or together with an adjacent $R^3$ or $R^5$ forms a divalent radical selected from $(C_{3-4})$methylene and 1,2-phenylenedimethylene (which radical is optionally substituted with hydroxy, or a protected derivative thereof, or oxo); and $R^8$ is butyl, 2-phenylethyl, 2-methylsulfonylethyl, 2-tert-butoxycarbonylethyl, 2-tert-butoxycarbonylmethyl, 4-tert-butoxycarbonylaminobutyl, 4-benzoylaminobutyl or benzyloxymethyl. More particularly preferred compounds of Formulae I, II and III are those in which n is 0; A-B represents a linkage selected from —C(O)NH—; Y is —NH—; Z is —CH(R$^7$)—; $Z^1$ is —CH (R$^3$)—; $R^1$ is hydrogen, tert-butxoycarbonyl, benzyloxycarbonyl, biotinylaminohexanoyl, benzoyl, piperizin-1-ylcarbonyl, 4-methylpiperazin-1-ylcarbonyl or 4-morpholinylcarbonyl; $R^7$ is $(C_{1-5})$alkyl, optionally substituted benzyl, 1-naphthylmethyl, 2-naphthylmethyl, 3-pyridinylmethyl or 2-methylsulfonylethyl; and $R^8$ is butyl, 2-phenylethyl or 2-methylsulfonylethyl.

Most preferred compounds of Formula I, II and III are those in which n is 0; A-B represents a linkage selected from —C(O)NH—; Y is —NH—; Z is —CH(R$^7$)—; $Z^1$ is —CH (R$^8$)—; $R^1$ is 1-piperizinylcarbonyl, 4-methyl-1-piperazinylcarbonyl or 4-morpholinylcarbonyl; $R^7$ is optionally substituted benzyl, 1-naphthylmethyl or 2-naphthylmethyl; and $R^8$ is 2-phenylethyl.

Generally preferred compounds of Formula I are those in which $R^2$ is independently $(C_{1-5})$alkyl (optionally substituted with one or two radicals selected from amino, chloro, bromo, fluoro, hydroxy and methoxy, or a protected derivative thereof, perhalo$(C_{1-5})$alkyl, $(C_{3-7})$cycloalkyl, $(C_{3-7})$ cycloalkyl$(C_{1-5})$alkyl or a group selected from phenyl, pentafluorophenyl, naphthyl and phenyl$(C_{1-6})$alkyl (which group is optionally substituted at its aryl ring with one to two radicals selected from amino, chloro, bromo, fluoro, hydroxy, methoxy and optionally halo-substituted methyl, or a protected derivative thereof) and $R^4$ is hydrogen, $(C_{1-5})$ alkyl or $(C_{6-10})$aryl$(C_{1-5})$alkyl. More preferred compounds of Formula I are those in which in which $R^2$ is $(C_{1-5})$alkyl (optionally substituted with one or two radicals selected from amino, chloro, bromo, fluoro and hydroxy, or a protected derivative thereof), perfluoro$(C_{1-5})$alkyl, $(C_{5-6})$ cycloalkyl, $(C_{5-6})$cycloalkylmethyl or a group selected from phenyl, naphthyl and benzyl (which group is optionally substituted with one radical selected from amino hydroxy, chloro, bromo or fluoro, or a protected derivative thereof) and $R^4$ is hydrogen or methyl. Particularly preferred compounds of Formula I are those in which $R^2$ is methyl, trifluoromethyl, optionally substituted phenyl, 2-naphthyl or 2-phenylethyl. Most preferred compounds of Formula I in which $R^2$ is phenyl, 2-naphthyl or 2-phenylethyl, particularly phenyl or 2-naphthyl, and $R^4$ is hydrogen.

Generally preferred compounds of Formula II in which $R^9$ is —C(O)OR$^{10}$, —P(O)(OR$^{10}$)$_2$, —S(O)(NR$^{10}$)R$^{10}$, —C(O) NHC(O)R$^{10}$ or —S(O)$_2$NHC(O)R$^{10}$ are those in which each $R^{10}$ is independently $(C_{1-5})$alkyl (optionally substituted with one or two radicals selected from amino, chloro, bromo, fluoro, hydroxy and methoxy or a protected derivative thereof, $(C_{3-7})$cycloalkyl, $(C_{3-7})$cycloalkyl$(C_{1-5})$alkyl, or a group selected from phenyl or phenyl$(C_{1-6})$alkyl (which group is optionally substituted at its phenyl ring with one to two radicals selected from amino, chloro, bromo, fluoro, hydroxy, methoxy and optionally halo-substituted methyl, or a protected derivative thereof). More preferred compounds of Formula II in which $R^9$ is —C(O)OR$^{10}$, —P(O)(OR$^{10}$)$_2$, —S(O)(NR$^{10}$)R$^{10}$, —C(O)NHC(O)R$^{10}$ or —S(O)$_2$NHC(O) R$^{10}$ are those in which in which R$^{10}$ is ethyl, (C$_{5-6}$) cycloalkyl, (C$_{5-6}$)cycloalkylmethyl or a group selected from phenyl and benzyl (which group is optionally substituted at its phenyl ring with one radical selected from amino hydroxy, chloro, bromo or fluoro, or a protected derivative thereof).

Generally preferred compounds of Formula II in which R$^9$ is C(O)R$^{11}$ or —S(O)R$^{11}$ are those in which R$^{11}$ is (C$_{1-5}$) alkyl, (C$_{3-7}$)cycloalkyl, (C$_{3-7}$)cycloalkyl(C$_{1-5}$)alkyl or a group selected from phenyl and phenyl(C$_{1-6}$)alkyl (which group is optionally substituted at its aryl ring with one to two radicals selected from amino, chloro, bromo, fluoro, hydroxy, methyl, trifluoromethyl and methoxy). More preferred compounds of Formula II in which R$^{11}$ is C(O)R$^{11}$ or —S(O)R$^{11}$ are those in which in which R$^{11}$ is ethyl, cyclo (C$_{5-6}$)alkyl, cyclo(C$_{5-6}$)alkylmethyl or a group selected from phenyl and benzyl (which group is optionally substituted at its phenyl ring with one radical selected from amino hydroxy, chloro, bromo or fluoro, or a protected derivative thereof.

Generally preferred compounds of Formula II in which R$^9$ is —C(O)NR$^{12}$R$^{13}$ or —S(O)$_2$NR$^{12}$R$^{13}$ are those in which R$^{12}$ and R$^{13}$ are independently (C$_{1-5}$)alkyl, (C$_{3-7}$)cycloalkyl, (C$_{3-7}$)cycloalkyl (C$_{1-5}$)alkyl or a group selected from phenyl and phenyl(C$_{1-6}$)alkyl (which group is optionally substituted at its phenyl ring with one to two radicals selected from amino, chloro, bromo, fluoro, hydroxy, methoxy and optionally halo-substituted methyl). More preferred compounds of Formula II in which R$^9$ is —C(O)NR$^{12}$R$^{13}$ or —S(O) $_2$NR$^{12}$R$^{13}$ are those in which R$^{12}$ and R$^{13}$ are independently ethyl, (C$_{5-6}$)cycloalkyl, (C$_{5-6}$)cycloalkylmethyl or a group selected from phenyl and benzyl (which group is optionally substituted at its phenyl ring with one radical selected from amino hydroxy, chloro, bromo or fluoro, or a protected derivative thereof).

Preferred compounds of Formula II in which R$^9$ is —C(O)NHR$^{14}$ or —S(O)$_2$NHR$^{14}$ wherein R$^{14}$ is a group selected from Formulae (a) and (b) are those in which each n, A, B, Y, Z, R$^1$ and R$^{10}$ are as defined above with respect to preferred compounds of Formulae I, II and III.

Generally preferred compounds of Formula III are those in which R$^{15}$ is a group selected from 2-furyl, 2-thienyl, 2-pyrrolyl, 2-phospholyl, 2-arsoyl, 3-pyridyl or 3-phosphorinyl (which group is optionally substituted with at least one radical selected from (C$_{1-5}$)alkylcarbamoyl, di(C$_{1-5}$)alkylcarbamoyl, (C$_{1-5}$)alkyloxycarbonyl, (C$_{1-5}$) alkylsulfinamoyl, di(C$_{1-5}$)alkylsulfinamoyl, (C$_{1-5}$) alkylsulfonyl, carboxy, nitro, sulfinamoyl, sulfo, carbamoyl, phosphono, (C$_{1-5}$)alkyloxyphosphinyl, di(C$_{1-5}$) alkyloxyphosphinyl, (C$_{1-5}$)alkanoyl, cyano, (C$_{1-5}$) alkylsulfinyl, sulfamoyl, (C$_{1-5}$)alkylsulfamoyl, di(C$_{1-5}$) alkylsulfamoyl, (C$_{1-5}$)alkyloxysulfonyl, (C$_{1-5}$), phenyl, naphthyl, pyridyl, thienyl, furyl, imidazolyl, indolyl, hydroxy, (C$_{1-5}$)alkyloxy, optionally halo-substituted (C$_{1-5}$) alkyl, benzyl, halo, —$^+$N(R$^{17}$)$_3$, wherein each R$^{17}$ is independently (C$_{1-5}$)alkyl, phenyl or benzyl, or —N(R$^{18}$)$_2$, wherein each R$^{18}$ is independently hydrogen, (C$_{1-5}$)alkyl, phenyl or benzyl). More preferred compounds of Formula III are those in which R$^{1-5}$ is a group selected from 2-furyl, 2-thienyl, 2-pyrrolyl, 2-phosholyl, 2-arsolyl, 3-pyridyl or 3-phosphorinyl (which group is optionally substituted with at least one radical selected from methylcarbamoyl, dimethylcarbamoyl, methyloxycarbonyl, methylsulfinamoyl, dimethylsulfinamoyl, methylsulfonyl, carboxy, nitro, sulfinamoyl, sulfo, carbamoyl, phosphono, methyloxyphosphinyl, dimethyloxyphosphinyl, formyl, cyano, methylsulfinyl, sulfamoyl, methylsulfamoyl, dimethylsulfamoyl, methoxysulfonyl, methylsulfonimidoyl, phenyl, naphthyl, pyridyl, thienyl, furyl, imidazolyl, indolyl, hydroxy, methoxy, methyl, trifluromethyl, benzyl, halo, —$^+$N(R$^{17}$)$_3$, wherein each R$^{17}$ is independently methyl, phenyl or benzyl, or —N(R$^{18}$)$_2$, wherein each R$^{18}$ is independently hydrogen, methyl, phenyl or benzyl). Generally preferred compounds of Formula III in which R$^{16}$ is a group selected from Formulae (a) and (b) are those in which each n, A, B, Y, Z, R$^1$ and R$^{10}$ are as defined above with respect to preferred compounds of Formulae I, II and III.

In general, preferred cysteine protease inhibitors of the invention are those in which the absolute configuration of each chiral center present is the (S)-configuration. However, preferred compounds of Formula I in which n is 0 are those in which the absolute configuration of chiral center to which the R$^7$ substituent is attached is in the (R)-configuration. For example, preferred compounds of Formula I include: N$^2$-(4-morpholinylcarbonyl)-N$^1$-(3-phenyl-1R-phenylsulfonylpropyl)-L-phenylalaninamide (compound 1), N$^2$-(4-morpholinylcarbonyl)-N$^1$-(3-phenyl-1S-phenylsulfonylpropyl)-L-phenyalaninamide (compound 2), N$^2$-(4-morpholinylcarbonyl)-N$^1$-(3-phenyl-1-phenylsulfonylpropyl)-L-phenylalaninamide (compound 3), N$^2$-(4-morpholinylcarbonyl)-N$^1$-(3-phenyl-1-benzylsulfonylpropyl)-L-leucinamide (compound 4), N$^2$-(4-morpholinylcarbonyl)-N$^1$-(3-phenyl-1-trifluoromethylsulfonylpropyl)-L-phenylalaninamide (compound 5), N$^2$-(4-morpholinylcarbonyl)-N$^1$-(3-phenyl-1-benzylsulfonylpropyl)-L-phenylalaninamide (compound 6), N$^2$-(4-morpholinylcarbonyl)-N$^1$-(3-phenyl-1-phenylsulfonylpropyl)-L-leucinamide (compound 7), N$^2$-(4-morpholinylcarbonyl)-N$^1$-(3-phenyl-1-fluoromethylsulfonylpropyl)-L-phenylalaninamide (compound 8), N$^1$-(4-morpholinylcarbonyl)-N$^1$-(3-phenyl-1S-phenylsulfonylmethylpropyl)-L-phenylalaniamide (compound 9); N$^2$-(4-morpholinylcarbonyl)-N$^1$-{3-phenyl-1S-|2-(2-phenylethylsulfonyl)ethyl|propyl}-L-phenylalaninamide (compound 10); N$^2$-(4-morpholinylcarbonyl)-N$^1$-{3-phenyl-1S-|2-(2-naphthylsulfonyl)ethyl|propyl}-β-(2-naphthyl)-L-alaninamide (compound 11); N$^2$-phenylacetyl-N$^1$-|3-phenyl-1S-(2-phenylsulfonylethyl)propyl|-L-phenylalaninamide (compound 12), M-(N-benzyloxycarbonyl-β-alanyl)-N$^1$-|3-phenyl-1S-(2-phenylsulfonylethyl)propyl|-L-phenylalaninamide (compound 13), 3-{2-phenyl-1S-[3-phenyl-1S-(2-phenylsulfonylethyl)propylcarbamoyl] ethylcarbamoyl}propionic acid (compound 14); 3-{2-naphthyl-1S-[3-phenyl-1S-(2-phenylsulfonylethyl) propylcarbamoyl]ethylcarbamoyl}propionic acid (compound 15); N$^1$-(4-morpholinylcarbonyl)-N$^1$-{3-phenyl-1S-[2-(2-naphthylsulfonyl)ethyl|propyl}L-tyrosinamide (compound 16); methyl 3-{2-phenyl-1S-|3-phenyl-1S-(2-phenylsulfonylethyl)propylcarbamoyl] ethylcarbamoyl}propionate (compound 17); N$^2$-(4-morpholinylcarbonyl)-N$^1$-|3-phenyl-1S-(2-phenylsulfonylethyl)propyl|-L-phenylalaninamide (compound 18); N$^2$-(β-alanyl)-N$^1$-|3-phenyl-1S-(2-phenylsulfonylethyl) propyl|-L-phenylalaninamide (compound 19); and 5-phenylsulfonyl-3S-{N-|N-(N-acetyl-L-tyrosyl)-L-valyl|-L-alanylamino}valeric acid (compound 20). Preferred compounds of Formula II include: ethyl 4S-(N-benzylsulfonyl-β-(2-naphthyl)-L-alanylamino)-6-phenylhexanoate (compound 21); ethyl 4S-(N-benzylcarbamoyl-β-(2-naphthyl)-L-alanylamino)-6-phenylhexanoate (compound 22); ethyl 4S-[N-(4-morpholinylcarbonyl)-L-2-(naphthyl-L-alanylamino|-6-phenylhexanoate (compound 23); ethyl 4S-(N-benzylcarbamoyl-L-phenylalanylamino)-6-phenylhexanoate (compound 24); ethyl 4S-[N-(4-morpholinylcarbonyl)-L-phenylalanylamino]-6-phenylhexanoate (compound 25); N²-(4-morpholinylcarbonyl)-N¹-[3-phenyl-1S-(2-phenylcarbamoylethyl)propyl]-L-phenylalaninamide (compound 26); and N²-(4-morpholinylcarbonyl)-N¹-|3-phenyl-1S-(2-benzylcarbamoylethyl)propyl]-L-phenylalaninamide (compound 27). Preferred compounds of Formula III include: N²-(4-morpholinylcarbonyl)-N¹-{3-phenyl-1S-|2-(4-methoxyphenyl)ethyl|propyl}-L-phenylalaninamide (compound 28); and N²-(4-morpholinylcarbonyl)-N¹-{3-phenyl-1S-|2-(4-aminophenyl)ethyl|propyl}-L-phenylalaninamide (compound 29).

As will be appreciated by those in the art, Formula I includes structures represented by preferred Species IV as depicted below.

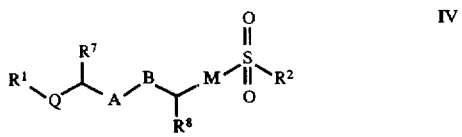

wherein M is zero, one or two carbon atoms, A-B are as defined above, R¹, R², R⁷ and R⁸ are as defined above, and Q is NH or CH₂. Preferred embodiments utilize A-B linkages which contain nitrogen at the B position. In this embodiment, the number of carbon atoms between the carbon to which the R⁸ group is attached and the sulfur atom of the sulfone group determines whether the compound is an α-aminosulfone, β-aminosulfone, or a γ-aminosulfone. As is discussed below in the Examples, compounds may be named as aminosulfones using the names of the amino acids or using the chemical names.

Thus, for example, Species V is an α-aminosulfone:

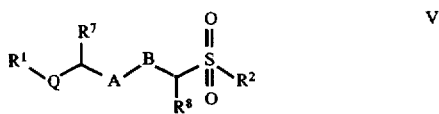

Species VI is a β-aminosulfone:

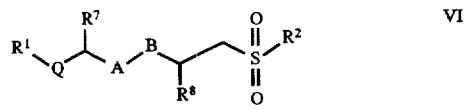

Species VII is a γ-aminosulfone:

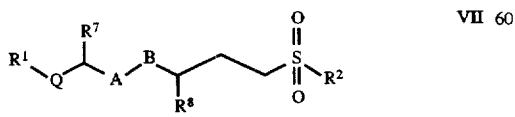

Formula II includes structures of Species VIII, referred to as γ-amino groups, particularly when R⁹ is an electron withdrawing group:

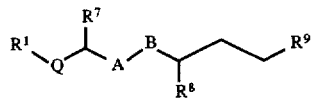

In a preferred embodiment, the dissociation constant for inhibition of a protease with an inhibitor of the invention, generally referred to by those in the art as $K_i$, is at most 100 μM. By the term "binding constant" or "dissociation constant" or grammatical equivalents herein is meant the equilibrium dissociation constant for the reversible association of inhibitor with enzyme. The dissociation constants are defined and determined as below.

The determination of dissociation constants is known in the art. For example, for reversible inhibition reactions such as those of the present invention, the reaction scheme is as follows:

Equation 3

The enzyme and the inhibitor combine to give an enzyme-inhibitor complex, E.I. This step is assumed to be rapid and reversible, with no chemical changes taking place; the enzyme and the inhibitor are held together by non-covalent forces. In this reaction, $k_1$ is the second order rate constant for the formation of the E.I reversible complex. $k_2$ is the first order rate constant for the disassociation of the reversible E.I complex. In this reaction, $K_i = k_2/k_1$.

The measurement of the equilibrium constant K, proceeds according to techniques well known in the art, as described in the examples. For example, assays generally use synthetic chromogenic or fluorogenic substrates.

The respective $K_i$ values may be estimated using the Dixon plot as described by Irwin Segel in Enzyme Kinetics: Behavior and analysis of rapid equilibrium and steady-state enzyme systems, 1975, Wiley-Interscience Publication, John Wiley & Sons, New York, or for competitive binding inhibitors from the following calculation:

$$1 - (v_i/v_o) = [I]/([I] + K_i(1 + ([S]/K_M)))$$  Equation 4 wherein $v_o$ is the rate of substrate hydrolysis in the absence of inhibitor, and $v_i$ is the rate in the presence of competitive inhibitor.

It is to be understood that dissociation constants are a particularly useful way of quantifying the efficiency of an enzyme with a particular substrate or inhibitor, and are frequently used in the art as such. If an inhibitor exhibits a very low $K_i$, it is an efficient inhibitor. Accordingly, the cysteine protease inhibitors of the present invention have dissociation constants, $K_i$, of at most about 100 μM. Preferred embodiments have inhibitors that exhibit dissociation constants of at most about 10 μM, with the most preferred embodiments having dissociation constants of at most about 1 μM.

CHEMISTRY

The synthesis of the inhibitors of the invention proceeds as follows. Compounds of Formula I in which X represents a bond can be prepared by the process depicted in Scheme 1 of FIG. 1.

Treatment of tert-butylcarbamate or benzyl carbamate with an appropriate aldehyde, such as isobutyraldehyde or hydrocinnamaldehyde, along with the sodium salt of a suitable sulfinic acid, such as benzenesulfinic acid (Aldrich Chemical Co.), in the presence of aqueous formic acid affords the corresponding N-protected aminomethyl sulfone. Benzyloxycarbonyl protected aminomethyl sulfones are deprotected with hydrogen bromide in acetic acid. Coupling with a suitable N-protected amino acid or peptide or a peptidomimetic derivative thereof affords a compound of Formula I in which X represents a bond. Alternatively, an appropriate N-terminal protected amino acid or peptide of peptidomimetic derivative thereof, such as N-(4-morpholinylcarbonyl)phenylalaninamide, is reacted with an appropriate aldehyde along with the sodium salt of a suitable sulfinic acid, in the presence of aqueous formic acid to afford a compound of Formula I in which X represents a bond.

Compounds of Formula 1 in which X represents a methylene bond can be prepared by the processes depicted in Schemes 2 and 3, FIGS. 2 and 3, respectively.

Treatment of a suitable N-protected amino acid or peptidomimetic derivative thereof with sodium borohydride affords the corresponding β-aminoethanol. Treatment of the alcohol with methanesulfonyl chloride in the presence of triethylamine affords the corresponding mesylate. Nucleophilic displacement with the anion of a thiol, such as thiophenol, according to the method of Spaltenstein, A., Carpion, P., Miyake, F., and Hopkings, P. B., J. Org. Chem (1987) 52, 3759, affords the corresponding β-aminosulfide. The sulfide is oxidized by means of 4-chloroperbenzoic acid to give the corresponding N-protected β-aminoethyl sulfone. In a special instance, the mesylate is treated with thiolate ion such as that derived from 2-(trimethylsilyl)ethanethiol, the synthesis of which is described by Anderson, M. B., Ranasinghe, M. B., Palmer, J. T., Fuchs, P. L., J. Org. Chem. (1988) 53, 3125, to give the corresponding β-aminoethyl 2-trimethylsilylethyl sulfide. The 2-trimethylsilylethyl sulfide is reduced to the corresponding β-aminoethyl 2-trimethylsilylethyl sulfone, which is then subjected to fluoride-mediated cleavage, extruding trimethylsilyl fluoride and ethene as gaseous by-products, and an intermediate sulfinate, which sulfinate is alkylated in situ with an appropriate halogen-containing species such as bromochloromethane to give the corresponding N-protected β-aminoethyl halomethyl sulfone. The N-protected β-aminoethyl sulfones are deprotected and then coupled with a suitable N-protected amino acid or peptide or a peptidomimetic derivative thereof to afford a compound of Formula I in which X is methylene.

Compounds of Formula II and Formula I in which X represents ethylene can be prepared by the processes depicted in Equations 5, 6 and 7.

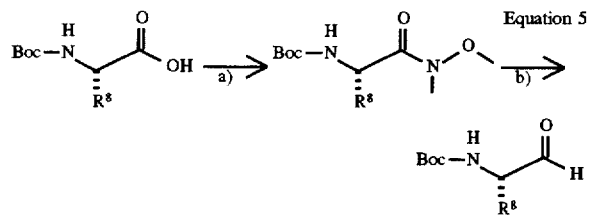

wherein a) is a) Cl—H₂N+(Me)OMe, dicyclohexylcarbodiimide, triethylamine; and b) lithium aluminum hydride.

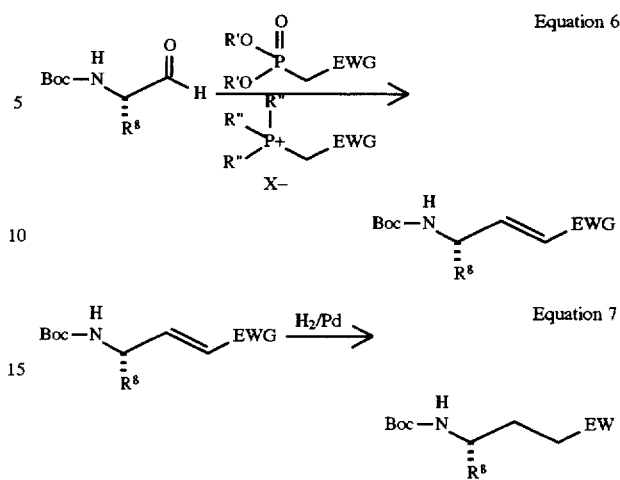

An appropriate N-tert-butoxycarbonyl amino acid or peptidomimetic derivative thereof is converted to the corresponding aminomethyl aldehyde (e.g., see method of Fehrentz, J-A. and Castro, B. (Synthesis, (1983), 676; Equation 5). The aldehyde is converted to the corresponding vinylogous compound via aWittig reaction or a Wadsworth-Emmons-Horner modification of the Wittig reaction (e.g., see Wadsworth et al., J. Amer. Chem. Soc. 83: 1733 (1991); Equation 6). The vinylogous compound is reduced by catalytic hydrogenation (e.g., see Equation 7) and then deprotection and coupling with a suitable N-protected amino acid or peptide or a peptidomimetic derivative thereof gives the corresponding compound of Formula I or II. Alternatively, the vinylogous compound is deprotected and coupled with the N-protected amino acid or peptide or a peptidomimetic derivative thereof to give the corresponding vinyloguous condensation product, which is then reduced to give the corresponding compound of Formula I or II.

Compounds of Formula II can be prepared by the processes depicted in Scheme 4, FIG. 4.

Preferably, the conversion of N-tert-butoxycarbonyl amino acid or peptidomimetic derivative thereof to the corresponding aminomethyl aldehyde is carried out with N,O-dimethylhydroxylamine hydrochloride in the presence of triethylamine and dicyclohexylcarbodiimide in dicloromethane. Alternatively, the conversion is carried out by treating the amino acid or peptidomimetic derivative with triethylamine and the coupling agent benzotriazol-1-yloxytris(dimethylamino)phosphonium hexafluorophosphate (BOP) and then reducing with lithium aluminum hydride to give the corresponding aldehyde (e.g., see methos of Fehrentz, J-A. and Castro, B.; Synthesis, (1983), 676–678). The conversion of the aldehyde to the corresponding vinylogous ester can be carried out with the sodium anion of triethyl phosphonoacetate. Deprotection of the vinylogous ester can be carried out with hydrogen chloride in dioxane. The hydrogenation is typically carried out in the presence of palladium.

Compounds of Formula I in which X is ethylene are conveniently prepared by the process depicted in Scheme 5, FIG. 5.

Treatment of a suitable N-tert-butoxycarbonyl-α-aminoaldehyde, prepared as described in Equation 5, with the sodium anion of an appropriate sulfonylmethanephosphonate (SMP) (e.g. diethyl phenylsulfonylmethanephosphonate, diethyl 2-naphthylsulfonylmethane-phosphonate, diethyl methylsulfonylmethanephosphonate, etc.) gives the corresponding vinylogous sulfone. The sulfone is deprotected with anhydrous p-toulenesulfonic acid in ether and then coupled with N-protected amino acid or peptide or a peptidomimetic derivative thereof to give the corresponding vinyloguous condensation product, which is then reduced to give the corresponding compound of Formula I. Suitable arylsulfonylmethanephsophonates can be prepared by treating arylthiols with paraformaldehyde in the presence of hydrogen chloride and reacting with triethyl phosphite to give the corresponding diethyl phsophonomethyl aryl sulfide and then oxidizing the sulfide. Alternatively, suitable sulfides can be obtained commercially (e.g., diethylphosphonomethyl methyl sufide obtained from Aldrich Chemical Co., diethylphosphonomethyl phenyl sulfide, etc.) and oxidized to their corresponding sulfones.

Compounds of Formula II in which $R^9$ is —COOH can be prepared by the process depicted in Scheme 6, FIG. 6.

Generally, saponification of a compound of Formula II in which $R^9$ is —COOR$^{10}$ results in the cooresponding carboxylate, which upon treatment with acid gives the corresponding carboxylic acid.

Compounds of Formula II in which $R^9$ is —P(O)(R$^{10}$)$_2$ can be prepared as depicted in Scheme 7 (FIG. 7) by proceeding as in Scheme 6, but substituting for the SMP the sodium anion of an appropriate methylenediphosphonate (e.g., tetraethyl methylenediphosphonate, etc.).

Compounds of Formula II in which $R^9$ is —C(O)NHR$^{14}$ can be prepared as depicted in Scheme 8 (FIG. 8) by proceeding as in Scheme 6, but substituting for the SMP an appropriate diethyl amidomethylenephsophonate (e.g., diethyl benzylamidomethylenephosphonate, etc.).

Suitable amidomethylenephsophonates can be prepared by reacting the saponification product of triethyl phosphonoacetate with an appropriate amine. Altenatively, compounds of Formula II in which $R^9$ is —C(O)NHR$^{14}$ can be prepared by reacting a compound of Formula I in which $R^9$ is —COOH with an appropriate amine. For example, the reaction can be carried out in the presence of dicyclohexylcarbodiimide in dichloromethane or by any other peptide coupling reaction sequences known to those of skill in the art.

In general, compounds of Formula II can be prepared by the process depicted in Scheme 9 (FIG. 9) and substituting the starting materials represented by Structures I-VII.

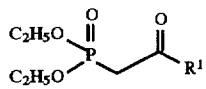

Structure I

Synthesis of ketones is performed by means of the Wadsworth-Emmons reaction between Boc-α-amino aldehydes and the appropriate phosphonate, followed by catalytic reduction with hydrogen in the presence of palladium. Generally, the aldehyde portion is synthesized as outlined above. The phosphonate, if not commercially available, is synthesized by treatment of the enolate anion of methyl or substituted methyl ketones, such as acetone or acetophenone, with diethyl chlorophosphonate. The enolate anion is generated, for example, by treatment of a tetrahydrofuran solution of diisopropylamine with butyllithium, followed by addition of the ketone to the lithium diisopropylamide (LDA) solution (H. O. House, Modern Synthetic Reactions, 2nd Ed. (W. Benjamin, Inc., Menlo Park, Calif., Chapter 9). Following formation of the enolate, diethyl chlorophosphonate is added. The Wadsworth-Emmons reagent forms as a consequence of coupling of the enolate with diethyl chlorophosphate.

For the synthesis of cysteine protease inhibitors with nitriles as the EWG, structure II is used:

Structure II

Synthesis of nitriles is performed by means of the Wadsworth-Emmons reaction between Boc-α-amino aldehydes and the appropriate phosphonate, followed by hydrogenation in the presence of a suitable catalyst. Generally, the aldehyde portion is synthesized as outlined above. The phosphonate is commercially available.

For the synthesis of cysteine protease inhibitors with sulfoxides as the EWG, structure III is used:

Structure III

Synthesis of sulfoxides is performed by means of the Wadsworth-Emmons reaction between Boc-α-amino aldehydes and the appropriate phosphonate, followed by hydrogenation in the presence of a suitable catalyst. Generally, the aldehyde portion is synthesized as outlined above. The phosphonate is synthesized by treatment of the anion of methyl sulfoxides with diethyl chlorophosphate. The anion is generated by addition of BuLi to diisopropylamine, followed by addition of the methyl sulfoxide.

For the synthesis of cysteine protease inhibitors with sulfonamides as the EWG, structure IV is used:

Structure IV

Synthesis of sulfonamides is performed by means of the Wadsworth-Emmons reaction between Boc-α-amino aldehydes and the appropriate phosphonate, followed by hydrogenation in the presence of a suitable catalyst. Generally, the aldehyde portion is synthesized as outlined above. The phosphonate is synthesized, for instances, by a method such as the following: a) diethylphosphoryl methanesulfonates, as prepared by the method of Carretero and Ghosez (Tetrahedron Left., 28:1104–1108(1987)), are converted to sulfonyl chlorides by treatment with phosphorus pentachloride (M. Quaedvlieg, in "Methoden der Organische Chemic (Houben-Weyl)", ed. E. Muller, Thieme Verlag, Stuttgart, 4th Ed., 1955, Vol. IX, Chapter 14); or b) treatment of the sulfonyl chloride with an amine, such as ammonia, a primary amine (including an amino acid derivative), or a secondary amine, that results in the formation of the sulfonamide (Quaedvlieg, supra, Chapter 19). The sulfonamidephosphonate is then reacted with Boc-α-aminoaldehydes to form the target compounds as per the Wadsworth-Emmons reaction.

For the synthesis of cysteine protease inhibitors with sulfinamides as the EWG, structure V is used:

Structure V

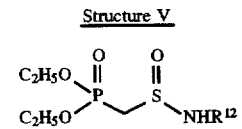

Synthesis of sulfinamides is performed by means of the Wadsworth-Emmons reaction between Boc-α-amino aldehydes and the appropriate phosphonate, followed by hydrogenation in the presence of a suitable catalyst. Generally, the aldehyde portion is synthesized as outlined above. The phosphonate may be synthesized using one of the following methods. Treatment of methyl dialkyl phosphonates such as the commercially available methyl diethyl phosphonate (Aldrich), with thionyl chloride in the presence of aluminum chloride gives the dialkylphosphoryl methanesulfinyl chloride (Vennstra et al., Synthesis (1975) 519. See also Anderson, "Comprehensive Organic Chemistry (Pergamon Press)", Vol. 3, Chapter 11.18, (1979). Alternatively, treatment of the dialkyl phosphoryl sulfinyl chloride with amines (Stirling, Internat. J. Sulfur Chem. (B) 6:277 (1971)), yields the dialkyl phosphoryl sulfinamide.

For the synthesis of cysteine protease inhibitors with sulfoximines as the EWG, structure VI is used:

Structure VI

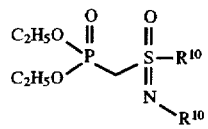

Synthesis of sulfoximines is performed by means of the Wadsworth-Emmons reaction between Boc-α-amino aldehydes and the appropriate phosphonate, followed by hydrogenation in the presence of a suitable catalyst. Generally, the aldehyde portion is synthesized as outlined above. The phosphonate may be synthesized in several ways. For example, N-alkyl or N-aryl phenyl methyl sulfoximines are made by the methods described by Johnson, in "Comprehensive Organic Chemistry " (Pergamon Press), supra, Chapter 11.11. Alternatively, the lithium anion of compounds such as N-alkyl phenyl methyl sulfoximine is prepared by the treatment of the neutral compound with buthyl lithium in THF (Cram et al., J. Amer. Chem. Soc. 92:7369 (1970)). Reaction of this lithium anion with dialkyl chlorophosphates such as the commercially available diethyl chlorophosphate (Aldrich) results in the Wadsworth-Emmons reagent necessary for synthesis of the sulfoximine compounds.

For the synthesis of cysteine protease inhibitors with sulfonates as the EWG, structure VII is used:

Structure VII

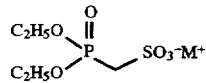

Synthesis of sulfonates is performed by means of the Wadsworth-Emmons reaction between Boc-α-amino aldehydes and the appropriate phosphonate, for instance diethylphosphoryl methanesulfonate, followed by hydrogenation in the presence of a suitable catalyst, such as Raney nickel. The phosphonate may be synthesized as follows. The anion of methyl dialkyl phosphonates such as the commercially available methyl diethyl phosphonate (Aldrich) is generated by treatment of said phosphonate with a strong base such as LDA. The resulting anion is sulfonated with sulfur trioxide/trimethylamine complex (Carreto et al., Tetrahedron Lett., 28:1104–1108 (1987)) to form diethylphosphoryl methanesulfonate, which is capable of reacting in the Wadsworth-Emmons procedure with aldehydes to form α,β-unsaturated sulfonates.

Compounds of Formula II can be prepared by the process depicted in Scheme 10 (FIG. 10).

The chloride compounds containing $R_8$ and $R_9$ groups are generally made using commercially available reagents and products using techniques well known in the art. The reaction generally produces a mixture of cis and trans configurations, favoring the trans isomer. Upon reduction to the cysteine protease inhibitors of this embodiment, the cis-trans isomerism disappears by definition as a single compound is formed.

In one embodiment, the cysteine protease inhibitors of the invention are further purified if necessary after synthesis, for example to remove unreacted materials. For example, the cysteine protease inhibitors of the present invention may be crystallized, or passed through silica chromatography columns using solvent mixtures to elute the pure inhibitors.

In summary, the processes for preparing compounds of the invention are as follows:

(A) for the preparation of Formula IV:

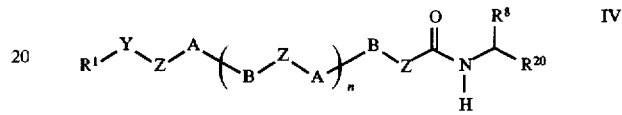

in which n is 0 to 12; $R^{20}$ is cyano, $-S(O)_2R^2$, $-CH_2S(O)_2R^2$, $-CH_2CH(R^4)S(O)OR^{10}$, $-(CH_2)_2P(O)(OR^{10})_2$, $-(CH_2)_2S(O)(NR^{10})R^{11}$, $-CH_2)_2C(O)R^{11}$, $-(CH_2)_2C(O)NR^{12}R^{13}$, $-(CH_2)_2S(O)_2NR^{12}R^{13}$, $-(CH_2)_2C(O)NHR^{14}$, $-(CH_2)_2S(O)_2NHR^{14}$ or $-CH_2CHR^{15}R^{16}$ and each A, B, X, Y, Z, $R^1$, $R^8$, $R^1$, $R^8$, $R^2$, $R^{10}$, $R^{11}$, $R^{12}$, $R^{13}$, $R^{14}$, $R^{15}$ and $R^{16}$ are as defined in the Summary of the Invention with respect to compounds of Formulae I, II and III, and the pharmaceutically acceptable salts, individual isomers and mixtures of isomers thereof, reacting an amine of Formula V:

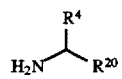

with a compound of the Formula VI:

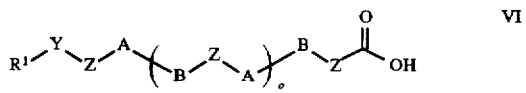

in which each n, A, B, X, Y, Z, $R^1$, $R^8$ and $R^{20}$ are as defined above;

(B) for the preparation of a compound of Formula IV in which $R^{20}$ is $-S(O)_2R^2$, and the pharmaceutically acceptable salts, individual isomers and mixtures of isomers thereof.

reacting a compound of Formula VII;

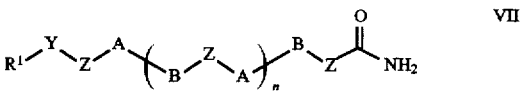

with an aldehyde of the formula $R^8CHO$ and a sodium sulfinate of the formula $R^2S(O)ONa$, in which each n, A, B, X, Y, Z, $R^1$ and $R^8$ are as defined above;

(C) for the preparation of a compound of Formula IV in which $R^{20}$ is $-S(O)_2R^2$, and the pharmaceutically acceptable salts, individual isomers and mixtures of isomers thereof, (1) reacting a compound of the formula $NH_2P$, wherein P is a protective group, with an aldehyde of the formula $R^8CHO$ and a sodium sulfinate of the formula $R^2S(O)ONa$ and then deprotecting to give a compound of Formula VIII:

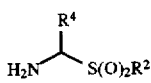

in which each $R^2$ and $R^8$ are as defined in the Summary of the Invention with respect to Formula I; and (2) reacting the compound of Formula VIII with a compound of Formula VI in which each n, A, B, X, Y, Z and $R^1$ are as defined above;

(D) for the preparation of a compound of Formula IV in which $R^{20}$ is —$CH_2S(O)_2R^2$ and the pharmaceutically acceptable salts, individual isomers and mixtures of isomers thereof, (1) reacting a compound of Formula IX:

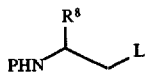

with a thiolate anion of the formula $R^2S^-$, in which L is a leaving group $R^2$ and $R^8$ are as defined above, to give a compound of Formula X:

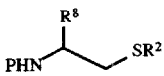

(2) oxidizing the compound of Formula X to give a compound of Formula XI:

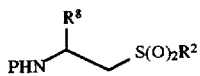

and (3) reacting the compound of Formula XI with a compound of Formula VI in which each n, A, B, X, Y, Z and $R^1$ are as defined above;

(E) for the preparation of a compound of Formula IV in which $R^{20}$ is cyano, —$(CH_2)_2S(O)_2R^2$, —$(CH_2)_2C(O)OR^{10}$, —$(CH_2)_2P(O)(OR^{10})_2$, —$(CH_2)_2S(O)(NR^{10})R^{10}$, —$(CH_2)_2C(O)R^{11}$, —$(CH_2)_2S(O)R^{11}$, —$(CH_2)_2C(O)NR^{12}R^{13}$, —$(CH_2)_2S(O)_2NR^{12}R^{13}$, —$(CH_2)_2C(O)NHR^{14}$, and the pharmaceutically acceptable salts, individual isomers and mixtures of isomers thereof, (1) reacting an aldehyde of Formula XII:

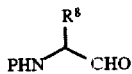

with a compound selected from Formulae XII and XIV:

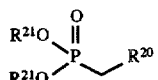  XIII

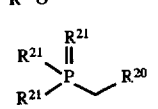  XIV in which each $R^8$ and $R^{20}$ are as defined above, and then deprotecting to give a compound of Formula XV:

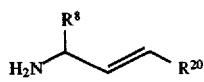  XV (2) reacting the compound of Formula XV with a compound of Formula VI in which each n, A, B, X, Y, Z and $R^1$ are as defined above, and (3) reducing;

(F) for the preparation of a compound of Formula IV in which $R^{20}$ is —$CH_2CHR^{15}R^{16}$ and the pharmaceutically acceptable salts, individual isomers and mixtures of isomers thereof, (1) reacting an aldehyde of Formula XII with compound of Formula XVI:

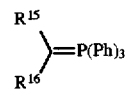  XVI in which each $R^8$, $R^{15}$ and $R^{16}$ are as defined above, and then deprotecting to give a compound of Formula XVII:

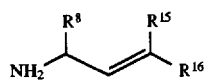  XVII (2) reacting the compound of Formula XVII with a compound of Formula VI in which each n, A, B, X, Y, Z and $R^1$ are as defined above, and (3) reducing;

(G) optionally further converting a non-salt form of a compound of Formula IV into a pharmaceutically acceptable salt;

(H) optionally further converting a salt form of a compund of Formula IV into non-salt form; and (H) optionally further separating a compound of Formula IV into individual stereoisomers.

In one embodiment, the cysteine protease inhibitors of the present invention are labelled. By a "labelled cysteine protease inhibitor" herein is meant a cysteine protease inhibitor that has at least one element, isotope or chemical compound attached to enable the detection of the cysteine protease inhibitor or the cysteine protease inhibitor bound to a cysteine protease. In general, labels fall into three classes: a) isotopic labels, which may be radioactive or heavy isotopes; b) immune labels, which may be antibodies or antigens; and c) colored or fluorescent dyes. The labels may be incorporated into the cysteine protease inhibitor at any position. For example, a label may be attached as the "$R^1$" group in Formula 1, or a radioisotope incorporated into any position. Examples of useful labels include $^{14}C$, $^3H$, biotin, and fluorescent labels as are well known in the art.

PHARMACOLOGY AND UTILITY

Once produced, the cysteine protease inhibitors of the present invention may be easily screened for their inhibitory effect. The inhibitor is first tested against the cysteine protease for which the targeting group of the inhibitor was chosen, as outlined above. Alternatively, many cysteine proteases and their corresponding chromogenic substrates are commercially available. Thus, a variety of cysteine proteases are routinely assayed with synthetic chromogenic substrates in the presence and absence of the cysteine protease inhibitor, to confirm the inhibitory action of the compound, using techniques well known in the art. The effective inhibitors are then subjected to kinetic analysis to calculate the $K_i$ values, and the dissociation constants determined.

If a compound inhibits at least one cysteine protease, it is a cysteine protease inhibitor for the purposes of the invention. Preferred embodiments have inhibitors that exhibit the correct kinetic parameters against at least the targeted cysteine protease.

In some cases, the cysteine protease is not commercially available in a purified form. The cysteine protease inhibitors of the present invention may also be assayed for efficacy using biological assays. For example, the inhibitors may be added to cells or tissues that contain cysteine proteases, and the biological effects measured.

In one embodiment, the cysteine protease inhibitors of the present invention are synthesized or modified such that the in vivo and in vitro proteolytic degradation of the inhibitors is reduced or prevented. Generally, this is done through the incorporation of synthetic amino acids, derivatives, or substituents into the cysteine protease inhibitor. Preferably, only one non-naturally occurring amino acid or amino acid side chain is incorporated into the cysteine protease inhibitor, such that the targeting of the inhibitor to the enzyme is not significantly affected. However, some embodiments that use longer cysteine protease inhibitors containing a number of targeting residues may tolerate more than one synthetic derivative. In addition, non-naturally occurring amino acid substituents may be designed to mimic the binding of the naturally occurring side chain to the enzyme, such that more than one synthetic substituent is tolerated. Alternatively, peptide isosteres are used to reduce or prevent inhibitor degradation.

In this embodiment, the resistance of the modified cysteine protease inhibitors may be tested against a variety of known commercially available proteases in vitro to determine their proteolytic stability. Promising candidates may then be routinely screened in animal models, for example using labelled inhibitors, to determine the in vivo stability and efficacy.

Specific cysteine proteases that may be inhibited by the inhibitors of the present invention are those of the family of cysteine proteases that bear a thiol group at the active site. These proteases are found in bacteria, viruses, eukaryotic microorganisms, plants, and animals. Cysteine proteases may be generally classified as belonging to one of four or more distinct superfamilies. Examples of cysteine proteases that may be inhibited by the novel cysteine protease inhibitors of the present invention include, but are not limited to, the plant cysteine proteases such as papain, ficin, aleurain, oryzain and actinidain; mammalian cysteine proteases such as cathepsins B, H, J, L, N, S, T, O, and C, (cathepsin C is also known as dipeptidyl peptidase 1), interleukin converting enzyme (ICE), calcium-activated neutral proteases, calpain I and II; bleomycin hydrolase, viral cysteine proteases such as picornian 2A and 3C, aphthovirus endopeptidase, cardiovirus endopeptidase, comovirus endopeptidase, potyvirus endopeptidases I and II, adenovirus endopeptidase, the two endopeptidases from chestnut blight virus, togavirus cysteine endopeptidase, as well as cysteine proteases of the polio and rhinoviruses; and cysteine proteases known to be essential for parasite lifecycles, such as the proteases from species of Plasmodia, Entamoeba, Onchocera, Trypansoma, Leishmania, Haemonchus, Dictyostelium, Therileria, and Schistosoma, such as those associated with malaria (*P. falciparium*), trypanosomes (*T. cruzi*, the enzyme is also known as cruzain or cruzipain), murine *P. vinckei*, and the *C. elegans* cysteine protease. For an extensive listing of cysteine proteases that may be inhibited by the cysteine protease inhibitors of the present invention, see Rawlings et al., Biochem. J. 290:205–218 (1993), hereby expressly incorporated by reference.

Accordingly, inhibitors of cysteine proteases are useful in a wide variety of applications. For example, the inhibitors of the present invention are used to quantify the amount of cysteine protease present in a sample, and thus are used in assays and diagnostic kits for the quantification of cysteine proteases in blood, lymph, saliva, or other tissue samples, in addition to bacterial, fungal, plant, yeast, viral or mammalian cell cultures. Thus in a preferred embodiment, the sample is assayed using a standard protease substrate. A known concentration of cysteine protease inhibitor is added, and allowed to bind to a particular cysteine protease present. The protease assay is then rerun, and the loss of activity is correlated to cysteine protease activity using techniques well known to those skilled in the art.

The cysteine protease inhibitors are also useful to remove or inhibit contaminating cysteine proteases in a sample. For example, the cysteine protease inhibitors of the present invention are added to samples where proteolytic degradation by contaminating cysteine proteases is undesirable.

Alternatively, the cysteine protease inhibitors of the present invention may be bound to a chromatographic support, using techniques well known in the art, to form an affinity chromatography column. A sample containing an undesirable cysteine protease is run through the column to remove the protease.

In a preferred embodiment, the cysteine protease inhibitors are useful for inhibiting cysteine proteases implicated in a number of diseases. In particular, cathepsins B, L, and S, cruzain, calpains I and II, and interleukin 1β converting enzyme are inhibited. These enzymes are examples of lysosomal cysteine proteases implicated in a wide spectrum of diseases characterized by tissue degradation. Such diseases include, but are not limited to, arthritis, muscular dystrophy, inflammation, tumor invasion, glomerulonephritis, parasite-borne infections, Alzheimer's disease, periodontal disease, and cancer metastasis. For example, mammalian lysosomal thiol proteases play an important role in intracellular degradation of proteins and in the processing of some peptide hormones. Enzymes similar to cathepsins B and L are released from tumors and may be involved in tumor metastasis. Cathepsin L is present in diseased human synovial fluid and transformed tissues. Similarly, the release of cathepsin B and other lysosomal proteases from polymorphonuclear granulocytes and macrophages is observed in trauma and inflammation.

The cysteine protease inhibitors also find application in a multitude of other diseases, including, but not limited to, gingivitis, malaria, leishmaniasis, filariasis, and other bacterial and parasite-borne infections. The compounds also offer application in viral diseases, based on the approach of inhibiting proteases necessary for viral replication. For example, many picornoviruses including poliovirus, foot and mouth disease virus, and rhinovirus encode for cysteine proteases that are essential for cleavage of viral polyproteins.

Additionally, these compounds offer application in disorders involving interleukin-1β converting enzyme (ICE), a cysteine protease responsible for processing interleukin 1β; for example, in the treatment of inflammation and immune based disorders of the lung, airways, central nervous system and surrounding membranes, eyes, ears, joints, bones, connective tissues, cardiovascular system including the pericardium, gastrointestinal and urogenital systems, the skin and the mucosal membranes. These conditions include infectious diseases where active infection exists at any body site, such as meningitis and salpingitis; complications of infections including septic shock, disseminated intravascular coagulation, and/or adult respiratory distress syndrome; acute or chronic inflammation due to antigen, antibody and/or complement deposition; inflammatory conditions including arthritis, chalangitis, colitis, encephalitis, endocarditis, glomerulonephritis, hepaitis, myocarditis, pancreatitis, pericarditis, reperfusion injury and vasculitis. Immune-based diseases include but are not limited to conditions involving T-cells and/or macrophages such as acute and delayed hypersensitivity, graft rejection, and graft-versus-host disease; auto-immune diseases including Type I diabetes mellitus and multiple sclerosis. Bone and cartilage reabsorption as well as diseases resulting in excessive deposition of extracellular matrix such as interstitial pulmonary fibrosis, cirrhosis, systemic sclerosis, and keloid formation may also be treated with the inhibitors of the present invention. The inhibitors may also be useful in the treatment of certain tumors that produce IL 1 as an autocrine growth factor and in preventing the cachexia associated with certain tumors. Apoptosis and cell death are also associated with ICE and ICE-like activities and may be treated with the inhibitors of the present invention.

Furthermore, the cysteine protease inhibitors of the present invention find use in drug potentiation applications. For example, therapeutic agents such as antibiotics or anti-tumor drugs can be inactivated through proteolysis by endogeneous cysteine proteases, thus rendering the administered drug less effective or inactive. For example, it has been shown that bleomycin, an antitumor drug, can be hydrolyzed by bleomycin hydrolase, a cysteine protease (see Sebti et al., Cancer Res. January 1991, pages 227–232). Accordingly, the cysteine protease inhibitors of the invention may be administered to a patient in conjunction with a therapeutic agent in order to potentiate or increase the activity of the drug. This co-administration may be by simultaneous administration, such as a mixture of the cysteine protease inhibitor and the drug, or by separate simultaneous or sequential administration.

In addition, cysteine protease inhibitors have been shown to inhibit the growth of bacteria, particularly human pathogenic bacteria (see Bjorck et al., Nature 337:385 (1989)). Accordingly, the cysteine protease inhibitors of the present invention may be used as antibacterial agents to retard or inhibit the growth of certain bacteria.

The cysteine protease inhibitors of the invention also find use as agents to reduce the damage of bacterial cysteine proteases to host organisms. For example, staphylococcus produces a very active extracellular cysteine protease which degrades insoluble elastin, possibly contributing to the connective tissue destruction seen in bacterial infections such as septicemia, septic arthritis and otitis. See Potempa et al., J. Biol. Chem. 263(6):2664–2667 (1988). Accordingly, the cysteine protease inhibitors of the invention may be used to treat bacterial infections to prevent tissue damage.

ADMINISTRATION AND PHARMACEUTICAL COMPOSITION

In general, cysteine protease inhibitors of this invention will be administered in therapeutically effective amounts via any of the usual and acceptable modes known in the art, either singly or in combination with another cysteine protease inhibitor of the invention or with another therapeutic agent. A therapeutically effective amount may vary widely depending on the severity of the disease, the age and relative health of the subject, the potency of the compound used and other factors. Therapeutically effective amounts of the cysteine protease inhibitors of this invention may range from 10 micrograms per kilogram body weight (µg/kg) per day to 10 milligram per kilogram body weight (mg/kg), typically 100 µg/kg/day to 1 mg/kg/day. Thus, a therapeutically effective amount for a 80 kg human may range from 1 mg/day to 1000 mg/day, typically 10 mg/day to 100 mg/day.

One of ordinary skill in the art of treating such diseases will be able, without undue experimentation and in reliance upon personal knowledge and the disclosure of this application, to ascertain a therapeutically effective amount of a cysteine protease inhibitor of this invention for a given disease.

In general, the cysteine protease inhibitors of this invention will be administered as pharmaceutical compositions by one of the following routes: oral, systemic (e.g., transdermal, intranasal, intrapulmonary, or by suppositiory) or parenteral (e.g., intramuscular, intravenous, intrapulmonary or subcutaneous). Compositions can take the form of tablets, pills, capsules, semisolids, powders, sustained release formulations, solutions, suspensions, elixiers, aerosols or any other appropriate composiiton and are comprised of, in general, a cysteine protease inhibitor of the invention in combination with at least one pharmaceutically acceptable excipient. Acceptable excipients are non-toxic, aid administration, and don not adversely affect the therapeutic benefit of the cysteine protease inhibitor of this invention. Such excipient may be any solid, liquid, semisolid or, in the case of an aerosol composition, gaseous excipient that is generally available to one of skill in the art.

Solid pharmaceutical excipients include starch, cellulose, talc, glucolse, lactose, sucrose, gelatin, malt, rice, flour, chalk, silica gel, magnesium stearate, sodium sterate, glycerol monostearate, sodium chloride, dried skim milk and the like. Liguid and semisolid excipients may be selected from water, ethanol, glycerol, propylene glycol and various oils, includingthose of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the cysteine protease inhibitor of this invention in aerosol form. Inert gases suitable for this purpose are nitrogen, carbon dioxide, nitrous oxide, etc. Other suitable pharmaceutical carriers and their formulations are described in A. R. Alfonso *Reminton's Pharmaceutical Sciences* 1985, 17th ed. Easton, Pa.: Mack Publishing Company, hereby expressly incorporated by reference.

The amount of a cysteine protease inhibitor of this invention in the composition may vary widely depending upon the type of formulation, size of a unit dosage, kind of excipients and other factors known to those of skill In the art of pharmaceutical sciences. In general, the final composition will comprise from 0.1% w to 1% w of the cysteine protease inhibitor, preferably 1% w to 10% w, with the remainder being the excipient or excipients.

Preferably the pharmaceutical composition is administered in a single unit dosage form for continuous teatment or in a single unit dosage form ad libitum when relief of symptoms is specifically required. Representative pharmaceutical formulations containing a cysteine protease inhibitor of the invention are described in Example 20, infra.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference.

EXAMPLES

The following abbreviation conventions have been used to simplify the examples.

Mu=morpholine urea
$Xaa_1$=amino acid at P1 position relative to active site of the enzyme
$Xaa_2$=amino acid at P2 position relative to active site of the enzyme
γ-$CO_2$Et=γ-amino ethyl ester
γ-$SO_2$Ph=γ-aminosulfone with phenyl terminus
γ-$CO_2$H=γ-aminocarboxylate
γ-PEt=γ-aminophosphonate
γ-AM=γ-aminoamide
γ-Ar(sub)=γ-aminoaromatic compound (substituted as appropriate)
β-$SO_2$Ph=β-aminosulone with phenyl substituent
α-$SO_2$Ph=α-aminosulfone with phenyl substituent
Hph=homophenylalanine
PSMP=diethyl phenylsulfonylmethylenephosphonate
Np2=2-naphthylalanine
$SO_2$2Np=sulfone with 2-maphthyl terminus
Phac=phenylacetyl
β-Ala=β-alanine
MeOSuc=methoxysuccinyl For instance, Mu-Phe-Hph-β-$SO_2$Ph where $Xaa_2$=Phe (phenylalanine) and $Xaa_1$=Hph (homophenylalanine), transformed to the β-amino phenyl sulfone according to the procedure described in the Examples.

Example 1

Synthesis of Cysteine Protease Inhibitor Containing a γ-Aminoester as the EWG Unless otherwise indicated, all reactions were performed under an inert atmosphere of argon or nitrogen at room temperature. THF was distilled from sodium benzophenone ketyl. All other solvents and commercially available reagents were used without further purification.

Synthesis of Ethyl (S)-4-(4-morpholinecarbonyl-phenylalanyl)-amino-6-phenylhexanoate, abbreviated Mu-Phe-Hph-γ-$CO_2$Et, was as follows. Unless otherwise noted, all reagents were obtained from Aldrich, Inc. 0.393 g of a 60% mineral oil dispersion (9.82 mmol) of sodium hydride was added to a solution of triethyl phosphonoacetate (2.20 g, 9.82 mmol) in THF (50 mL) at –10° C. The mixture was stirred for 15 minutes, whereupon a solution of Boc-homophenylalaninal (Boc-HphH) (2.35 g, 9.82 mmol, prepared by conversion of Boc-homophenylalanine (Synthetech) to its N,O-dimethylhydroxamide, using the Fehrentz method, followed by lithium aluminum hydride reduction) in THF (20 mL) was added. The mixture was stirred for 45 minutes. 1M HCl (30 mL) was added. The product was extracted with ethyl acetate (50 mL), washed with saturated aqueous $NaHCO_3$ (30 mL) dried over $MgSO_4$, filtered, and evaporated to dryness. The dried material was dissolved in $CH_2Cl_2$ (10 mL), and a 4.0M solution of HCl in dioxane (20 mL) was added. The mixture was stirred for 30 minutes. The solvents were removed under reduced pressure and the residue, ethyl (S)-4-amino-6-phenyl-2-hexenoate hydrochloride, was pumped dry.

4-Morpholinecarbonylphenylalanine (Mu-PheOH, 2.74 g, 9.82 mmol, prepared according to the method described in Esser, R. et. al., Arthritis & Rheumatism (1994), 37, 236) was dissolved in THF (50 mL) at –10° C. 4-methylmorpholine (1.08 mL, 9.82 mmol) was added, followed by isobutyl chloroformate (1.27 mL, 9.82 mmol). The mixed anhydride was stirred for 10 minutes, whereupon a solution of ethyl (S)-4-amino-6-phenyl-2-hexenoate hydrochloride from the previous step in DMF (10 mL) was added, followed by 4-methylmorpholine (1.08 mL, 9.82 mmol). The mixture was stirred for 1 hour. 1M HCl (50 mL) was added. The product was extracted with ethyl acetate (100 mL), washed with saturated aqueous $NaHCO_3$ (50 mL), dried over $MgSO_4$ and decolorizing charcoal (DARCO), filtered, and evaporated to dryness, giving 3.80 g of intermediate (80% yield from Boc-homophenylalaninal).

To a solution of this intermediate (1.45 g, 3.09 mmol) in ethanol (25 mL) was added 5% palladium on active carbon (0.5 g). The mixture was reduced on a Parr hydrogenator for 36 hours. The solution was filtered and the solvent was removed under reduced pressure, giving 1.19 g (82%) of the product.

Thin-layer chromatography (TLC) was performed on each sample. Visualization was accomplished by means of UV light at 254 nm, followed by ninhydrin, bromocresol green, or p-anisaldehyde stain. The retention factor (Rf) of the Mu-Phe-Hph-γ-$CO_2$Et was 0.35 (5% MeOH/$CH_2Cl_2$).

NMR spectra were recorded on a Varian Gemini 300 MHz instrument. All $^1$H NMR data of this and subsequent examples are reported as delta values in parts per million relative to internal tetramethylsilane, peak assignments in boldface. The following abbreviations are used: s, singlet; d, doublet; t, triplet; q, quartet; br, broad. An asterisk (*) implies that a signal is obscured or buried under another resonance.

Example 2

Synthesis of a Cysteine Protease Inhibitor Containing a γ-Aminosulfone as the EWG Synthesis of (S)-3-tert-butoxycarbonylamino-5-phenyl-1-phenylsulfonyl pentane (Boc-Hph-γ-$SO_2$Ph). To a solution of PSMP (8.87 g, 30.34 mmol) in THF (150 mL) at 0° C. was added sodium hydride (1.21 g of a 60% mineral oil dispersion). The mixture was stirred for 20 minutes, whereupon a solution of Boc-homophenylalaninal, synthesized by the method of Fehrentz and Castro, above, (7.99 g, 30.34 mmol) in THF (20 mL) was added. The solution was stirred for 30 minutes at 0° C. 1M HCl (100 mL) was added. The product was extracted into ethyl acetate (100 mL), washed with saturated aqueous sodium bicarbonate (100 mL), brine (50 mL), dried over $MgSO_4$, filtered, and the solvent was removed under reduced pressure. The residue was dissolved in ethanol (100 mL) and transferred to a Parr bottle charged with 5% palladium on active charcoal (0.92 g). The mixture was reduced on a Parr apparatus for 24 hours. The solution was filtered through Celite and the solvent was removed under reduced pressure. TLC of the product indicated a single product in quantitative yield, Rf=0.29 (30% ethyl acetate/hexane) that stained white with paraanisaldehyde spray.

Example 3

Synthesis of a Cysteine Protease Inhibitor Containing a γ-Aminosulfone as the EWG Synthesis of (S)-3-amino-5-phenyl-1-phenylsulfonyl-pentane hydrochloride (HCl.Hph-γ-$SO_2$Ph). To a solution of Boc-Hph-γ-SO₂Ph (12.24 g, 30.34 mmol) in dichloromethane (20 mL) was added hydrogen chloride in dioxane (50 mL of a 4.0M solution). The mixture was stirred for 90 minutes. The solvent was removed under reduced pressure, and the residue was dissolved in CH₂Cl₂ (50 mL). The solution was carefully added to ether (500 mL) with stirring. The solid was filtered, washed with ether (50 mL) and dried in vacuo.

Example 4

Synthesis of a Cysteine Protease Inhibitor Containing a γ-Aminosulfone as the EWG Synthesis of (S)-3-(4-morpholinecarbonylphenylalanyl)-amino-5-phenyl-1-phenylsulfonylpentane (Mu-Phe-Hph-γ-SO₂Ph). To a solution of Mu-PheOH (2.94 g, 10.56 mmol) in THF (75 mL) at −10° C. were added 4-methylmorpholine (1.16 mL, 10.56 mmol) and isobutyl chloroformate (1.37 mL, 10.56 mmol). The mixture was stirred for 5 minutes. (S)-(E)-3-amino-5-phenyl-1-phenylsulfonyl-1-pentene p-toluenesulfonate, synthesized by Wadsworth-Emmons condensation between Boc-homophenylalaninal and p-toluenesulfonic acid deprotection (5.00 g, 10.56 mmol) was added, followed by 4-methylmorpholine (1.16 mL, 10.56 mmol). The mixture was stirred for 45 minutes. The solution was diluted with ethyl acetate (100 mL), washed with 1M HCl (2×50 mL), saturated aqueous sodium bicarbonate (50 mL), brine (50 mL), dried over MgSO₄, filtered, and the solvent was removed under reduced pressure. The residue was crystallized from CH₂Cl₂/ether to give 4.27 g (72%) of intermediate. 1.17 g of this material (2.08 mmol) was dissolved in ethanol (25 mL). The solution was transferred to a Parr bottle charged with 5% palladium on active charcoal (0.30 g). The mixture was hydrogenated at room temperature overnight on a Parr shaker. Ethyl acetate was added to the suspension of product, which had crystallized from the reaction mixture. The solution was filtered and concentrated in vacuo, and then was recrystallized from CH₂Cl₂/hexane. M.p.=176°–178° C. TLC: (50% ethyl acetate/CH₂Cl₂) R_f=0.24.

Example 5

Synthesis of a Cysteine Protease Inhibitor Containing a γ-Aminosulfone as the EWG Synthesis of (S)-3-(4-morpholinecarbonyltyrosyl)-amino-5-phenyl-1-phenylsulfonylpentane (Mu-Tyr-Hph-γ-SO₂Ph). To a solution of 4-morpholinecarbonyltyrosine (Mu-TyrOH, synthesized according to the method described in Esser, R. et. al., Arthritis & Rheumatism (1994), 37, 236, 0.50 g, 1.70 mmol) in THF (10 mL) at −10° C. were added 4-methylmorpholine (0.187 mL, 1.70 mmol) and isobutyl chloroformate (0.220 mL, 1.70 mmol). After 5 minutes, HCl.Hph-γ-SO₂Ph (0.577 g, 1.70 mmol, described in Example 3) was added, followed by 4-methylmorpholine (0.187 mL, 1.70 mmol). The mixture was stirred for 45 minutes. Ethyl acetate (50 mL) was added. The solution was washed with 1M HCl, saturated aqueous sodium bicarbonate, and brine (30 mL each), dried over MgSO₄, filtered, and the solvent was removed under reduced pressure. The residue was precipitated from CH₂Cl₂/ether to give 0.58 g (59%) of Mu-Tyr-Hph-γ-SO₂Ph. M.p. 104°–107° C. TLC: (10% MeOH/CH₂Cl₂) R_f=0.59.

Example 6

Synthesis of a Cysteine Protease Inhibitor Containing a γ-Aminosulfone as the EWG Synthesis of (S)-3-(4-morphlinecarbonyl-2-naphthyl-alanyl)amino-5-phenyl-1-(2-naphthylsulfonyl)pentane (Mu-Np2-Hph-γ-SO₂2Np). 2-naphthalenethiol (9.64 g, 60.16 mmol) was dissolved in toluene (75 mL). Paraformaldehyde (3.97 g, 132 mmol) and HCl/dioxane (33 mL of a 4.0M solution) were added. The mixture was stirred for several days at room temperature. The solvent was removed under reduced pressure, and the residue was suspended in hexane (200 mL), dried over MgSO₄, filtered, and evaporated to dryness. This material, crude chloromethyl 2-naphthyl sulfide, was combined with triethyl phosphite (10.93 g, 65 mmol) and was heated at reflux for 4 hours. The mixture was cooled to room temperature, diluted with ether (200 mL), washed with 1M HCl, saturated aqueous sodium bicarbonate, and brine (150 mL each), dried over MgSO₄, filtered, and concentrated in vacuo to give 17.35 g (93% crude yield) of diethyl 2-naphthylthiomethylene phosphonate. This material was dissolved in CH₂Cl₂ (300 mL) and cooled to 0° C. Peracetic acid (23.5 mL of a 32% dilute acetic acid solution (Aldrich Chemical Co.) was carefully added. The mixture was stirred overnight while warming to room temperature. The solution was washed with freshly prepared, saturated aqueous sodium bisulfite solution (100 mL), then with several portions of saturated aqueous sodium bicarbonate, until the aqueous phase became basic. The organic phase was dried over MgSO₄, filtered, and the solvent was removed under reduced pressure. Chromatography on 60–200 mesh silica gel (0–10% ethyl acetate/CH₂Cl₂) afforded 6.5 g (34%) of the pure Wadsworth-Emmons reagent, diethyl 2-naphthylsulfonyl-methylene phosphonate along with an approximately equal mass of impure material. TLC: (20% ethyl acetate/CH₂Cl₂) R_f=0.37.

To a solution of diethyl 2-naphthylsulfonylmethylene phosphonate (3.91 g, 11.42 mmol) in THF (60 mL) at 0° C. was added sodium hydride (0.457 g of a 60% mineral oil dispersion. The mixture was stirred for 15 minutes, whereupon a solution of Boc-homophenylalaninal (3.00 g, 11.42 mmol) in THF (5 mL) was added. The mixture was stirred for 30 minutes. 1M HCl (100 mL) was added. The product was extracted with ethyl acetate (100 mL), washed with saturated aqueous sodium bicarbonate (75 mL), brine (50 mL), dried over MgSO₄, filtered, and the solvent was removed under reduced pressure. The residue was dissolved in dichloromethane (10 mL), to which was added HCl/dioxane (25 mL of a 4.0M solution). The mixture was stirred at room temperature for 1 hour, poured into ether (300 mL), and filtered. The solids were washed with ether (2×50 mL) and dried in vacuo to give 3.30 g (74% from Boc-homophenylalaninal) of (S)-(E)-3-amino-5-phenyl-1-(2-naphthylsulfonyl)-1-pentene.

To a solution of Boc-2-naphthylalanine (2.68 g, 8.51 mmol, (Synthetech, Oregon) in THF (50 mL) at −10° C. were added 4-methylmorpholine (0.936 mL, 8.51 mmol) and isobutyl chloroformate (1.103 mL, 8.51 mmol). The mixture was stirred for 5 minutes, whereupon (S)-(E)-3-amino-5-phenyl-1-(2-naphthylsulfonyl)-1-pentene (3.30 g, 8.51 mmol) was added, followed by 4-methylmorpholine (0.936 mL, 8.51 mmol). The mixture was stirred for 45 minutes, diluted with ethyl acetate (100 mL), washed with 1M HCl (50 mL), saturated aqueous sodium bicarbonate (50 mL), and brine (50 mL), dried over MgSO₄, filtered, and the solvent was removed under reduced pressure. The intermediate, (S)-(E)-3-(tert-butoxycarbonyl-2-naphthylalanyl)amino-5-phenyl-1-(2-naphthylsulfonyl)-1-pentene, was crystallized from a suitable mixture CH₂Cl₂/ether/hexane in 69% yield. The resulting material (3.83 g, 5.90 mmol) was dissolved in CH₂Cl₂ (5 mL) and was treated with HCl/dioxane (15 mL of a 4.0M solution. The mixture was stirred at room temperature for 1 hour. The solution was poured, with stirring, into ether (500 mL) and filtered. The solids were washed with ether (2×50 mL) and dried in vacuo to give the intermediate, (S)-(E)-3-(2-naphthylalanyl)-amino-5-phenyl-1-(2-naphthylsulfonyl)-1-pentene, 3.41 g, 99% yield.

2.00 g of this material (3.42 mmol) was dissolved in THF (15 mL), and cooled to 0° C. 4-methylmorpholine-carbonyl chloride (0.400 mL, 3.42 mmol) and triethylamine (0.953 mmol) were added. The mixture was stirred for 1 hour at 0° C., and then at room temperature for 2 hours. Ethyl acetate (50 mL) was added. The solution was washed with 1M HCl (30 mL), saturated aqueous sodium bicarbonate (30 mL), brine (30 mL), dried over $MgSO_4$, filtered, and evaporated to dryness, giving 1.58 g (69%) of intermediate, (S)-(E)-3-(4-morpholinecarbonyl-2-naphthylalanyl)amino-5-phenyl-1-(2-naphthylsulfonyl)-1-pentene. TLC: (50% ethyl acetate/hexane) $R_f$=0.37.

0.73 g (1.10 mmol) of this material was dissolved in ethanol (20 mL) and transferred to a Parr bottle charged with 5% palladium on carbon (0.30 g). The mixture was reduced on a Parr hydrogenator for 36 hours. The solution was filtered and the solvent was removed under reduced pressure. The product was purified by column chromatography on 60–200 mesh silica gel (50% ethyl acetate/$CH_2Cl_2$ as eluent) to give 0.14 g (19%) of pure product, Mu-Np2-Hph-γ-$SO_2$Np, along with impure material. TLC: (50% ethyl acetate/$CH_2Cl_2$) $R_f$=0.34.

Example 7

Synthesis of a Cysteine Protease Inhibitor Containing a γ-Aminosulfone as the EWG Synthesis of 3-acetyltyrosylvalylalanylamino-4-hydroxy-carbonyl-1-phenylsulfonylbutane (Ac-Tyr-Val-Ala-Asp-γ-$SO_2$Ph). Sodium hydride (0.489 g of a 60% mineral oil dispersion, 12.23 mmol) was added to a solution of diethyl phenylsulfonylmethylene phosphonate (3.58 g, 12.23 mmol) in 50 mL of THF at 0° C. The mixture was stirred for 15 minutes. A solution of Boc-AspH(1-Ot-Bu), (3.04 gm, 11.12 mmol, prepared by converting Boc-Asp(β-O-t-Bu) to its N,O-dimethyldroxamide and reducing with lithium aluminum hydride), in THF (10 mL) was added. The mixture was stirred for 1 hour, whereupon 1M HCl (30 mL) was added. The product was extracted with ethyl acetate (100 mL), washed with saturated aqueous $NaHCO_3$ (30 mL), brine (30 mL), dried over $MgSO_4$, filtered, and evaporated to dryness, giving the intermediate. Chromatography on silica gel (20–30% ethyl acetate/hexane, gradient elution) afforded 2.07 g 45%) of the intermediate, (S)-(E)-3-tert-butoxycarbonylamino-4-tert-butoxycarbonyl-1-phenylsulfonyl-1-butene. This material was dissolved in ether (2 mL) and was treated with a solution of anhydrous p-toluenesulfonic acid (1.0 g, 5.87 mmol) in ether (2 mL). The mixture was stirred at room temperature overnight, then diluted with ether (25 ml). The white precipitate, was filtered, washed with ether, and dried in vacuo to give 0.80 g (95%) of the next intermediate, (S)-(E)-3-amino-4-tert-butoxycarbonyl-1-phenylsulfonyl-1-butene-p-toluenesulfonate.

This material was coupled, using mixed anhydride chemistry, to Ac-Tyr-Val-AlaOH, itself prepared by standard peptide chemistry, giving the next intermediate, (S)-(E)-3-acetyltyrosylvalylalanylamino-4-tert-butoxycarbonyl-1-phenylsulfonyl-1-butene.

This material was treated with trifluoroacetic acid to remove the t-butyl ester of the aspartic acid side chain, giving (E)-3-acetyltyrosylvalylalanylamino-4-hydroxycarbonyl-1-phenylsulfonyl-1-butene. 0.28 g (0.444 mmol) of this material was dissolved in ethanol (10 mL). The solution was transferred to a Parr bottle, charged with 5% palladium on carbon (0.1 g). The solution was reduced on a Parr hydrogenator overnight. The solution was filtered and the solvent was removed under reduced pressure. The residue, when dissolved in methanol (5 mL) and diluted with 40× 1:1 $CH_2Cl_2$/ether, formed a gelatinous precipitate, which was collected on a Buchner funnel to give 0.18 g (64%) yield. The isomer ratio of S to R with respect to the Asp residue was estimated as approximately 3:1 based on the integration of the doublets associated with the aromatic region of the NMR as pertains to the Tyr residue.

Example 8

Synthesis of a Cysteine Protease Inhibitor with a γ-Aminocarboxylate as the EWG Synthesis of (S)-4-(4-morpholinecarbonylphenylalanyl)amino-6-phenylhexanoic acid, Mu-Phe-Hph-γ-$CO_2$H. To a solution of Mu-Phe-Hph-γ-$CO_2$Et, prepared according to the procedure described in Example 1 (0.5g, 1.06 mmole) was added aqueous NaOH (1 mL of a 2M solution). After 4 hr the reaction was complete. 1M HCl (4mL) was added along with water (10 mL). The product was extracted with $CH_2Cl_2$ (2×10 mL), THF (15dried over $MgSO_4$, the solvent was removed under reduced pressure, and the residue, Mu-Phe-Hph-γ-$CO_2$H, was pumped to a solid Yield=0.30g (60%).

Example 9

Synthesis of a Cysteine Protease Inhibitor with a γ-Aminophosphonate as the EWG Synthesis of diethyl (S)-4-(4-morpholinecarbonyl-phenylalanyl)amino-6-phenylhexanephosphonate (Mu-Phe-Hph-γ-$SO_2$Ph) was as follows. To a solution of tetraethyl methylenediphosphonate (2.00 g, 6.94 mmol) in THF (30 mL) was added sodium hydride (0.278 g of a 60% mineral oil dispersion, 6.94 mmol). The mixture effervesced rapidly and then clarified. After 5 minutes, a solution of Boc-HphH (1.83 g, 6.94 mmol) in THF (5 mL) was added. The mixture was stirred for 1 hour. 1M HCl (20 mL) was added. The product was extracted into ethyl acetate (50 mL), washed with saturated aqueous $NaHCO_3$ (20 mL), brine (10 mL), dried over $MgSO_4$, filtered, and evaporated to dryness, giving 2.46 g (89%) of intermediate, diethyl (S)-(E)-4-tert-butoxycarbonylamino-6-phenyl-2-hexenephosphonate. To a solution of this material in $CH_2Cl_2$ (3 mL) was added 10 mL of a 4.0M solution of HCl in dioxane. The mixture was stirred at room temperature for 1.5 hours. The solvents were removed under reduced pressure and the residue was dissolved in methanol (10 mL). The solution was poured into ether (400 mL). The precipitate was collected on a Buchner funnel, washed with ether (2×20 mL), and was pumped dry to give 1.25 g (60%) of intermediate, diethyl (S)-(E)-4-amino-6-phenyl-2-hexenephosphonate hydrochloride. To a solution of Mu-PheOH (1.04 g, 3.74 mmol) in THF (15 mL) at −10° C. was added 4-methylmorpholine (0.412 mL, 3.74 mmol), followed by isobutyl chloroformate (0.486 mL, 3.74 mmol). The mixed anhydride was stirred for 5 minutes, whereupon a solution of (S)-(E)-4-amino-6-phenyl-2-hexene-phosphonate hydrochloride (1.25 g, 3.74 mmol) in DMF (5 mL) was added, followed by 4-methylmorpholine (0.412 mL, 3.74 mmol). The mixture was stirred for 1 hour. Ethyl acetate (50 mL) was added. The solution was washed with 1M HCl (25 mL), saturated aqueous $NaHCO_3$ (25 mL), and brine (10 mL), dried over MgSO$_4$, filtered, and evaporated to dryness. The product, upon treatment with CH$_2$Cl$_2$/ether/hexane (315 mL in a 15:200:100 ratio) formed an oil that solidified on drying in vacuo to give 1.44 g (69%) of diethyl (S)-(E)-4-(4-morpholinecarbonyl-phenylalanyl)-amino-6-phenyl-2-hexenephosphonate. 0.85 g of this material was dissolved in ethanol (10 mL) and was transferred to a Parr bottle charged with 5% palladium on active charcoal. The solution was reduced on a Parr hydrogenator for 36 hours. The solution was then filtered through Celite, and the solvent was removed under reduced pressure to give 0.66 g (76%) of the final product as an oil. TLC: (5% MeOH/CH$_2$Cl$_2$) R$_f$=0.27.

Example 10

Synthesis of a Cysteine Protease Inhibitor with a γ-Aminoamide as the EWG

Synthesis of benzyl (S)-3-(4-morpholinecarbonylphenyl-alanyl)-amino-6-phenylhexanamide (Mu-Phe-Hph-γ-AMBzl). The Wadsworth-Emmons reagent diethyl benzylamido-carbonylmethylenephosphonate was synthesized in two steps, first by saponification of triethyl phosphonoacetate to diethyl phosphonoacetic acid, which then was dissolved in ethyl acetate to a 0.2M concentration, treated with an equivalent of benzylamine, 0.1 equivalents of 4-dimethylamino-pyridine, and one equivalent of dicyclohexyl-carbodiimide. To a solution of this Wadsworth-Emmons reagent (2.59 g, 9.08 mmol) in THF (40 mL) at 0° C. was added sodium hydride (0.363 g of a 60% mineral oil dispersion, 9.08 mmol). The mixture was stirred at room temperature for 15 minutes, whereupon a solution of Boc-homophenylalaninal (2.39 g, 9.08 mmol) in THF (10 mL) was added. The mixture was stirred for 1 hour. 1M HCl (30 mL) was added. The product was extracted into ethyl acetate (100 mL), washed with saturated aqueous sodium bicarbonate (50 mL), brine (30 mL), dried over MgSO$_4$, filtered, concentrated, and crystallized from ether/hexane to give 1.81 g (51%) of benzyl (S)-(E)-3-tertbutoxycarbonylamino-6-phenyl-2-hexenamide. This material was dissolved in CH$_2$Cl$_2$ (5 mL). To the solution was added HCl/dioxane (10 mL of a 4.0M solution). The mixture was stirred for 3 hours at room temperature. The solvents were removed under reduced pressure. The residue was dissolved in methanol (5 mL) and poured into ether (300 mL), whereupon the intermediate, benzyl (S)-(E)-3-amino-6-phenyl-2-hexenamide hydrochloride, separated out as an oil, in 82% yield (1.25 g). To a solution of Mu-PheOH (1.05 g, 3.78 mmol) in THF (15 mL) at −10° C. were added 4-methylmorpholine (0.416 mL, 3.78 mmol) and isobutyl chloroformate (0.490 mL, 3.78 mmol). The mixture was stirred for 10 minutes, whereupon a solution of benzyl (S)-(E)-3-amino-6-phenyl-2-hexenamide hydrochloride (1.25 g, 3.78 mmol) in THF (3 mL) was added, followed by 4-methylmorpholine (0.416 mL, 3.78 mmol). The mixture was stirred for 45 minutes. Ethyl acetate (40 mL) was added. The solution was washed with 1M HCl (10 mL), saturated aqueous sodium bicarbonate (10 mL), brine (5 mL), dried over MgSO$_4$, filtered, and evaporated to dryness. The intermediate, benzyl (S)-(E)-3-(4-morpholinecarbonyl-phenylalanyl)amino-6-phenyl-2-hexenamide, was precipitated from CH$_2$Cl$_2$/ether in 56% yield. 0.48 g (0.865 mmol) of this material was dissolved in ethanol (10 mL) and transferred to a Parr bottle charged with 5% palladium on active carbon. The mixture was reduced on a Parr hydrogenator for 4 hours. The solution was filtered through Celite, and the solvent was removed under reduced pressure. The final product (Mu-Phe-Hph-γ-AMBzl) was crystallized from ethanol/hexane, giving 0.25 g (52%). TLC: (50% ethyl acetate/hexane) R$_f$=0.45.

Example 11

Synthesis of a Cysteine Protease Inhibitor with a γ-Aminoamide as the EWG

Synthesis of phenyl (S)-3-(4-morpholinecarbonylphenyl-alanyl)-amino-6-phenylhexanamide (Mu-Phe-Hph-γ-AMPh). To a solution of Mu-Phe-Hph-γ-CO$_2$H, (0.30g, as prepared according to Example 8), in THF (5 mL) at −10° C. was added triethylamine (90 μL, 1 eq.) followed by addition of isobutyl chloroformate (0.083 mL, 1 eq.). After 5 min, aniline (0.058 mL) was added. The cooling bath was removed and the reaction stirred at room temp for 2 hr. CH$_2$Cl$_2$ (30 mL) was added. The solution was washed with 1M HCl and saturated aqueous sodium bicarbonate (10 mL each), dried over MgSO$_4$, filtered, and the solvent was removed under reduced pressure. The residue was triturated with Et$_2$O, filtered, and dried in vacuo to give 0.29 g (85%) of the product, Mu-Phe-Hph-γ-AMPh. TLC (10% MeOH/CH$_2$Cl$_2$) R$_f$=0.70, strongly absorbs UV (254 nm), I$_2$.

Example 12

Synthesis of a Cysteine Protease Inhibitor with a γ-Aromatic as the EWG

Synthesis of (S)-4-aminophenyl-3-(4-morpholine-carbonylphenylalanyl)amino-5-phenylpentane hydrochloride, (Mu-Phe-hPhe-γ-C$_6$H$_4$NH$_2$.HCl).

Triphenylphosphine (38.17 g, 0.146 mole) and 4-nitrobenzyl chloride (25g, 0.146 mole) were dissolved in CH$_3$CN (100 mL) and heated at reflux for 2 hours, and then allowed to cool to room temperature. The reaction mixture was diluted with Et$_2$O (300 mL), the white solid was filtered, washed with Et$_2$O (200 mL), and dried in vacuo, giving 53.3 g (84%) of 4-nitrobenzyltriphenylphosphonium chloride as a single spot on TLC: (R$_f$=0.71, 4:1:1 butanol:acetic acid:water). $^1$H-NMR (d$_6$-DMSO): 5.40–5.50 (2H, d, CH$_2$P, J=20 Hz); 7.20–7.40 (2H, dd, aromatic); 7.40–7.80 (12H, m, aromatic); 7.90–8.00 (3H, m, aromatic); 8.10–8.20 (2H, d, aromatic).

To a stirred suspension of 4-nitrobenzyltriphenylphosphonium chloride (10.02 g, 23.1 mmol) in CH$_2$Cl$_2$ (100 mL) was added 4-methylmorpholine (2.54 mL, 23.1 mmol) was added. When all the solid had dissolved, Boc-HphH (4.04 g, 15.4 mmol) was added. After 24 hrs., the reaction mixture was diluted with CH$_2$Cl$_2$ (200 mL), and filtered. The filtrate was washed with 1M HCl (200 mL) saturated aqueous sodium bicarbonate (200 mL); dried over MgSO$_4$, filtered and concentrated under reduced pressure, giving 4.00 g of crude intermediate, a portion of which was purified by chromatography (gradient elution: 10–30% ethyl acetate/hexane) to permit NMR analysis of the intermediate, (S)-t-butoxycarbonyl-3-amino-1-(4-nitrophenyl)-5-phenyl-1-pentene. TLC: (30% EtOAc/hexane) R$_f$=0.49. To a solution of this material (2.76 g, 7.2 mmol) in Et$_2$O (25 mL), was added a solution of anhydrous p-toluenesulfonic acid (2.76 g, 16.0 mmol) in Et$_2$O (10 mL). The reaction was left to stir 16 hrs, filtered; washed solid with Et$_2$O (25 mL), and dried in vacuo, giving 2 g (61%) of (S)-3-amino-1-(4-nitrophenyl)-5-phenyl-1-pentene as a single spot on TLC: (Rf=0.49, 10% MeOH/CH$_2$Cl$_2$).

To a solution of Mu-PheOH (1.29 g, 4.63 mmol) in THF (20 mL) were added 4-methylmorpholine (0.51 mL, 4.63 mmol) and isobutyl chloroformate (0.61 mL, 4.63 mmol). After 3 minutes, a solution of (S) 3-amino-1-(4-nitrophenyl)-5-phenyl-1-pentene hydrochloride, prepared by HCl/dioxane-mediated deprotection of (S) 3-tert-butoxycarbonylamino-1-(4-nitrophenyl)-5-phenyl-1-pentene precursor, 1.34 g, 4.20 mmol) in $CH_2Cl_2$ (20 mL), followed by 4-methylmorpholine (0.51 mL, 4.63 mmol). The mixture was stirred overnight while warming to room temperature. The solution mixture was diluted with $CH_2Cl_2$ (100 mL), washed with 1M HCl (200 mL), saturated aqueous sodium bicarbonate (200 mL); dried over $MgSO_4$, filtered, and concentrated under reduced pressure to give a yellow oil. This material was crystallized from $CH_2Cl_2$/ether (2:100, 20 mL) to give 1.00 g (40%) of (S)-3-(4-morpholinecarbonylphenylalanyl)amino-1-(4-nitrophenyl)-5-phenyl-1-pentene as an approximately 4:1 E/Z mixture. 0.27 g (0.49 mmol) of this material was dissolved in ethanol (50 mL), transferred to a Parr bottle charged with 5% palladium on carbon (0.10 g) and reduced on a Parr hydrogenator for 8 hours/ The mixture was filtered and the solvent was removed under reduced pressure. The residue was dissolved in in 4:1 ether/$CH_2Cl_2$ (100 mL), to which HCl/dioxane (0.136 mL of a 4.0M solution) was added. The product, Mu-Phe-Hph-$\gamma$-$C_6H_4NH_2$·HCl, was filtered and dried in vacuo. Yield=0.15 g (54%). TLC: (10% methanol/$CH_2Cl_2$) $R_f$=0.31.

Example 13

Synthesis of a Cysteine Protease Inhibitor with a $\beta$-Aminosulfone as the EWG Synthesis of (S)-2-(4-morpholinecarbonylphenyl-alanyl)amino-4-phenyl-1-phenylsulfonylbutane (Mu-Phe-Hph-$\beta$-$SO_2$Ph). Preparation of Boc-homophenylalaninol (Boc-Hph-$\beta$-OH) and (S)-2-tert-butoxycarbonylamino-1-methanesulfonyloxy-1-phenylbutane (Boc-Hph-$\beta$-OMs or Boc-homophenylalaninol mesylate) followed a similar scheme to that reported by Spaltenstein, Carpino, Miyake, and Hopkins, above. To a solution of Boc-homophenylalanine (10.29 g, 36.84 mmol) in THF (100 mL) at $-10°$ C. were added 4-methylmorpholine (4.05 mL, 36.84 mmol) and isobutyl chloroformate (4.78 mL, 36.84 mmol). The solution was stirred for 10 minutes, and then was filtered. The filtrate was carefully added to a stirred solution of sodium borohydride (2.77 g, 73.67 mmol) in water (100 mL) at 0° C. The mixture was stirred for 30 minutes. Saturated aqueous sodium bicarbonate (200 mL) was added. The product was extracted with $CH_2Cl_2$ (2×100 mL), dried over $MgSO_4$, filtered, and the solvent was removed under reduced pressure to give 9.78 g (100%) Boc-homophenylalaninol. TLC: (30% ethyl acetate/hexane) Rf=0.15. 5.83 g (21.97 mmol) of this material was dissolved in $CH_2Cl_2$ (150 mL), cooled to 0° C., and treated with methanesulfonyl chloride (4.15 mL, 53.71 mmol), and triethylamine (9.24 mL, 66.3 mmol). The mixture was stirred for 30 minutes. Water (100 mL) was added; the mixture was stirred vigorously. The organic phase was separated, dried over $MgSO_4$, filtered, and the solvent was removed under reduced pressure, giving 7.31 g (97%) yield. TLC: (30% ethyl acetate/hexane) $R_f$=0.21. A similar procedure was employed to prepare the corresponding benzenesulfonate ester of Boc-Hph-$\beta$-OH.

To a solution of thiophenol (0.653 mL, 6.36 mmol) in THF (5 mL) was added sodium hydride (0.254 g, 6.36 mmol as a 60% mineral oil dispersion. The mixture was stirred for 10 minutes. A solution of Boc-homophenylalaninol benzenesulfonate (2.58 g, 6.36 mmol) in THF (5 mL) was added.

The solution was stirred at room temperature for 10 minutes. Methanol (2 mL) was then added, and the mixture was heated at reflux for 1 hour. The solution was cooled, diluted with 1M NaOH (25 mL), extracted with $CH_2Cl_2$ (100 mL), dried over $MgSO_4$, filtered, and the solvent was removed under reduced pressure. The residue was dissolved in $CH_2Cl_2$ (35 mL) and cooled to 0° C. To the solution was added 4-chloroperbenzoic acid (3.71 g, 13.99 mmol, estimated peracid content 65% by weight). The mixture was stirred for 1 hour, whereupon 10% NaOH (35 mL) and saturated aqueous $NaHSO_3$ (35 mL) were added. The mixture was extracted with $CH_2Cl_2$ (3×50 mL portions), dried over $MgSO_4$, filtered, and the solvent was removed under reduced pressure to give a waxy solid. (S)-2-tert-butoxycarbonylamino-4-phenyl-1-phenylsulfonylbutane. TLC: (30% ethyl acetate/hexane) $R_f$=0.32. 1.25 g of this material was dissolved in $CH_2Cl_2$ (5 mL) and treated with HCl/dioxane (5 mL of a 4.0M solution). The mixture was stirred for 2 hours at room temperature. The solution was poured into ether (200 mL), forming an oily residue. The supernatant was discarded. The residue was again dissolved in $CH_2Cl_2$ (10 mL), and poured into ether (200 mL). The intermediate, (S)-2-amino-4-phenyl-1-phenylsulfonylbutane hydrochloride precipitated out. The solid was filtered and dried in vacuo to give 0.40 g of material (38% yield from Boc-homophenylalaninol benzenesulfonate.

To a solution of Mu-PheOH (0.342 g, 1.23 mmol) in THF (10 mL) at -10° C. were added 4-methylmorpholine (0.135 mL, 1.23 mmol) and isobutyl chloroformate (0.159 mL, 1.23 mmol). The mixture was stirred for 10 minutes, whereupon (S)-2-amino-4-phenyl-1-phenylsulfonylbutane hydrochloride (0.40 g, 1.23 mmol) was added, followed by 4-methylmorpholine (0.135 mL, 1.23 mmol). The mixture was stirred for 45 minutes. 1M HCl (15 mL) was added. The product was extracted with ethyl acetate (30 mL), washed with saturated aqueous sodium bicarbonate (15 mL), brine (15 mL), dried over $MgSO_4$, filtered, and the solvent was removed under reduced pressure. The final product, Mu-Phe-Hph-$\beta$-$SO_2$Ph, weighed 0.68 g (100% yield).

Example 14

Synthesis of a Cysteine Protease Inhibitor with a $\beta$-Aminosulfone as the EWG Synthesis of (S)-2-tert-butoxycarbonylamino-4-phenyl-1-(1'-trimethylsilylethyl)-sulfonylbutane (Boc-Hph-$\beta$-$SO_2CH_2CH_2TMS$). To a solution of 2-trimethylsilylethanethiol (0.86 g, 6.41 mmol), synthesis described by Anderson, Ranasinghe, Palmer, and Fuchs, above) in THF (10 mL) was added sodium hydride (0.256 g, 6.41 mmol as a 60% mineral oil dispersion). The mixture was stirred for 10 minutes. Boc-homophenylalaninol mesylate (2.00 g, 5.82 mmol, synthesis described in Example 13, above) was added. The solution was stirred for 2 hours. Ethyl acetate (50 mL) was added. The solution was washed with 30 mL each of 1M HCl, saturated aqueous sodium bicarbonate, and brine, dried over $MgSO_4$, filtered, and the solvent was removed under reduced pressure, giving the intermediate (S)-2-tert-butoxycarbonylamino-4-phenylbutyl trimethylsilylethyl sulfide. TLC: (5% ethyl acetate/hexane) $R_f$=0.22. This material was dissolved in $CH_2Cl_2$ (50 mL), cooled to -10° C., and treated with 4-chloroperbenzoic acid (3.24 g, 12.22 mmol, estimated 65% peracid content). The mixture was stirred overnight. The suspension was filtered, and saturated aqueous $NaHSO_3$ (40 mL) and saturated aqueous sodium bicarbonate (50 mL) were carefully added

43 to the filtrate. The organic phase was separated, dried over MgSO$_4$, filtered, and the solvent was removed under reduced pressure to give the product, Boc-Hph-β-SO$_2$CH$_2$CH$_2$TMS in quantitative mass recovery from the mesylate. TLC: (30% ethyl acetate/hexane) R$_f$=0.49.

Example 15

Synthesis of a Cysteine Protease Inhibitor with a β-Aminosulfone as the EWG

Synthesis of (S)-2-(4-morpholinecarbonylphenylalanyl)-amino-1-chloromethylsulfonyl-4-phenylbutane (Mu-Phe-Hph-β-SO$_2$CH$_2$Cl. To a solution of Boc-Hph-β-SO$_2$CH$_2$CH$_2$TMS (0.90 g, 2.18 mmol as described in Example 14) in THF (2 mL) were added tetrabutylammonium fluoride (8.7 mL of a 1.0M THF solution) and several molecular sieves. The mixture was stirred overnight at room temperature. Bromochloromethane (5 mL) was added. The mixture was heated at reflux for 1 hour, cooled, and the volatile components were removed under reduced pressure. The residue was dissolved in ethyl acetate (75 mL), washed with 1M HCl (50 mL), dried over MgSO$_4$, filtered, and the solvent was removed under reduced pressure. The residue, crude (S)-2-tert-butoxycarbonylamino-1-chloromethylsulfonyl-4-phenylbutane, was dissolved in ether (3 mL). A solution of anhydrous 4-toluenesulfonic acid (0.80 g, 4.70 mmol) in ether (3 mL) was added. The mixture was stirred at room temperature overnight. Ether (100 mL) was added. The solid intermediate, (S)-2-amino-1-chloromethyl-sulfonyl-4-phenylbutane 4-toluenesulfonate (TsOH.Hph-β-SO$_2$CH$_2$Cl), was filtered, the solids were washed with ether (2×20 mL), and dried in vacuo to give 0.193 g of material (24% from Boc-Hph-β-SO$_2$CH$_2$CH$_2$TMS). To a solution of Mu-PheOH (0.109 g, 0.392 mmol) in THF (3 mL) at −10° C. were added 4-methylmorpholine (43 ML, 0.392 mmol) and isobutyl chloroformate (51 ML, 0.392 mmol). The mixture was stirred for 10 minutes, whereupon TsOH.Hph-β-SO$_2$CH$_2$Cl (0.17 g, 0.392 mmol) was added, followed by 4-methylmorpholine (43,uL, 0.392 mmol). The mixture was stirred for 45 minutes. Ethyl acetate (20 mL) was added. The solution was washed with 1M HCl, saturated aqueous sodium bicarbonate, and brine (2 mL each) dried over MgSO$_4$, filtered, and the solvent was removed under reduced pressure, to give the final product, Mu-Phe-Hph-β-SO$_2$CH$_2$Cl (90 mg, 48% yield.

Example 16

Synthesis of a Cysteine Protease Inhibitor with an α-Aminosulfone as the EWG

Synthesis of 1-(tert-butoxycarbonyl)amino-2-methyl-1-phenylsulfonylpropane (Boc-Val-α-SO$_2$Ph). To a stirred suspensionof t-butylcarbamate (2.34 g, 20 mmol) and sodium benzenesulfinate (3.28 g, 20 mmol) in water (20 mL) was added a solution of isobutyraldehyde (2.00 mL, 22 mmol) in formic acid (5 mL). The mixture was stirred at room temperature overnight. The precipitate was filtered, washed with water (2×50 mL) and crystallized from isopropanol/water to give 4.72 g (75%) of the product.

Example 17

Synthesis of a Cysteine Protease Inhibitor with an α-Aminosulfone as the EWG

Synthesis of 1-benzyloxycarbonylamino-3-phenyl-1-phenylsulfonylpropane (Z-Hph-α-SO$_2$Ph). To a suspension of sodium benzenesulfinate (10 g, 60.9 mmol) and benzyl carbamate (9.21 g, 60.9 mmol) in water (40 mL) was added hydrocinnamaldehyde (8.8 mL, 67 mmol) in formic acid (10 mL). The mixture was heated at 70° C. for 1 hour, then permitted to cool to room temperature overnight. The product crystallized out; it was filtered and recrystallized from hot isopropanol, giving 23 g (100%) yield. TLC: (30% ethyl acetate/hexane) R$_f$=0.37.

Example 18

Synthesis of a Cysteine Protease Inhibitor with an α-Aminosulfone as the EWG

Synthesis of (R)-1-(4-morpholinecarbonylphenylalanyl)amino-3-phenyl-1-phenylsulfonylpropane and (S)-1-(4-morpholinecarbonylphenylalanyl)amino-3-phenyl-1-phenylsulfonylpropane (Mu-Phe-Hph-α-SO$_2$Ph, epimers separated). Method A: Z-Hph-α-SO$_2$Ph (1.0 g, 2.44 mmol) was treated with 30% hydrogen bromide in acetic acid (5 mL). After 30 minutes, the mixture was diluted with ether (300 mL), filtered, washed with ether (2×30 mL), and dried in vacuo to give 0.74 g (86%) 1-amino-3-phenyl-1-phenylsulfonylpropane hydrobromide (HBr.Hph-α-SO$_2$Ph). To a solution of Mu-PheOH (0.64 g, 2.3 mmol) in THF (15 mL) were added 4-methylmorpholine (0.302 mL, 2.3 mmol) and isobutyl chloroformate (0.312 mL, 2.3 mmol). The mixture was stirred for 10 minutes. HBr.Hph-α-SO$_2$Ph (0.74 g, 2.1 mmol) was added, followed by 4-methylmorpholine (0.302 mL, 2.3 mmol). After 45 minutes, the mixture was diluted with ethyl acetate (30 mL), washed with 15 mL each of 1M HCl, saturated aqueous sodium bicarbonate, and brine, dried over MgSO$_4$, filtered, and the solvent was removed under reduced pressure to give 0.75 g (65%) of the product, Mu-Phe-Hph-α-SO$_2$Ph.

Method B: To a solution of phenylalanine amide hydrochloride (10 g, 50 mmol) in DMF (50 mL) and CH$_2$Cl$_2$ (50 mL) were added triethylamine (13.9 mL, 100 mmol) and 4-morpholinecarbonyl chloride (5.9 mL, 50 mmol). The mixture was stirred overnight. The solvents were removed under reduced pressure. The residue was dissolved in ethyl acetate (50 mL), and filtered. Ether was added to the filtrate until the solution became turbid. 7.2 g (80% yield) of the intermediate, 4-morpholinecarbonylphenylalanine amide (Mu-Phe-NH$_2$) crystallized from the solution after 3 days. To a solution of Mu-PheNH$_2$ (2.24 g, 8.1 mmol) in formic acid (5 mL) was added, with stirring, hydrocinnamaldehyde (1.17 mL, 8.9 mmol). The mixture was stirred for 5 hours, whereupon sodium benzenesulfinate (1.33 g, 8.1 mmol) was added. The mixture was quickly heated to reflux over a five minute period, and was allowed to cool to room temperature. The solution was then permitted to stir for three days. An equal volume of water was added. The product was extracted with CH$_2$Cl$_2$ (3×1 00 mL), dried over MgSO$_4$, filtered, and the solvent was removed under reduced pressure. The yield of product, diastereomeric (R)- and (S)-1-(4-morpholine-carbonylphenylalanyl)amino-3-phenylsulfonyl-1-phenyl-propane, was 3.9 g (90%). TLC (50% ethyl acetate/CH$_2$Cl$_2$) R$_f$=0.27.0.34. The diastereomers were separated by flash chromatography on 230–400 mesh silica gel (20–50% ethyl acetate/CH$_2$Cl$_2$, gradient elution).

Example 19

Inhibition of Cysteine Proteases with the Inhibitors of the Invention

Conditions for cathepsin B: 50 mM phosphate, pH 6.0, 2.5 mM EDTA, 2.5 mM DTT, substrate: [Z-Arg-Arg-AMC]

=50 mM (Km=190 mM). The assay at 250 was started by the addition of cat B (final concentration approx 10 nM) and the increase in fluorescence at 450 nm with excitation at 380 nm was followed over 2 min. The depression in the rate of substrate hydrolysis following addition of varying concentrations of inhibitors was noted. The assay was linear throughout the range observed. Duplicate runs were measured.

Conditions for cathepsin L: 50 mM acetate, pH 5.5, 2.5 mM EDTA, 2.5 mM DTT, substrate: [Z-Phe-Arg-AMC]=5 mM (Km=2 mM). The assay at 25°was started by the addition of cat L (final concentration approx 1 nM) and the increase in fluorescence at 450 nm with excitation at 380 nm was followed over 2 min. The depression in the rate of substrate hydrolysis following addition of varying concentrations of inhibitors was noted. The assay was linear throughout the range observed. Duplicate runs were measured.

Conditions for cathepsin S: 50 mM phosphate, pH 6.5, 2.5 mM EDTA, 2.5 mM DTT. substrate: [Z-Val-Val-Arg-AMC] =10 mM (Km=18 mM). The assay at 250 was started by the addition of cat S (final concentration approx 30 µM) and the increase in fluorescence at 450 nm with excitation at 380 nm was followed over 2 min. The depression in the rate of substrate hydrolysis following addition of varying concentrations of inhibitors was noted. The assay was linear throughout the range observed. Duplicate runs were measured.

Conditions for cruzain were the same as for cathepsin L with the exception that the Km for the substrate was 1 mM.

The respective $K_i$ values were estimated by using the Dixon plot as described by Irwin Segel in Enzyme Kinetics: Behavior and analysis of rapid equilibrium and steady-state enzyme systems, 1975, Wiley-Interscience Publication, John Wiley & Sons, New York.

The results are shown in Table 2.

Example 20

The following are representative phamaceutical formulation containing a cysteine protease inhibitor of this invention.

ORAL FORMULATION

A representative solution for oral administration contains:

| | |
|---|---|
| Cysteine protease inhibitor | 100 to 1000 mg |
| Citric Acid Monohydrate | 105 mg |
| Sodium Hydroxide | 18 mg |
| Flavoring | |
| Water | q.s. to 100 mL |

INTRAVENOUS FORMULATION

A representative solution for intravenous adminstration contains:

| | |
|---|---|
| Cysteine protease inhibitor | 10 to 100 mg |
| Dextrose Monohydrate | q.s. to make isotonic |
| Citric Acid Monohydrate | 1.05 mg |
| Sodium Hydroxide | 0.18 mg |
| Saline for Injection | q.s. to 1.0 mL |

TABLET FORMULATION

A representative tablet form may contain:

| | |
|---|---|
| Cysteine protease inhibitor | 1% |
| Microcrystalline Cellulose | 73% |
| Stearic Acid | 26% |
| Colloidal Silica | 1% |

TABLE 2

| Inhibitor | cathepsin B ($K_i$ µM) | cathepsin L | cathepsin S | cruzain |
|---|---|---|---|---|
| Mu—Phe—(DL)HphαSO$_2$Ph | 3,000 | 13 | 5 | 15 |
| Mu—Phe—HphαSO$_2$Ph | — | — | 2.6 | — |
| Mu—Phe—(DL)HphαSO$_2$Ph, | — | — | 3.7 | — |
| Mu—Leu—HphαSO$_2$Ph | 16 | 1.3 | 1.6 | 0.27 |
| Mu—Leu—HphαSO$_2$Bzl | 54 | 0.60 | 4.2 | 0.76 |
| Mu—Phe—HphαSO$_2$CH$_2$F | 170 | 1.5 | 2.8 | 2.0 |
| Mu—Phe—HphαSO$_2$Bzl | 77 | 1.2 | 5.2 | 0.92 |
| Mu—Phe—HphαSO$_2$CR$_3$ | 50 | 0.18 | 2.2 | 0.23 |
| Mu—Phe—HphβSO$_2$Ph | 1,100 | 29 | 0.94 | 5.7 |
| Mu—Phe—HphγSO$_2$Ph | 48 | 10 | 0.16 | 4.3 |
| Phac—Phe—HphγSO$_2$Ph | >>10 | 0.41 | 12.5 | 1.8 |
| Mu—Np2-HphγSO$_2$Np | 20 | 0.26 | 0.53 | 0.10 |
| Mu—Phe—HphγSO$_2$EtPh | 190 | 0.17 | 0.082 | 5.9 |
| Suc—Phe—HphγSO$_2$Ph | >1000 | 1.0 | 0.07 | 1.5 |
| MeOSuc—Phe—HphγSO$_2$Ph | 81 | 3.2 | 1.2 | 4.7 |
| Suc—Np2—HphγSO$_2$Ph | >1000 | 2.3 | 0.50 | 0.78 |
| Suc—Np2—HphγSO$_2$2Np | >1000 | 0.11 | 0.24 | 0.23 |
| Z—β-Ala—Phe—HphγSO$_2$Ph | 52 | 0.79 | 3.0 | 0.54 |
| β-Ala—Phe—HphγSO$_2$Ph | >>50 | 14 | 11 | 14 |
| Mu—Tyr—HphγSO$_2$Ph | — | 2.3 | 9.5 | 20 |
| Mu—Phe—HphγCO$_2$Et | 1.6 | 0.48 | 0.19 | 0.91 |
| Mu—Phe—HphγCONHPh | 2.6 | 2.0 | 1.3 | 0.13 |
| Mu—Phe—HphγCONHBzl | >>50 | 19 | 30 | 7.7 |
| Mu—Phe—HphγPO(O$_2$Et)$_2$ | 17 | 3.0 | 1.4 | 15 |
| Mu—Phe—Hph-γPh—OMe | 4.8 | 0.94 | 0.37 | 0.89 |
| Mu—Phe—Hph—γPh—NH$_2$ | >>50 | 2.9 | 9.1 | 3.0 |

We claim:

1. A cysteine protease inhibitor comprising a targeting group linked through a two carbon atom chain to an electron withdrawing group, wherein the dissociation constant for inhibition of the protease with said inhibitor (Ki) is no greater than about 100 µM.

2. A cysteine protease inhibitor comprising a targeting group linked either directly or through a linker selected from the group consisting of an intermediate carbon atom or a two carbon atom chain to a sulfonyl group, wherein the dissociation constant for inhibition of the protease with said inhibitor (Ki) is no greater than about 100 µM.

3. A compound of Formula I:

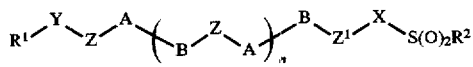

in which:

n is 0 to 13;

A-B represents a linkage selected from —C(O)NR$^3$—, —CH$_2$NR$^3$—, —C(O)CH$_2$— and —NR$^3$C(O)—, wherein R$^3$ is hydrogen or as defined below;

X represents a bond, methylene or the linkage —CH$_2$CH(R$^4$)—, wherein R$^4$ is hydrogen, alkyl or arylalkyl;

Y is —CH(R$^5$)— or —N(R$^5$)—, wherein R$^5$ is hydrogen or as defined below;

Z is —(CH$_2$)$_2$—, —C(R$^6$)(R$^7$)— or —N(R$^7$)—, wherein R$^6$ is hydrogen or methyl and R$^7$ is as defined below;

Z$^1$ is —(CH$_2$)$_2$—, —C(R$^6$)(R$^8$)— or —N(R$^8$)—, wherein R$^6$ is hydrogen or methyl and R$^8$ is as defined below;

R$^1$ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

R$^7$ and R$^8$ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof, cycloalkyl, cycloalkylalkyl, heteroaryl, heteroarylalkyl, a group selected from aryl and arylalkyl (which group is optionally substituted at its aryl ring with one to three radicals selected from hydroxy, amino, guanidino, halo, optionally halo-substituted alkyl, alkyloxy and aryl, or a protected derivative thereof) or together with an adjacent R$^3$ or R$^5$ forms a divalent radical selected from (C$_{3-4}$)methylene and 1,2-phenylenedimethylene (which radical is optionally substituted with hydroxy, or a protected derivative thereof, or oxo); and R$^2$ is hydrogen, alkyl (optionally substituted with one or more radicals selected from amino, halo, hydroxy, alkyloxy, nitro, alkylsulfonyl and arylsulfonyl, or a protected derivative thereof, cycloalkyl, cycloalkylalkyl or a group selected from aryl and arylalkyl (which group is optionally substituted at its aryl ring with one to two radicals selected from amino, guanidino, halo, hydroxy, optionally halo-substituted alkyl, alkyloxy, nitro, alkylsulfonyl and arylsulfonyl, or a protected derivative thereof; and the pharmaceutically acceptable salts, individual isomers and mixtures of isomers thereof.

4. The compound according to claim 3 wherein the dissociation constant for inhibition of a protease with said inhibitor (K$_i$) is no greater than about 100 µM.

5. The compound of claim 3 in which n is 0 to 5; A-B represents a linkage selected from —C(O)NR$^3$—; Y is —N(R$^5$)—; Z is —(CH$_2$)$_2$— or —C(R$^6$)(R$^7$)—; Z$^1$ is —CH(R$^8$)—; R$^1$ is hydrogen, alkyloxycarbonylalkanoyl of overall 3 to 10 carbon atoms, (C$_{1-9}$)alkoxycarbonyl, (C$_{2-10}$)alkanoyl (optionally substituted with a radical selected from carboxy, (C$_{1-9}$)alkyloxycarbonyl and hetero(C$_{4-8}$)cycloalkyl(C$_{2-10}$)alkanoylamin), (C$_{4-9}$)cycloalkylcarbonyl, hetero(C$_{4-8}$)cycloalkylcarbonyl (optionally substituted with a radical selected from hydroxy, (C$_{1-5}$)alkyl, (C$_{1-5}$)alkanoyl, (C$_{1-5}$)alkyloxycarbonyl, (C$_{6-10}$)aryl(C$_{1-5}$)alkyloxycarbonyl and hetero(C$_{4-8}$)cycloalkylcarbonyl), (C$_{6-10}$)aryl(C$_{1-5}$)alkyloxycarbonyl, carbamoyl, (C$_{1-5}$)alkylcarbamoyl, di(C$_{1-5}$)alkylcarbamoyl, (C$_{6-10}$)arylcarbamoyl, (C$_{6-10}$)aryl(C$_{1-5}$)alkylcarbamoyl, (C$_{6-10}$)aryl(C$_{1-5}$)alkanoyl, (C$_{7-11}$)aroyl, (C$_{1-5}$)alkylsulfonyl, di(C$_{1-5}$)alkylaminosulfonyl, (C$_{6-10}$)arylsulfonyl or hetero(C$_{1-5}$)arylsulfonyl; R$^8$ and R$^7$ are independently (C$_{3-7}$)cycloalkyl, (C$_{3-7}$)cycloalkyl(C$_{1-5}$)alkyl, pyridyl, thienyl, furyl, imidazolyl, indolyl, pyridyl(C$_{1-5}$)alkyl, thienyl(C$_{1-5}$)alkyl, furyl(C$_{1-5}$)alkyl, imidazolyl(C$_{1-6}$)alkyl, indolyl(C$_{1-6}$)alkyl, (C$_{1-5}$)alkyl, (optionally substituted with a radical selected from mercapto, carboxy, amino, methylthio, methylsulfonyl, carbamoyl, dimethylcarbamoyl, guanidino and hydroxy, or a protected derivative thereof), a group selected from phenyl, naphthyl, phenyl(C$_{1-6}$)alkyl, naphthyl(C$_{1-6}$)alkyl, (which group is optionally substituted at its aryl ring with one to three radicals selected from amino, hydroxy, chloro, bromo, fluoro, methyl, trifluoromethyl, methoxy and phenyl, or a protected derivative thereof) or together with an adjacent R$^3$ or R$^5$ forms a divalent radical selected from (C$_{3-4}$)methylene and 1,2-phenylenedimethylene (which radical is optionally substituted with hydroxy, or a protected derivative thereof, or oxo); R$^2$ is (C$_{1-5}$)alkyl (optionally substituted with one or two radicals selected from amino, chloro, bromo, fluoro, iodo, hydroxy and methoxy, or a protected derivative thereof, perhalo(C$_{1-5}$)alkyl, (C$_{3-7}$)cycloalkyl, (C$_{3-7}$)cycloalkyl(C$_{1-5}$)alkyl or a group selected from phenyl, pentafluorophenyl, naphthyl and phenyl(C$_{1-6}$)alkyl (which group is optionally substituted at its aryl ring with one to two radicals selected from amino, chloro, bromo, fluoro, hydroxy, methoxy and optionally halo-substituted methyl, or a protected derivative thereof) and R$^4$ is hydrogen, (C$_{1-5}$) alkyl or (C$_{6-10}$)aryl(C$_{1-5}$)alkyl.

6. The compound of claim 5 in which n is 0 to 2; Z is —(CH$_2$)$_2$— or —C(R$^6$)(R$^7$)— (with the proviso that when n is 0, Z is not —(CH$_2$)$_2$—); R$^1$ is hydrogen, (C$_{4-8}$) alkoxycarbonyl, (C$_{2-6}$)alkanoyl (optionally substituted with a radical selected from carboxy, (C$_{1-5}$)alkyloxycarbonyl and hetero(C$_{4-8}$)cycloalkyl(C$_{4-6}$)alkanoylamino), —C(O)NR$^{21}$R$^{22}$ wherein R$^{21}$ and R$^{22}$ together form aza(C$_{2-6}$)methylene, oxa(C$_{2-6}$)methylene or (C$_{3-7}$)methylene, (C$_{4}$-) cycloalkylcarbonyl, benzyloxycarbonyl, acetyl, benzoyl or dimethylaminosulfonyl; R$^8$ and R$^7$ are independently (C$_{5-6}$)cycloalkyl, (C$_{5-6}$)cycloalkylmethyl, 3-pyridyl, 2-thienyl, 2-furyl, 4-imidazolyl, 3-indolyl, 3-pyridylmethyl, 2-thienylmethyl, 2-furylmethyl, 4-imidazolylmethyl, 3-indolylmethyl, methoxy, acetoxy, (C$_{1-5}$)alkyl (optionally substituted with a radical selected from mercapto, carboxy, amino, methylthio, methylsulfonyl, carbamoyl, dimethylcarbamoyl, guanidino and hydroxy, or a protected derivative thereof, a group selected from phenyl, 1-naphthyl, 2-naphthyl, benzyl, 1-naphthylmethyl, 2-naphthylmethyl and 2-phenylethyl (which group is optionally substituted at its aryl ring with one radical selected from hydroxy, amino, chloro, bromo and fluoro, or a protected form thereof) or together with an adjacent $R^3$ or $R^1$ forms a divalent radical selected from $(C_{3-4})$methylene and 1,2-phenylenedimethylene (which radical is optionally substituted with hydroxy, or a protected derivative thereof, or oxo); $R^2$ is $(C_{1-5})$alkyl (optionally substituted with one or two radicals selected from amino, chloro, bromo, fluoro and hydroxy, or a protected derivative thereof, perfluoro($C_{1-5}$) alkyl, ($C_{5-6}$)cycloalkyl, ($C_{5-6}$)cycloalkylmethyl or a group selected from phenyl, naphthyl and benzyl (which group is optionally substituted with one radical selected from amino hydroxy, chloro, bromo or fluoro, or a protected derivative thereof and $R^4$ is hydrogen or methyl.

7. The compound of claim 4 in which n is 0 to 1; Z is —C($R^6$)($R^7$)—, $R^1$ is hydrogen, tert-butoxycarbonyl, benzyloxycarbonyl, acetyl, 3-carboxypropionyl, 3-methoxycarbonylpropionyl, biotinylaminohexanoyl, phenylacetyl, benzoyl, dimethylaminosulfonyl, benzylsulfonyl, 1-piperizinylcarbonyl, 4-methyl-1-piperazinylcarbonyl or 4-morpholinylcarbonyl; $R^8$ is butyl, 2-phenylethyl, 2-methylsulfonylethyl, 2-tert-butoxycarbonylethyl, 2-tert-butoxycarbonylmethyl, 4-tert-butoxycarbonylaminobutyl, 4-benzoylaminobutyl or benzyloxymethyl; $R^2$ is methyl, trifluoromethyl, optionally substituted phenyl, 2-naphthyl or 2-phenylethyl; $R^4$ is hydrogen; and $R^7$ is 3-pyridylmethyl, 2-thienylmethyl, 2-furylmethyl, 4-imidazolylmethyl, 3-indolylmethyl, $(C_{1-5})$ alkyl (optionally substituted with a radical selected from mercapto, carboxy, amino, methylthio, methylsulfonyl, carbamoyl, dimethylcarbamoyl, guanidino and hydroxy, or a protected derivative thereof, a group selected from benzyl, 1-naphthylmethyl, 2-naphthylmethyl and 2-phenylethyl (which group is optionally substituted at its aryl ring with one radical selected from hydroxy, amino, chloro, bromo and fluoro, or a protected form thereof) or together with an adjacent $R^3$ or $R^5$ forms a divalent radical selected from $(C_{3-4})$methylene and 1,2-phenylenedimethylene (which radical is optionally substituted with hydroxy, or a protected derivative thereof, or oxo).

8. The compound of claim 7 in which n is 0; $R^3$, $R^5$ and $R^8$ are each hydrogen; $R^1$ is hydrogen, tert-butxoycarbonyl, benzyloxycarbonyl, biotinylaminohexanoyl, benzoyl, 1-piperiziny-carbonyl, 4-methyl-1-piperazinylcarbonyl or 4-morpholinylcarbonyl; $R^8$ is butyl, 2-phenylethyl or 2-methylsulfonylethyl; $R^2$ is phenyl, 1-naphthyl or 2-phenylethyl; and $R^7$ is $(C_{1-5})$alkyl, 2-methylsulfonylethyl, optionally substituted benzyl, 1-naphthylmethyl, 2-naphthylmethyl, 3-pyridinylmethyl or 2-methylsulfonylethyl.

9. The compound of claim 8 in which $R^1$ is 1-piperizinylcarbonyl, 4-methyl-1-piperazincarbonyl or 4-morpholinylcarbonyl; $R^8$ is 2-phenylethyl; $R^2$ is phenyl or naphth-2-yl; and $R^7$ is optionally substituted benzyl, 1-naphthylmethyl or 2-naphthylmethyl.

10. The compound of claim 9 in which X represents a bond, $R^1$ is 4-morpholinylcarbonyl, $R^8$ is 2-phenylethyl, $R^2$ is phenyl and $R^7$ is benzyl, namely $N^2$-(4-morpholinylcarbonyl)-$N^1$-(3-phenyl-1-phenylsulfonylpropyl)-L-phenylalaninamide.

11. The compound of claim 9 in which X represents methylene, $R^1$ is 4-morpholinylcarbonyl, $R^1$ is 2-phenylethyl, $R^2$ is phenyl and $R^7$ is benzyl, namely $N^2$-(4-morpholinylcarbonyl)-$N^1$-(3-phenyl-1S-phenylsulfonylmethylpropyl)-L-phenylalaninamide.

12. The compound of claim 9 in which X represents —$CH_2CH(R^4)$— wherein $R^4$ is hydrogen, $R^1$ is 4-morpholinylcarbonyl, $R^8$ is 2-phenylethyl, $R^2$ is 2-naphthyl and $R^7$ is 2-naphthylmethyl, namely $N^2$-(4-morpholinylcarbonyl)-$N^1$-{3-phenyl-1S-[2-(2-naphthylsulfonyl)ethyl]propyl}-β-(2-naphthyl)-L-alaninamide.

13. The compound of claim 9 in which X represents —$CH_2CH(R^4)$— wherein $R^4$ is hydrogen, $R^1$ is 4-morpholinylcarbonyl, $R^8$ is 2-phenylethyl, $R^2$ is phenyl and $R^7$ is 4-hydroxybenzyl, namely $N^2$-(4-morpholinylcarbonyl)-$N^1$-{3-phenyl-1S-[2-(2-naphthylsulfonyl)ethyl]propyl}-L-tyrosinamide.

14. The compound of claim 9 in which X represents —$CH_2CH(R^4)$— wherein $R^4$ is hydrogen, $R^1$ is 4-morpholinylcarbonyl, $R^8$ is 2-phenylethyl, $R^2$ is phenyl and $R^7$ is benzyl, namely $N^2$-(4-morpholinylcarbonyl)-$N^1$-[3-phenyl-1S-(2-phenylsulfonylethyl)propyl]-L-phenylalaninamide.

15. A compound of Formula II:

in which:

n is 0 to 13;

A-B represents a linkage selected from —C(O)$NR^3$—, —$CH_2NR^3$—, —C(O)$CH_2$— and —$NR^3$C(O)—, wherein $R^3$ is hydrogen or as defined below;

Y is —CH($R^5$)— or —N($R^5$)—, wherein $R^5$ is hydrogen or as defined below;

Z is —$(CH_2)_2$—, —C($R^6$)($R^7$)— or —N($R^7$)—, wherein $R^6$ is hydrogen or methyl and $R^7$ is as defined below;

$Z^1$ is —$(CH_2)_2$—, —C($R^6$)($R^8$)— or —N($R^8$)—, wherein $R^6$ is hydrogen or methyl and $R^8$ is as defined below;

$R^1$ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

$R^7$ and $R^8$ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof), cycloalkyl, cycloalkylalkyl, heteroaryl, heteroarylalkyl, a group selected from aryl and arylalkyl (which group is optionally substituted at its aryl ring with one to three radicals selected from hydroxy, amino, guanidino, halo, optionally halo-substituted alkyl, alkyloxy and aryl, or a protected derivative thereof) or together with an adjacent $R^3$ or $R^5$ forms a divalent radical selected from a divalent radical selected from $(C_{3-4})$methylene and 1,2-phenylenedimethylene (which radical is optionally substituted with hydroxy, or a protected derivative thereof, or oxo); and $R^9$ is cyano, —C(O)$OR^{10}$, —P(O)($OR^{10}$)$_2$, —S(O)(N$R^{10}$)$R^{10}$, C(O)$R^{11}$, —S(O)$R^{11}$, —C(O)N$R^{12}R^{13}$, —S(O)$_2$NR$^{12}$R$^{13}$, —C(O)NHR$^{14}$ or —S(O)$_2$NHR$^{14}$, wherein each R$^{10}$ is independently hydrogen, alkyl (optionally substituted with one or more radicals selected from amino, halo, hydroxy, alkyloxy, nitro, alkylsulfonyl and arylsulfonyl, or a protected derivative thereof), cycloalkyl, cycloalkylalkyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof), R$^{11}$ is hydrogen, alkyl, perfluoroalkyl, cycloalkyl, cycloalkylalkyl, perfluoroaryl, perfluoroarylakyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof), R$^{12}$ and R$^{13}$ are independently hydrogen, alkyl, cycloalkyl, cycloalkylalkyl, aryl or aralkyl and R$^{14}$ is —C(O)OR$^{10}$, in which R$^{10}$ is as defined above, or a group selected from Formula (a) and (b):

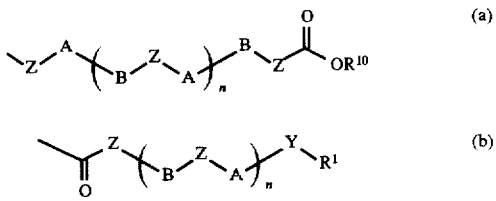

wherein each n, A, B, Y, Z, R$^1$ and R$^{10}$ are as defined above; and the pharmaceutically acceptable salts, individual isomers and mixtures of isomers thereof.

16. The compound of claim 15 in which each n is 0 to 5; each A-B represents a linkage selected from —C(O)NR$^3$—; each Y is —N(R$^5$)—; each Z is —(CH$_2$)$_2$— or —C(R$^6$)(R$^7$)—; Z$^1$ is —CH(R$^8$)—; each R$^1$ is independently hydrogen, alkyloxycarbonylalkanoyl of overall 3 to 10 carbon atoms, (C$_{1-9}$)alkoxycarbonyl, (C$_{2-10}$)alkanoyl (optionally substituted with a radical selected from carboxy, (C$_{1-9}$) alkyloxycarbonyl and hetero(C$_{4-8}$)cycloalkyl(C$_{2-10}$) alkanoylamino), (C$_{4-9}$)cycloalkylcarbonyl, hetero(C$_{4-8}$) cycloalkylcarbonyl (optionally substituted with a radical selected from hydroxy, (C$_{1-5}$)alkyl, (C$_{1-5}$)alkanoyl, (C$_{1-5}$) alkyloxycarbonyl, (C$_{6-10}$)aryl(C$_{1-5}$)alkyloxycarbonyl and hetero(C$_{4-8}$)cycloalkylcarbonyl), (C$_{6-10}$)aryl(C$_{1-5}$) alkyloxycarbonyl, carbamoyl, (C$_{1-5}$)alkylcarbamoyl, di(C$_{1-5}$)alkylcarbamoyl, (C$_{6-10}$)arylcarbamoyl, (C$_{6-10}$)aryl(C$_{1-5}$) alkylcarbamoyl, (C$_{6-10}$)aryl(C$_{1-5}$)alkanoyl, (C$_{7-11}$)aroyl, (C$_{1-5}$)alkylsulfonyl, di(C$_{1-5}$)alkylaminosulfonyl, (C$_{6-10}$) arylsulfonyl or hetero(C$_{5-8}$)arylsulfonyl; R$^8$ and R$^7$ are independently (C$_{3-7}$)cycloalkyl, (C$_{3-7}$)cycloalkyl(C$_{1-5}$)alkyl, pyridyl, thienyl, furyl, imidazolyl, indolyl, pyridyl(C$_{1-6}$) alkyl, thienyl(C$_{1-6}$)alkyl, furyl(C$_{1-6}$)alkyl, imidazolyl(C$_{1-6}$) alkyl, indolyl(C$_{1-6}$)alkyl, a group selected from (C$_{1-5}$)alkyl, (C$_{2-6}$)alkyloxy and (C$_{1-5}$)alkanoyloxy (which group is optionally substituted with a radical selected from mercapto, carboxy, amino, methylthio, methylsulfonyl, carbamoyl, dimethylcarbamoyl, guanidino and hydroxy, or a protected derivative thereof), a group selected from phenyl, naphthyl, phenyl(C$_{1-6}$)alkyl, naphthyl(C$_{1-6}$)alkyl, (which group is optionally substituted at its aryl ring with one to three radicals selected from amino, hydroxy, chloro, bromo, fluoro, methyl, trifluoromethyl, methoxy and phenyl, or a protected derivative thereof) or together with an adjacent R$^3$ or R$^5$ forms a divalent radical selected from (C$_{3-4}$)methylene and 1,2-phenylenedimethylene (which radical is optionally substituted with hydroxy, or a protected derivative thereof, or oxo); each R$^{10}$ is independently (C$_{1-5}$)alkyl (optionally substituted with one or two radicals selected from amino, chloro, bromo, fluoro, hydroxy and methoxy or a protected derivative thereof), (C$_{3-7}$)cycloalkyl, (C$_{3-7}$)cycloalkyl(C$_{1-5}$) alkyl, or a group selected from phenyl or phenyl(C$_{1-6}$)alkyl (which group is optionally substituted at its phenyl ring with one to two radicals selected from amino, chloro, bromo, fluoro, hydroxy, methoxy and optionally halo-substituted methyl, or a protected derivative thereof; R$^{11}$ is independently (C$_{1-5}$)alkyl, (C$_{3-7}$)cycloalkyl, (C$_{3-7}$)cycloalkyl(C$_{1-5}$) alkyl or a group selected from phenyl, and phenyl(C$_{1-6}$)alkyl (which group is optionally substituted at its aryl ring with one to two radicals selected from amino, chloro, bromo, fluoro, hydroxy, methyl, trifluoromethyl and methoxy); and R$^{12}$ and R$^{13}$ are independently (C$_{1-5}$)alkyl, (C$_{3-7}$)cycloalkyl, (C$_{3-7}$)cycloalkyl (C$_{1-5}$)alkyl or a group selected from phenyl and phenyl(C$_{1-6}$)alkyl (which group is optionally substituted at its phenyl ring with one to two radicals selected from amino, chloro, bromo, fluoro, hydroxy, methoxy and optionally halo-substituted methyl).

17. The compound of claim 16 in which each n is 0 to 2; Z is —(CH$_2$)$_2$— or —C(R$^6$)(R$^7$)— (with the proviso that when n is 0, Z is not —(CH$_2$)$_2$—); each R$^1$ is hydrogen, (C$_{4-8}$)alkoxycarbonyl, (C$_{2-6}$)alkanoyl (optionally substituted with a radical selected from carboxy, (C$_{1-5}$) alkyloxycarbonyl and hetero(C$_{4-8}$)cycloalkyl(C$_{4-6}$) alkanoylamino), —C(O)NR$^{21}$R$^{22}$ wherein R$^{21}$ and R$^{22}$ together form aza(C$_{2-6}$)methylene, oxa(C$_{2-6}$)methylene or (C$_{3-7}$)methylene, (C$_{4-8}$)cycloalkylcarbonyl, benzyloxycarbonyl, acetyl, benzoyl or dimethylaminosulfonyl; R$^8$ and R$^7$ are independently (C$_{5-6}$)cycloalkyl, (C$_{5-6}$) cycloalkylmethyl, 3-pyridyl, 2-thienyl, 2-furyl, 4-imidazolyl, 3-indolyl, 3-pyridylmethyl, 2-thienylmethyl, 2-furylmethyl, 4-imidazolylmethyl, 3-indolylmethyl, methoxy, acetoxy, a group selected from (C$_{1-5}$)alkyl (which group is optionally substituted with a radical selected from mercapto, carboxy, amino, methylthio, methylsulfonyl, carbamoyl, dimethylcarbamoyl, guanidino and hydroxy, or a protected derivative thereof), a group selected from phenyl, 1-naphthyl, 2-naphthyl, benzyl, 1-naphthylmethyl, 2-naphthylmethyl and 2-phenylethyl (which group is optionally substituted at its aryl ring with one radical selected from hydroxy, amino, chloro, bromo and fluoro, or a protected form thereof) or together with an adjacent R$^3$ or R$^5$ forms a divalent radical selected from (C$_{3-4}$)methylene and 1,2-phenylenedimethylene (which radical is optionally substituted with hydroxy, or a protected derivative thereof, or oxo); each R$^{10}$ is ethyl, (C$_{5-6}$)cycloalkyl, (C$_{5-6}$) cycloalkylmethyl or a group selected from phenyl and benzyl (which group is optionally substituted at its phenyl ring with one radical selected from amino hydroxy, chloro, bromo or fluoro, or a protected derivative thereof); R$^{11}$ is ethyl, cyclo(C$_{5-6}$)alkyl, cyclo(C$_{5-6}$)alkylmethyl or a group selected from phenyl and benzyl (which group is optionally substituted at its phenyl ring with one radical selected from amino hydroxy, chloro, bromo or fluoro, or a protected derivative thereof); and R$^{12}$ and R$^{13}$ are independently ethyl, (C$_{5-6}$)cycloalkyl, (C$_{5-6}$)cycloalkylmethyl or a group selected from phenyl and benzyl (which group is optionally substituted at its phenyl ring with one radical selected from amino hydroxy, chloro, bromo or fluoro, or a protected derivative thereof.

18. The compound of claim 17 in which each n is 0 to 1; Z is —C(R$^6$)(R$^7$)—; each R$^1$ is hydrogen, tert-butoxycarbonyl, benzyloxycarbonyl, acetyl, 3-carboxypropionyl, 3-methoxycarbonylpropionyl, biotinylaminohexanoyl, phenylacetyl, benzoyl, dimethylaminosulfonyl, benzylsulfonyl, 1-piperizinylcarbonyl, 4-methy-1-lpiperazinylcarbonyl or 4-morpholinylcarbonyl; $R^8$ is butyl, 2-phenylethyl, 2-methylsulfonylethyl, 2-tert-butoxycarbonylethyl, 2-tert-butoxycarbonylmethyl, 4-tert-butoxycarbonylaminobutyl, 4-benzoylaminobutyl or benzyloxymethyl; and $R^7$ is 3-pyridylmethyl, 2-thienylmethyl, 2-furylmethyl, 4-imidazolylmethyl, 3-indolylmethyl, a group selected from $(C_{1-5})$alkyl (which group is optionally substituted with a radical selected from mercapto, carboxy, amino, methylthio, methylsulfonyl, carbamoyl, dimethylcarbamoyl, guanidino and hydroxy, or a protected derivative thereof), a group selected from benzyl, 1-naphthylmethyl, 2-naphthylmethyl and 2-phenylethyl (which group is optionally substituted at its aryl ring with one radical selected from hydroxy, amino, chloro, bromo and fluoro, or a protected form thereof) or together with an adjacent $R^3$ or $R^5$ forms a divalent radical selected from $(C_{3-4})$methylene and 1,2-phenylenedimethylene (which radical is optionally substituted with hydroxy, or a protected derivative thereof, or oxo).

19. The compound of claim 18 in which each n is 0; each $R^3$, $R^5$ and $R^6$ are hydrogen; each $R^1$ is hydrogen, tert-butxoycarbonyl, benzyloxycarbonyl, biotinylaminohexanoyl, benzoyl, 1-piperizinylcarbonyl, 4-methyl-1-piperazinylcarbonyl or 4-morpholinylcarbonyl; $R^8$ is butyl, 2-phenylethyl or 2-methylsulfonylethyl; and $R^7$ is $(C_{1-5})$alkyl, 2-methylsulfonylethyl, optionally substituted benzyl, 1-naphthylmethyl, 2-naphthylmethyl, 3-pyridinylmethyl or 2-methylsulfonylethyl.

20. The compound of claim 19 in which each $R^1$ is 1-piperizinylcarbonyl, 4-methyl-1-piperazinylcarbonyl or 4-morpholinylcarbonyl; $R^8$ is 2-phenylethyl; and $R^7$ is optionally substituted benzyl, 1-naphthylmethyl or 2-naphthylmethyl.

21. The compound of claim 20 in which $R^1$ is 4-morpholinylcarbonyl, $R^8$ is 2-phenylethyl, $R^7$ is 2-naphthylmethyl and $R^9$ is ethoxycarbonyl namely ethyl 4S-[N-(4-morpholinylcarbonyl)-β-(2-naphthyl)-L-alanylamino]-6-phenylhexanoate.

22. The compound of claim 20 in which $R^1$ is 4-morpholinylcarbonyl, $R^8$ is 2-phenylethyl, $R^7$ is benzyl and $R^9$ is ethoxycarbonyl namely ethyl 4S-[N-(4-morpholinylcarbonyl)-L-phenylalanylamino]-6-phenylhexanoate.

23. The compound of claim 20 in which $R^1$ is 4-morpholinylcarbonyl, $R^1$ is 2-phenylethyl, $R^7$ is benzyl and $R^9$ is phenylcarbamoyl namely N²-(4-morpholinylcarbonyl)-N¹-[3-phenyl-1S-(2-phenylcarbamoylethyl)propyl]-L-phenylalaninamide.

24. The compound of claim 20 in which $R^1$ is 4-morpholinylcarbonyl, $R^1$ is 2-phenylethyl, $R^7$ is benzyl and $R^1$ is benzylcarbamoyl namely N²-4-(morpholinylcarbonyl)-N¹-[3-phenyl-1S-(2-benzylcarbamoylethyl)propyl]-L-phenylalaninamide.

25. A compound of Formula III:

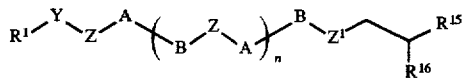

in which:
n is 0 to 13;
A-B represents a linkage selected from —C(O)NR³—, —CH₂NR³—, —C(O)CH₂— and —NR³C(O)—, wherein R³ is hydrogen or as defined below;
Y is —CH(R⁵)— or —NR⁵—, wherein R⁵ is hydrogen or as defined below;

Z is —(CH₂)₂—, —C(R⁶)(R⁷)— or —N(R⁷)—, wherein $R^6$ is hydrogen or methyl and $R^7$ is as defined below;
$Z^1$ is —(CH₂)₂—, —C(R⁶)(R⁸)— or —N(R⁶)—, wherein $R^6$ is hydrogen or methyl and $R^8$ is as defined below;

$R^1$ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

$R^7$ and $R^8$ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof, cycloalkyl, cycloalkylalkyl, heteroaryl, heteroarylalkyl, a group selected from aryl and arylalkyl (which group is optionally substituted at its aryl ring with one to three radicals selected from hydroxy, amino, guanidino, halo, optionally halo-substituted alkyl, alkyloxy and aryl, or a protected derivative thereof or together with an adjacent $R^3$ or $R^5$ forms a divalent radical selected from a divalent radical selected from $(C_{3-4})$methylene and 1,2-phenylenedimethylene (which radical is optionally substituted with hydroxy, or a protected derivative thereof, or oxo); $R^{15}$ is hydrogen, methyl, fluoro or a group selected from Formulae (a) and (b):

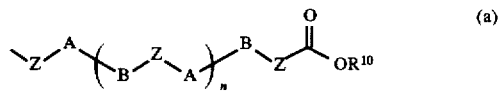

wherein each n, A, B, Y, Z and $R^1$ are as defined above and $R^{10}$ is hydrogen, alkyl (optionally substituted with one or more radicals selected from amino, halo, hydroxy, alkyloxy, nitro, alkylsulfonyl and arylsulfonyl, or a protected derivative thereof, cycloalkyl, cycloalkylalkyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof; and $R^{16}$ is a group selected from phenyl or $(C_{5-6})$heteroaryl (which group is optionally substituted with at least one radical selected from alkylcarbamoyl, dialkylcarbamoyl, alkyloxycarbonyl, alkylsulfinamoyl, dialkylsulfinamoyl, alkylsulfonyl, carboxy, nitro, sulfinamoyl, sulfo, carbamoyl, phosphono, alkyloxyphosphinyl, dialkyloxyphosphinyl, alkanoyl, cyano, alkylsulfinyl, sulfamoyl, alkylsulfamoyl, dialkylsulfamoyl, alkyloxysulfonyl, alkylsulfonimidoyl, aryl, heteroaryl, hydroxy, alkyloxy, optionally halo-substituted alkyl, arylalkyl, halo, —⁺N(R¹⁷)₃, wherein each $R^{17}$ is independently alkyl, aryl or arylalkyl, or —N(R¹⁸)₂, wherein each R¹I is independently hydrogen, alkyl, aryl or arylalkyl); and the pharmaceutically acceptable salts; individual isomers and mixtures of isomers thereof.

26. The compound of claim 25 in which each n is 0 to 5; each A-B represents a linkage selected from —C(O)NR³—; each Y is —NR⁵—; each Z is —(CH₂)₂— or —C(R⁶)(R⁷)—; Z¹ is —CH(R⁸)—; each R¹ is hydrogen, alkyloxycarbonylalkanoyl of overall 3 to 10 carbon atoms, (C₁₋₉) alkoxycarbonyl, (C₂₋₁₀)alkanoyl (optionally substituted with a radical selected from carboxy, (C₁₋₉)alkyloxycarbonyl and hetero(C₄₋₈)cycloalkyl(C₂₋₁₀)alkanoylamino), (C₄₋₉) cycloalkylcarbonyl, hetero(C₄₋₈)cycloalkylcarbonyl (optionally substituted with a radical selected from hydroxy, (C₁₋₅)alkyl, (C₁₋₅)alkanoyl, (C₁₋₅)alkyloxycarbonyl, (C₆₋₁₀) aryl(C₁₋₅)alkyloxycarbonyl and hetero(C₄₋₈) cycloalkylcarbonyl), (C₆₋₁₀)aryl(C₁₋₅)alkyloxycarbonyl, carbamoyl, (C₁₋₅)alkylcarbamoyl, di(C₁₋₅)alkylcarbamoyl, (C₆₋₁₀)arylcarbamoyl, (C₆₋₁₀)aryl(C₁₋₅)alkylcarbamoyl, (C₆₋₁₀)aryl(C₁₋₅)alkanoyl, (C₇₋₁₁)aroyl, (C₁₋₅)alkylsulfonyl, di(C₁₋₅)alkylaminosulfonyl, (C₆₋₁₀)arylsulfonyl or hetero (C₅₋₈)arylsulfonyl; R⁸ and R⁷ are independently (C₃₋₇) cycloalkyl, (C₃₋₇)cycloalkyl(C₁₋₅)alkyl, pyridyl, thienyl, furyl, imidazolyl, indolyl, pyridyl(C₁₋₆)alkyl, thienyl(C₁₋₆) alkyl, furyl(C₁₋₆)alkyl, imidazolyl(C₁₋₆)alkyl, indolyl(C₁₋₆) alkyl, a group selected from (C₁₋₅)alkyl, (C₂₋₆)alkyloxy and (C₁₋₅)alkanoyloxy (which group is optionally substituted with a radical selected from mercapto, carboxy, amino, methylthio, methylsulfonyl, carbamoyl, dimethylcarbamoyl, guanidino and hydroxy, or a protected derivative thereof, a group selected from phenyl, naphthyl, phenyl(C₁₋₆)alkyl, naphthyl(C₁₋₆)alkyl, (which group is optionally substituted at its aryl ring with one to three radicals selected from amino, hydroxy, chloro, bromo, fluoro, methyl, trifluoromethyl, methoxy and phenyl, or a protected derivative thereof) or together with an adjacent R³ or R⁵ forms a divalent radical selected from (C₃₋₄)methylene and 1,2-phenylenedimethylene (which radical is optionally substituted with hydroxy, or a protected derivative thereof, or oxo); R¹⁰ is (C₁₋₅)alkyl (optionally substituted with one or two radicals selected from amino, chloro, bromo, fluoro, hydroxy and methoxy or a protected derivative thereof, (C₃₋₇)cycloalkyl, (C₃₋₇)cycloalkyl(C₁₋₅)alkyl, or a group selected from phenyl or phenyl(C₁₋₆)alkyl (which group is optionally substituted at its phenyl ring with one to two radicals selected from amino, chloro, bromo, fluoro, hydroxy, methoxy and optionally halo-substituted methyl, or a protected derivative thereof; and R¹⁶ is a group selected from 2-furyl, 2-thienyl, 2-pyrrolyl, 2-phosholyl, 2-arsolyl, 3-pyridyl or 3-phosphorinyl (which group is optionally substituted with at least one radical selected from (C₁₋₅) alkylcarbamoyl, di(C₁₋₅)alkylcarbamoyl, (C₁₋₅) alkyloxycarbonyl, (C₁₋₅)alkylsulfinamoyl, di(C₁₋₅) alkylsulfinamoyl, (C₁₋₅)alkylsulfonyl, carboxy, nitro, sulfinamoyl, sulfo, carbamoyl, phosphono, (C₁₋₅) alkyloxyphosphinyl, di(C₁₋₅)alkyloxyphosphinyl, (C₁₋₅) alkanoyl, cyano, (C₁₋₅)alkylsulfinyl, sulfamoyl, (C₁₋₅) alkylsulfamoyl, di(C₁₋₅)alkylsulfamoyl, (C₁₋₅) alkyloxysulfonyl, (C₁₋₅)alkylsulfonimidoyl, phenyl, naphthyl, pyridyl, thienyl, furyl, imidazolyl, indolyl, hydroxy, (C₁₋₅)alkyloxy, optionally halo-substituted (C₁₋₅) alkyl, benzyl, halo, —⁺N(R¹⁷)₃, wherein each R¹⁷ is independently (C₁₋₅)alkyl, phenyl or benzyl, or —N(R¹⁸)₂, wherein each R¹⁸ is independently hydrogen, (C₁₋₅)alkyl, phenyl or benzyl).

27. The compound of claim 26 in which each n is 0 to 2; Z is —(CH₂)₂— or —C(R⁶)(R⁷)— (with the proviso that when n is 0, Z is not —(CH₂)₂—); each R¹ is hydrogen, (C₄₋₈)alkoxycarbonyl, (C₂₋₆)alkanoyl (optionally substituted with a radical selected from carboxy, (C₁₋₅) alkyloxycarbonyl and hetero(C₄₋₈)cycloalkyl(C₄₋₆) alkanoylamino), —C(O)NR²¹R²² wherein R²¹ and R²² together aza(C₂₋₆)methylene, oxa(C₂₋₆)methylene or (C₃₋₇) methylene, (C₄₋₈)cycloalkylcarbonyl, benzyloxycarbonyl, acetyl, benzoyl or dimethylaminosulfonyl; R⁸ and R⁷ are independently (C₅₋₆)cycloalkyl, (C₅₋₆)cycloalkylmethyl, 3-pyridyl, 2-thienyl, 2-furyl, 4-imidazolyl, 3-indolyl, 3-pyridylmethyl, 2-thienylmethyl, 2-furylmethyl, 4-imidazolylmethyl, 3-indolylmethyl, methoxy, acetoxy, (C₁₋₅)alkyl (optionally substituted with a radical selected from mercapto, carboxy, amino, methylthio, methylsulfonyl, carbamoyl, dimethylcarbamoyl, guanidino and hydroxy, or a protected derivative thereof) a group selected from phenyl, 1-naphthyl, 2-naphthyl, benzyl, 1-naphthylmethyl, 2-naphthylmethyl and 2-phenylethyl (which group is optionally substituted at its aryl ring with one radical selected from hydroxy, amino, chloro, bromo and fluoro, or a protected form thereof) or together with an adjacent R³ or R⁵ forms a divalent radical selected from (C₃₋₄)methylene and 1,2-phenylenedimethylene (which radical is optionally substituted with hydroxy, or a protected derivative thereof, or oxo); each R¹⁰ is ethyl, (C₅₋₆)cycloalkyl, (C₅₋₆) cycloalkylmethyl or a group selected from phenyl and benzyl (which group is optionally substituted at its phenyl ring with one radical selected from amino hydroxy, chloro, bromo or fluoro, or a protected derivative thereof); and R¹⁶ is a group selected from 2-furyl, 2-thienyl, 2-pyrrolyl, 2-phosholyl, 2-arsolyl, 2-pyridyl or 3-phosphorinyl (which group is optionally substituted with at least one radical selected from methylcarbamoyl, dimethylcarbamoyl, methyloxycarbonyl, methylsulfinamoyl, dimethylsulfinamoyl, methylsulfonyl, carboxy, nitro, sulfinamoyl, sulfo, carbamoyl, phosphono, methyloxyphosphinyl, dimethyloxyphosphinyl, formyl, cyano, methylsulfinyl, sulfamoyl, methylsulfamoyl, dimethylsulfamoyl, methoxysulfonyl, methylsulfonimidoyl, phenyl, naphthyl, pyridyl, thienyl, furyl, imidazolyl, indolyl, hydroxy, methoxy, methyl, trifluromethyl, benzyl, halo, —⁺N(R¹⁷)₃, wherein each R¹⁷ is independently methyl, phenyl or benzyl, or —N(R¹⁸)₂, wherein each R¹⁸ is independently hydrogen, methyl, phenyl or benzyl).

28. The compound of claim 27 in which each n is 0 to 1; Z is —C(R⁶)(R⁷)—; each R¹ is hydrogen, tert-butoxycarbonyl, benzyloxycarbonyl, acetyl, 3-carboxypropionyl, 3-methoxycarbonylpropionyl, biotinylaminohexanoyl, phenylacetyl, benzoyl, dimethylaminosulfonyl, benzylsulfonyl, 1-piperizinylcarbonyl, 4-methyl-1-piperazinylcarbonyl or 4-morpholinylcarbonyl; R⁸ is butyl, 2-phenylethyl, 2-methylsulfonylethyl, 2-tert-butoxycarbonylethyl, 2-tert-butoxycarbonylmethyl, 4-tert-butoxycarbonylaminobutyl, 4-benzoylaminobutyl or benzyloxymethyl; and R⁷ is 3-pyridylmethyl, 2-thienylmethyl, 2-furylmethyl, 4-imidazolylmethyl, 3-indolylmethyl, (C₁₋₅)alkyl (optionally substituted with a radical selected from mercapto, carboxy, amino, methylthio, methylsulfonyl, carbamoyl, dimethylcarbamoyl, guanidino and hydroxy, or a protected derivative thereof), a group selected from benzyl, 1-naphthylmethyl, 2-naphthylmethyl and 2-phenylethyl (which group is optionally substituted at its aryl ring with one radical selected from hydroxy, amino, chloro, bromo and fluoro, or a protected form thereof) or together with an adjacent R³ or R⁵ forms a divalent radical selected from (C₃₋₄)methylene and 1,2-phenylenedimethylene (which radical is optionally substituted with hydroxy, or a protected derivative thereof, or oxo).

29. The compound of claim 28 in which each n is 0; each R³, R⁵ and R⁶ are hydrogen; each R¹ is hydrogen, tert-butxoycarbonyl, benzyloxycarbonyl, biotinylaminohexanoyl, benzoyl, 1-piperizinylcarbonyl, 4-methyl-1-piperazinylcarbonyl or 4-morpholinylcarbonyl; R¹ is butyl, 2-phenylethyl or 2-methylsulfonylethyl; and R⁷ is (C₁₋₅)alkyl, 2-methylsulfonylethyl, optionally substituted benzyl, 1-naphthylmethyl, 2-naphthylmethyl, 3-pyridinylmethyl or 2-methylsulfonylethyl.

30. The compound of claim 29 in which each R¹ is 1-piperizinylcarbonyl, 4-methyl-1-piperazinylcarbonyl or 4-morpholinylcarbonyl; R¹ is 2-phenylethyl; and R⁷ is optionally substituted benzyl, 1-naphthylmethyl or 2-naphthylmethyl.

31. The compound of claim 30 in which R¹ is 4-morpholinylcarbonyl, R¹ is 2-phenylethyl, R⁷ is benzyl, R¹⁵ is hydrogen and R¹⁶ is 4-methoxyphenyl, namely N²-4-morpholinylcarbonyl-N¹-{3-phenyl-1S-|2-(4-methoxyphenyl)ethyl|propyl}-L-phenylalaninamide.

32. The compound of claim 30 in which R¹ is 4-morpholinylcarbonyl, R¹ is 2-phenylethyl, R⁷ is benzyl, R¹⁵ is hydrogen and R¹⁶ is 4-aminophenyl, namely N²-(4-morpholinylcarbonyl)-N¹-{3-phenyl-1S-|2-(4-aminophenyl)ethyl|propyl}-L-phenylalaninamide.

33. A method for inhibiting a cysteine protease comprising reversibly binding a cysteine protease inhibitor to a cysteine protease, wherein said inhibitior comprises the cysteine protease inhibitor of claim 1.

34. A method for inhibiting a cysteine protease comprising reversibly binding a cysteine protease inhibitor to a cysteine protease, wherein said inhibitior comprises the cysteine protease inhibitor of claim 2.

35. A method for inhibiting a cysteine protease comprising reversibly binding a cysteine protease inhibitor to a cysteine protease, wherein said inhibitior comprises the cysteine protease inhibitor of claim 3.

36. A method for inhibiting a cysteine protease comprising reversibly binding a cysteine protease inhibitor to a cysteine protease, wherein said inhibitior comprises the cysteine protease inhibitor of claim 14.

37. A method for inhibiting a cysteine protease comprising reversibly binding a cysteine protease inhibitor to a cysteine protease, wherein said inhibitior comprises the cysteine protease inhibitor of claim 24.

38. A method for treating a condition capable of amelioration by inhibition of a cysteine protease in an animal in need thereof, which method comprises administering to such animal a therapeutically effective amount of the cysteine protease inhibitor of claim 1.

39. A method for treating a condition capable of amelioration by inhibition of a cysteine protease in an animal in need thereof, which method comprises administering to such animal a therapeutically effective amount of the cysteine protease inhibitor of claim 2.

40. A method for treating a condition capable of amelioration by inhibition of a cysteine protease in an animal in need thereof, which method comprises administering to such animal a therapeutically effective amount of the cysteine protease inhibitor of claim 3.

41. A method for treating a condition capable of amelioration by inhibition of a cysteine protease in an animal in need thereof, which method comprises administering to such animal a therapeutically effective amount of the cysteine protease inhibitor of claim 14.

42. A method for treating a condition capable of amelioration by inhibition of a cysteine protease in an animal in need thereof, which method comprises administering to such animal a therapeutically effective amount of the cysteine protease inhibitor of claim 24.

43. A pharmaceutical composition comprising a therapeutically effective amount of the cysteine protease inhibitor of claim 1, or of an individual isomer, a mixture of isomers, or the pharmaceutically acceptable salt or salts thereof, in combination with one or more pharmaceutically acceptable excipients.

44. A pharmaceutical composition comprising a therapeutically effective amount of the cysteine protease inhibitor of claim 2, or of an individual isomer, a mixture of isomers, or the pharmaceutically acceptable salt or salts thereof, in combination with one or more pharmaceutically acceptable excipients.

45. A pharmaceutical composition comprising a therapeutically effective amount of the cysteine protease inhibitor of claim 3, or of an individual isomer, a mixture of isomers, or the pharmaceutically acceptable salt or salts thereof, in combination with one or more pharmaceutically acceptable excipients.

46. A pharmaceutical composition comprising a therapeutically effective amount of the cysteine protease inhibitor of claim 14, or of an individual isomer, a mixture of isomers, or the pharmaceutically acceptable salt or salts thereof, in combination with one or more pharmaceutically acceptable excipients.

47. A pharmaceutical composition comprising a therapeutically effective amount of the cysteine protease inhibitor of claim 24, or of an individual isomer, a mixture of isomers, or the pharmaceutically acceptable salt or salts thereof, in combination with one or more pharmaceutically acceptable excipients.

48. A process for the preparation of a compound of Formula IV:

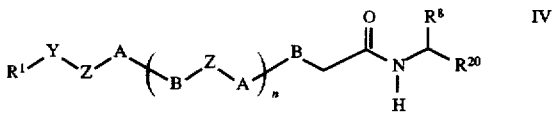

in which:

n is 0 to 12;

A-B represents a linkage selected from —C(O)NR³—, —CH₂NR³—, —C(O)CH₂— and —NR³C(O)—, wherein R³ is hydrogen or as defined below;

Y is —CH(R⁵)— or —N(R⁵)—, wherein R⁵ is hydrogen or as defined below;

Z is —(CH₂)₂—, —C(R⁶)(R⁷)— or —N(R⁷)-, wherein R¹ is hydrogen or methyl and R⁷ is as defined below;

Z¹ is —(CH₂)₂—, —C(R⁶)(R⁸)— or —N(R⁸)-, wherein R⁶ is hydrogen or methyl and R⁸ is as defined below;

R⁶ is hydrogen or methyl and R⁷ is as defined below;

R¹ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

R⁷ and R⁸ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof, cycloalkyl, cycloalkylalkyl, heteroaryl, heteroarylalkyl, a group selected from aryl and arylalkyl (which group is optionally substituted at its aryl ring with one to three radicals selected from hydroxy, amino, guanidino, halo, optionally halo-substituted alkyl, alkyloxy and aryl, or a protected derivative thereof) or together with an adjacent $R^3$ or $R^5$ forms a divalent radical selected from a divalent radical selected from $(C_{3-4})$methylene and 1,2-phenylenedimethylene (which radical is optionally substituted with hydroxy, or a protected derivative thereof, or oxo); and $R^{20}$ is cyano, —$S(O)_2R^2$, —$CH_2S(O)_2R^2$, —$CH_2CH(R^4)$ $S(O)_2R^2$, —$(CH_2)_2C(O)OR^{10}$, —$(CH_2)_2P(O)(OR^{10})_2$, —$(CH_2)_2S(O)(NR^{10})R^{10}$, —$(CH_2)_2C(O)R^{11}$, —$(CH_2)_2S(O)R^{11}$, —$(CH_2)_2C(O)NR^{12}R^{13}$, —$(CH_2)_2S(O)_2NR^{12}R^{13}$, —$(CH_2)_2C(O)NHR^{14}$, —$(CH_2)_2S(O)_2NHR^{14}$ or —$CH_2CHR^{15}R^{16}$, wherein $R^2$ is hydrogen, alkyl (optionally substituted with one or more radicals selected from amino, halo, hydroxy, alkyloxy, nitro, alkylsulfonyl and arylsulfonyl, or a protected derivative thereof, cycloalkyl, cycloalkylalkyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof, $R^4$ is hydrogen, alkyl or arylalkyl, each $R^{10}$ is independently hydrogen, alkyl (optionally substituted with one or more radicals selected from amino, halo, hydroxy, alkyloxy, nitro, alkylsulfonyl and arylsulfonyl, or a protected derivative thereof, cycloalkyl, cycloalkylalkyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof, $R^{11}$ is hydrogen, alkyl, perfluoroalkyl, cycloalkyl, cycloalkylalkyl, perfluoroaryl, perfluoroarylakyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof), $R^{12}$ and $R^{13}$ are independently hydrogen, alkyl, cycloalkyl, cycloalkylalkyl, aryl or aralkyl, $R^{14}$ is —$C(O)OR^{10}$, in which $R^{10}$ is as defined above, or a group selected from Formula (a) and (b):

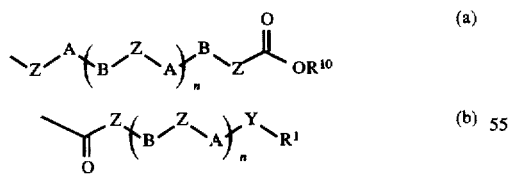

wherein each n, A, B, Y, Z, $R^1$ and $R^{10}$ are as defined above, $R^{15}$ is hydrogen, methyl, fluoro or a group selected from Formulae (a) and (b) as defined above, and $R^{16}$ is a group selected from phenyl or $(C_{5-6})$heteroaryl (which group is optionally substituted with at least one radical selected from alkylcarbamoyl, dialkylcarbamoyl, alkyloxycarbonyl, alkylsulfinamoyl, dialkylsulfinamoyl, alkylsulfonyl, carboxy, nitro, sulfinamoyl, sulfo, carbamoyl, phosphono, alkyloxyphosphinyl, dialkyloxyphosphinyl, alkanoyl, cyano, alkylsulfinyl, sulfamoyl, alkylsulfamoyl, dialkylsulfamoyl, alkyloxysulfonyl, alkylsulfonimidoyl, aryl, heteroaryl, hydroxy, alkyloxy, optionally halo-substituted alkyl, arylalkyl, halo, —$^+N(R^{17})_3$, wherein each $R^{17}$ is independently alkyl, aryl or arylalkyl, or —$N(R^{18})_2$, wherein each $R^{18}$ is independently hydrogen, alkyl, aryl or arylalkyl); and the pharmaceutically acceptable salts, individual isomers and mixtures of isomers thereof; which process comprises:

(A) reacting an amine of Formula V:

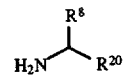

with a compound of Formula VI:

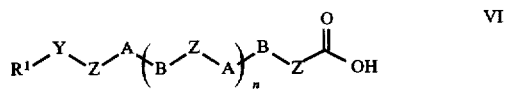

in which each n, A, B, X, Y, Z, $R^1$, $R^8$ and $R^{20}$ are as defined above; and (B) optionally further converting a non-salt form of a compound of Formula IV into a pharmaceutically acceptable salt;

(C) optionally further converting a salt form of a compund of Formula IV into non-salt form; and (D) optionally further separating a compound of Formula IV into individual stereoisomers.

49. A process for the preparation of a compound of Formula IV:

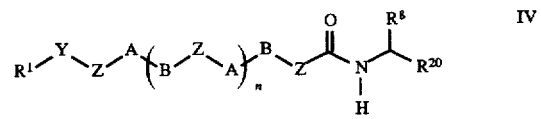

in which:

n is 0 to 12;

A-B represents a linkage selected from —$C(O)NR^3$—, —$CH_2NR$, —$C(O)CH_2$— and —$NR^3C(O)$—, wherein $R^3$ is hydrogen or as defined below;

Y is —$CH(R^5)$— or —$N(R^5)$—, wherein $R^5$ is hydrogen or as defined below;

Z is —$(CH_2)_2$—, —$C(R^6)(R^7)$— or —$N(R^7)$—, wherein $R^6$ is hydrogen or methyl and $R^7$ is as defined below;

$Z^1$ is —$(CH_2)_2$—, —$C(R^6)(R^8)$— or —$N(R^8)$—, wherein $R^1$ is hydrogen or methyl and $R^8$ is as defined below;

$R^6$ is hydrogen or methyl and $R^7$ is as defined below;

$R^1$ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

$R^7$ and $R^8$ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof), cycloalkyl, cycloalkylalkyl, heteroaryl, heteroarylalkyl, a group selected from aryl and arylalkyl (which group is optionally substituted at its aryl ring with one to three radicals selected from hydroxy, amino, halo, optionally halo-substituted alkyl, alkyloxy and aryl, or a protected derivative thereof) or together with an adjacent $R^3$ or $R^5$ forms a divalent radical selected from a divalent radical selected from $(C_{3-4})$methylene and 1,2-phenylenedimethylene (which radical is optionally substituted with hydroxy, or a protected derivative thereof, or oxo); and $R^{20}$ is $-S(O)_2R^2$, wherein $R^2$ is hydrogen, alkyl (optionally substituted with one or more radicals selected from amino, halo, hydroxy, alkyloxy, nitro, alkylsulfonyl and arylsulfonyl, or a protected derivative thereof), cycloalkyl, cycloalkylalkyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof), and the pharmaceutically acceptable salts, individual isomers and mixtures of isomers thereof; which process comprises:

reacting a compound of Formula VII:

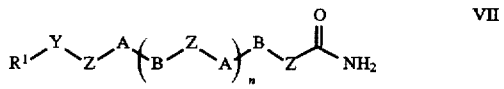

with an aldehyde of the formula $R^8CHO$ and a sodium sulfinate of the formula $R^2S(O)ONa$, in which each n, A, B, X, Y, Z, $R^1$ and $R^8$ are as defined above;

(B) optionally further converting a non-salt form of a compound of Formula IV into a pharmaceutically acceptable salt;

(C) optionally further converting a salt form of a compund of Formula IV into non-salt form; and (D) optionally further separating a compound of Formula IV into individual stereoisomers.

50. A process for the preparation of a compound of Formula IV:

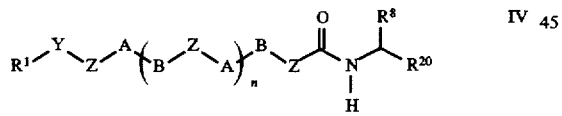

in which:

n is 0 to 12;

A-B represents a linkage selected from $-C(O)NR^3-$, $-CH_2NR^3-$, $-C(O)CH_2-$ and $-NR^3C(O)-$, wherein $R^3$ is hydrogen or as defined below;

Y is $-CH(R^5)-$ or $-N(R^5)-$, wherein $R^5$ is hydrogen or as defined below;

Z is $-(CH_2)_2-$, $-C(R^6)(R^7)-$ or $-N(R^7)-$, wherein $R^6$ is hydrogen or methyl and $R^7$ is as defined below;

$Z^1$ is $-(CH_2)_2-$, $-C(R^6)(R^8)-$ or $-N(R^8)-$, wherein $R^6$ is hydrogen or methyl and $R^8$ is as defined below;

$R^6$ is hydrogen or methyl and $R^7$ is as defined below;

$R^1$ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

$R^7$ and $R^8$ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof), cycloalkyl, cycloalkylalkyl, heteroaryl, heteroarylalkyl, a group selected from aryl and arylalkyl (which group is optionally substituted at its aryl ring with one to three radicals selected from hydroxy, amino, halo, optionally halo-substituted alkyl, alkyloxy and aryl, or a protected derivative thereof) or together with an adjacent $R^3$ or $R^5$ forms a divalent radical selected from a divalent radical selected from $(C_{3-4})$methylene and 1,2-phenylenedimethylene (which radical is optionally substituted with hydroxy, or a protected derivative thereof, or oxo); and $R^{20}$ is $-S(O)_2R^2$, wherein $R^2$ is hydrogen, alkyl (optionally substituted with one or more radicals selected from amino, halo, hydroxy, alkyloxy, nitro, alkylsulfonyl and arylsulfonyl, or a protected derivative thereof), cycloalkyl, cycloalkylalkyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof); and the pharmaceutically acceptable salts, individual isomers and mixtures of isomers thereof; which process comprises:

(A)

(1) reacting a compound of the formula $NH_2P$, wherein P is a protective group, with an aldehyde of the formula $R^8CHO$ and a sodium sulfinate of the formula $R^2S(O)ONa$ and then deprotecting to give a compound of Formula VIII:

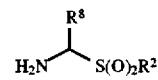

in which $R^2$ and $R^8$ are as defined above; and (2) reacting the compound of Formula VIII with a compound of Formula VI:

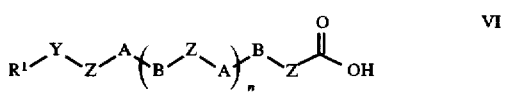

in which each n, A, B, X, Y, Z, and $R^1$ are as defined above;

(B) optionally further converting a non-salt form of a compound of Formula IV into a pharmaceutically acceptable salt;

(C) optionally further converting a salt form of a compund of Formula IV into non-salt form; and (D) optionally further separating a compound of Formula IV into individual stereoisomers.

51. A process for the preparation of a compound of Formula IV:

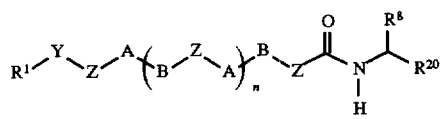

in which:

n is 0 to 12;

A-B represents a linkage selected from —C(O)NR³—, —CH₂NR³—, —C(O)CH₂— and —NR³C(O)—, wherein R³ is hydrogen or as defined below;

Y is —CH(R⁵)— or —N(R⁵)—, wherein R⁵ is hydrogen or as defined below;

Z is —(CH₂)₂—, —C(R⁶)(R⁷)— or —N(R⁷)—, wherein R⁶ is hydrogen or methyl and R⁷ is as defined below;

Z¹ is —(CH₂)₂—, —C(R⁶)(R⁸)— or —N(R⁸)—, wherein R⁶ is hydrogen or methyl and R⁸ is as defined below;

R⁶ is hydrogen or methyl and R⁷ is as defined below;

R¹ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

R⁷ and R⁸ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof), cycloalkyl, cycloalkylalkyl, heteroaryl, heteroarylalkyl, a group selected from aryl and arylalkyl (which group is optionally substituted at its aryl ring with one to three radicals selected from hydroxy, amino, halo, optionally halo-substituted alkyl, alkyloxy and aryl, or a protected derivative thereof or together with an adjacent R³ or R⁵ forms a divalent radical selected from a divalent radical selected from (C₃₋₄)methylene and 1,2-phenylenedimethylene (which radical is optionally substituted with hydroxy, or a protected derivative thereof, or oxo); and R²⁰ is —CH₂S(O)₂R², wherein R² is hydrogen, alkyl (optionally substituted with one or more radicals selected from amino, halo, hydroxy, alkyloxy, nitro, alkylsulfonyl and arylsulfonyl, or a protected derivative thereof), cycloalkyl, cycloalkylalkyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof; and the pharmaceutically acceptable salts, individual isomers and mixtures of isomers thereof; which process comprises:

(A) (1) reacting a compound of Formula IX:

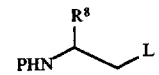

with a thiolate anion of the formula R²S⁻, in which L is a leaving group and R² and R⁸ are as defined above, to give a compound of Formula X:

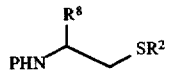

(2) oxidizing the compound of Formula X to give a compound of Formula XI:

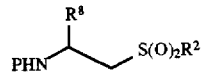

and (3) reacting the compound of Formula XI with a compound of Formula VI:

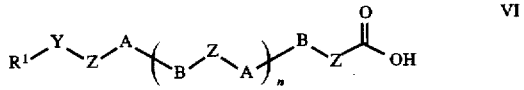

in which each n, A, B, X, Y, Z and R¹ are as defined above;

(B) optionally further converting a non-salt form of a compound of Formula IV into a pharmaceutically acceptable salt;

(C) optionally further converting a salt form of a compund of Formula IV into non-salt form; and (D) optionally further separating a compound of Formula IV into individual stereoisomers.

52. A process for the preparation of a compound of Formula IV:

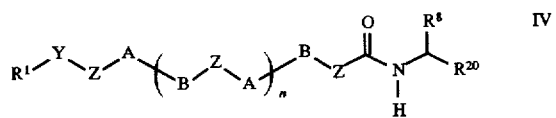

in which:

n is 0 to 12;

A-B represents a linkage selected from —C(O)NR³—, —CH₂NR³—, —C(O)CH₂— and —NR³C(O)—, wherein R³ is hydrogen or as defined below;

Y is —CH(R⁵)— or —N(R⁵)—, wherein R⁵ is hydrogen or as defined below;

Z is —(CH₂)₂—, —C(R⁶)(R⁷)— or —N(R⁷)—, wherein R⁶ is hydrogen or methyl and R⁷ is as defined below;

Z¹ is —(CH₂)₂—, —C(R⁶)(R⁷)— or —N(R⁸)—, wherein R⁸ is hydrogen or methyl and R⁸ is as defined below;

R⁶ is hydrogen or methyl and R⁷ is as defined below;

R¹ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

R⁷ and R⁸ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof, cycloalkyl, cycloalkylalkyl, heteroaryl, heteroarylalkyl, a group selected from aryl and arylalkyl (which group is optionally substituted at its aryl ring with one to three radicals selected from hydroxy, amino, halo, optionally halo-substituted alkyl, alkyloxy and aryl, or a protected derivative thereof) or together with an adjacent R³ or R⁵ forms a divalent radical selected from a divalent radical selected from (C₃₋₄)methylene and 1,2-phenylenedimethylene (which radical is optionally substituted with hydroxy, or a protected derivative thereof, or oxo); and R²⁰ is cyano, —(CH₂)₂S(O)₂R², —(CH₂)₂C(O)OR¹⁰, —(CH₂)₂P(O)(OR¹⁰)₂, —(CH₂)₂S(O)NR¹⁰R¹⁰, —(CH₂)₂C(O)R¹¹, —(CH₂)₂S(O)R¹¹, —(CH₂)₂C(O)NR¹²R¹³, —(CH₂)₂S(O)₂NR¹²R¹³, —(CH₂)₂C(O)NHR¹⁴ or —(CH₂)₂S(O)₂NHR¹⁴, wherein R² is hydrogen, alkyl (optionally substituted with one or more radicals selected from amino, halo, hydroxy, alkyloxy, nitro, alkylsulfonyl and arylsulfonyl, or a protected derivative thereof, cycloalkyl, cycloalkylalkyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof, each R¹⁰ is independently hydrogen, alkyl (optionally substituted with one or more radicals selected from amino, halo, hydroxy, alkyloxy, nitro, alkylsulfonyl and arylsulfonyl, or a protected derivative thereof), cycloalkyl, cycloalkylalkyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof, R¹¹ is hydrogen, alkyl, perfluoroalkyl, cycloalkyl, cycloalkylalkyl, perfluoroaryl, perfluoroarylakyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof), R¹² and R¹³ are independently hydrogen, alkyl, cycloalkyl, cycloalkylalkyl, aryl or aralkyl and R¹⁴ is —C(O)OR¹⁰, in which R¹⁰ is as defined above, or a group selected from Formula (a) and (b):

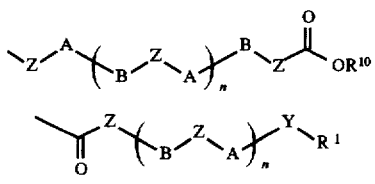

wherein each n, A, B, Y, Z, R¹ and R¹⁰ are as defined above; and the pharmaceutically acceptable salts, individual isomers and mixtures of isomers thereof; which process comprises:

(A)

(1) reacting an aldehyde of Formula XII:

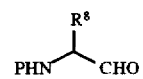

with a compound selected from Formulae XIII and XIV:

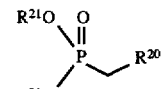

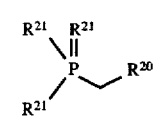

in which each R⁸ and R²⁰ are as defined above, and then deprotecting to give a compound of Formula XV:

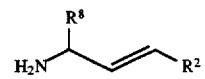

(2) reacting the compound of Formula XV with a compound of Formula VI:

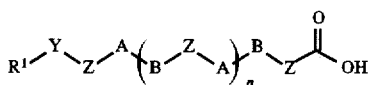

in which each n, A, B, X, Y, Z and R¹ are as defined above, and (3) reducing;

(B) optionally further converting a non-salt form of a compound of Formula IV into a pharmaceutically acceptable salt;

(C) optionally further converting a salt form of a compund of Formula IV into non-salt form; and (D) optionally further separating a compound of Formula IV into individual stereoisomers.

53. A process for the preparation of a compound of Formula IV:

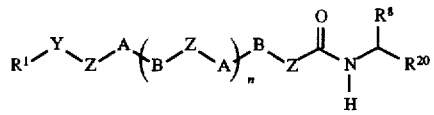

in which:

n is 0 to 12;

A-B represents a linkage selected from —C(O)NR³—, —CH₂NR³—, —C(O)CH₂— and —NR³C(O)—, wherein R³ is hydrogen or as defined below;

Y is —CH(R⁵)— or —N(R⁵)—, wherein R⁵ is hydrogen or as defined below;

Z is —(CH₂)₂—, —C(R⁶)(R⁷)— or —N(R⁷)—, wherein R⁶ is hydrogen or methyl and R⁷ is as defined below;

Z¹ is —(CH₂)₂—, —C(R⁶)(R⁸)— or —N(R⁸)—, wherein R⁶ is hydrogen or methyl and R⁸ is as defined below;

R⁶ is hydrogen or methyl and R⁷ is as defined below;

R¹ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

$R^7$ and $R^8$ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof, cycloalkyl, cycloalkylalkyl, heteroaryl, heteroarylalkyl, a group selected from aryl and arylalkyl (which group is optionally substituted at its aryl ring with one to three radicals selected from hydroxy, amino, halo, optionally halo-substituted alkyl, alkyloxy and aryl, or a protected derivative thereof) or together with an adjacent $R^3$ or $R^1$ forms a divalent radical selected from a divalent radical selected from $(C_{3-4})$methylene and 1,2-phenylenedimethylene (which radical is optionally substituted with hydroxy, or a protected derivative thereof, or oxo); and $R^{20}$ is —$CH_2CHR^{15}R^{16}$, wherein $R^{15}$ is hydrogen, methyl, fluoro or a group selected from Formulae (a) and (b):

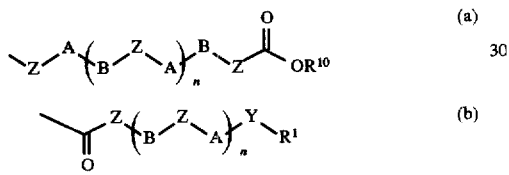

wherein each n, A, B, Y, Z, $R^1$ and $R^{10}$ are as defined above, and $R^{16}$ is a group selected from phenyl or $(C_{5-6})$heteroaryl (which group is optionally substituted with at least one radical selected from alkylcarbamoyl, dialkylcarbamoyl, alkyloxycarbonyl, alkylsulfinamoyl, dialkylsulfinamoyl, alkylsulfonyl, carboxy, nitro, sulfinamoyl, sulfo, carbamoyl, phosphono, alkyloxyphosphinyl, dialkyloxyphosphinyl, alkanoyl, cyano, alkylsulfinyl, sulfamoyl, alkylsulfamoyl, dialkylsulfamoyl, alkyloxysulfonyl, alkylsulfonimidoyl, aryl, heteroaryl, hydroxy, alkyloxy, optionally halo-substituted alkyl, arylalkyl, halo, —$^+N(R^{17})_3$, wherein each $R^{17}$ is independently alkyl, aryl or arylalkyl, or —$N(R^{18})_2$, wherein each $R^{18}$ is independently hydrogen, alkyl, aryl or arylalkyl); and the pharmaceutically acceptable salts, individual isomers and mixtures of isomers thereof; which process comprises:

(A)

(1) reacting an aldehyde of Formula XII:

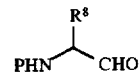

with compound of Formula XVI:

in which each $R^8$, $R^{15}$ and $R^{16}$ are as defined above, and then deprotecting to give a compound of Formula XVII:

(2) reacting the compound of Formula XVII with a compound of Formula VI:

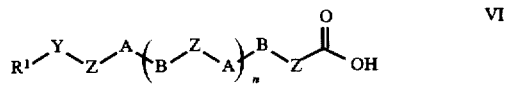

in which each n, A, B, X, Y, Z and $R^1$ are as defined above, and (3) reducing;

(B) optionally further converting a non-salt form of a compound of Formula IV into a pharmaceutically acceptable salt;

(C) optionally further converting a salt form of a compund of Formula IV into non-salt form; and (D) optionally further separating a compound of Formula IV into individual stereoisomers.

\* \* \* \* \*